(12) United States Patent
Porras De Francisco et al.

(10) Patent No.: US 11,969,423 B2
(45) Date of Patent: Apr. 30, 2024

(54) COMPOUNDS

(71) Applicants: GLAXOSMITHKLINE INTELLECTUAL PROPERTY DEVELOPMENT LIMITED, Middlesex (GB); BIOVERSYS AG, Basel (CH)

(72) Inventors: Esther Porras De Francisco, Madrid (ES); Modesto Jesús Remuiñan-Blanco, Madrid (ES); Marilyne Bourotte, Perenchies (FR); Benoit Deprez, Lille (FR); Nicolas Willand, Lille (FR)

(73) Assignees: GLAXOSMITHKLINE INTELLECTUAL PROPERTY DEVELOPMENT LIMITED, Middlesex (GB); BIOVERSYS AG, Basel (CH)

( * ) Notice: Subject to any disclaimer, the term of this patent is extended or adjusted under 35 U.S.C. 154(b) by 0 days.

(21) Appl. No.: 16/639,246

(22) PCT Filed: Aug. 15, 2018

(86) PCT No.: PCT/EP2018/072144
§ 371 (c)(1),
(2) Date: Feb. 14, 2020

(87) PCT Pub. No.: WO2019/034701
PCT Pub. Date: Feb. 21, 2019

(65) Prior Publication Data
US 2020/0253967 A1    Aug. 13, 2020

(30) Foreign Application Priority Data
Aug. 16, 2017 (EP) .................... 17382570

(51) Int. Cl.
| | | |
|---|---|---|
| *C07D 401/04* | (2006.01) | |
| *A61K 31/4545* | (2006.01) | |
| *A61K 31/497* | (2006.01) | |
| *A61K 31/501* | (2006.01) | |
| *A61K 31/506* | (2006.01) | |
| *A61K 45/06* | (2006.01) | |
| *A61P 31/06* | (2006.01) | |

(52) U.S. Cl.
CPC ........ *A61K 31/497* (2013.01); *A61K 31/4545* (2013.01); *A61K 31/501* (2013.01); *A61K 31/506* (2013.01); *A61K 45/06* (2013.01); *A61P 31/06* (2018.01); *C07D 401/04* (2013.01)

(58) Field of Classification Search
None
See application file for complete search history.

(56) References Cited

U.S. PATENT DOCUMENTS

| | | | |
|---|---|---|---|
| 9,957,249 B2 * | 5/2018 | Willand | ............... A61K 31/451 |
| 2011/0136823 A1 | 6/2011 | Deprez et al. | |

FOREIGN PATENT DOCUMENTS

| | | |
|---|---|---|
| WO | WO2004/037810 | 5/2004 |
| WO | WO2008/080969 | 7/2008 |
| WO | WO 2013/060744 A2 | 5/2013 |
| WO | WO 2014/096378 A1 | 6/2014 |

OTHER PUBLICATIONS

Silverman, R. "The Organic Chemistry of Drug Design and Drug Action," 2004, Elsevier, excerpt pp. 29-32.*
Silverman, R. "The Organic Chemistry of Drug Design and Drug Action," 2004, Elsevier, pp. 29-32.*
NIAID "Tubercolosis Drugs and Mechanisms of Action" Apr. 19, 2016, pp. 1-7 (Year: 2016).*
De Clercq, E. et al. "Approved Antiviral Drugs over the Past 50 Years" Clinical Microbiology Reviews, Jul. 2016, 29(3), pp. 695-747 (Year: 2016).*
Marion Flipo, et al. "Ethionamide Boosters: Synthesis, Biological Activity, and Structure-Activity Relationships of a Series of 1,2,4-Oxadiazole EthR Inhibitors". Journal of Medicinal Chemistry, 54(8): 2994-3010 (Apr. 28, 2011).
Marion Flipo, et al. "Ethionamide Boosters. 2. Combining Bioisosteric Replacement and Structure-Based Drug Design to Solve Pharmacokinetic Issues in a Series of Potent 1,2,4-Oxadiazole EthR Inhibitors". Journal of Medicinal Chemistry, 55(1): 68-83 (Jan. 12, 2012).

* cited by examiner

*Primary Examiner* — Medhanit W Bahta
(74) *Attorney, Agent, or Firm* — Withers Bergman LLP; Thomas C. Meyers

(57) ABSTRACT

The invention relates to compounds of Formula (I) and their use in therapy, for example in the treatment of mycobacterial infections or in the treatment of diseases caused by *mycobacterium*, such as tuberculosis.

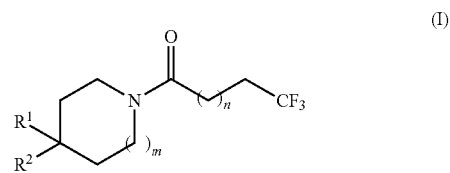

4 Claims, No Drawings

COMPOUNDS

This application is a § 371 of International Application No. PCT/EP2018/072144, filed 15 Aug. 2018, which claims the priority of EP 17382570.4, filed 16 Aug. 2017.

FIELD OF THE INVENTION

The invention relates to compounds, compositions containing them, and their use in therapy, for example in the treatment of mycobacterial infections or in the treatment of diseases caused by infection with a *mycobacterium*, such as tuberculosis (also known as TB).

BACKGROUND TO THE INVENTION

Nearly ten million people are infected with tuberculosis (TB) each year, causing 1.5 million deaths each year, according to a report published by The World Health Organisation in 2014. Despite available treatments for tuberculosis, incidence of the disease still begins to rise, owing to infection by *Mycobacterium tuberculosis*, the causative bacterial agent for TB, becoming resistant to many of the first-line treatments such as isoniazid and rifampicin.

Ethionamide, a structural analogue of isoniazid, is frequently prescribed for the treatment of multidrug-resistant TB (MDR TB), which is as efficient as isoniazid. However, a disadvantage associated with the use of ethionamide is that in order to obtain an acceptable concentration of the drug in the blood, up to 1 g/day is required, which is associated with severe side effects including neurotoxicity and fatal hepatotoxicity. Therefore, there exists a need to reduce the clinical dose and exposure to ethionamide.

Consequently, one aim of the present invention is to provide novel compounds that are likely to be able to potentiate the activity of drugs used in the treatment of TB, in particular drugs that are activatable via the EthA pathway, such as ethionamide.

PCT publication number WO 2014/096378 describes piperidine and pyrrolidine compounds wherein the piperidine or pyrrolidine ring is substituted by various benzyl, phenyl or heterocyclic groups, for example an unsubstituted pyridine group. Such compounds are said to be useful in the treatment of TB.

SUMMARY OF THE INVENTION

In a first aspect of the present invention, there is provided a compound of Formula (I) or a pharmaceutically acceptable salt thereof:

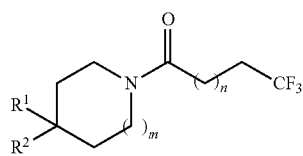

(I)

wherein
n is 1 or 2;
m is 0 or 1;
$R^1$ is H or F; and
$R^2$ is pyridyl optionally substituted by one or two substituents independently selected from fluoro, chloro, bromo, cyano, methyl optionally substituted by one or more fluoro, and methoxy optionally substituted by one or more fluoro, or
$R^2$ is pyrazinyl optionally substituted at the meta position by a substituent selected from fluoro, chloro, bromo, cyano, methyl optionally substituted by one or more fluoro, and methoxy optionally substituted by one or more fluoro, or
$R^2$ is pyrazinyl optionally substituted at the para position by fluoro or chloro,
wherein when $R^1$ is H, $R^2$ is substituted, and when m is 0, $R^1$ is H.

In a second aspect of the present invention, there is provided a compound of Formula (I) or a pharmaceutically acceptable salt thereof for use in therapy.

In a third aspect of the present invention, there is provided a compound of Formula (I) or pharmaceutically acceptable salt thereof, for use in the treatment of a mycobacterial infection or for use in the treatment of a disease caused by infection with a *mycobacterium*.

In a fourth aspect of the present invention, there is provided a compound of Formula (I) or pharmaceutically acceptable salt thereof, for use in the treatment of tuberculosis.

In a fifth aspect of the present invention, there is provided a method for the treatment of a mycobacterial infection in a mammal in need thereof, comprising administering to said mammal a therapeutically effective amount of a compound of Formula (I) or a pharmaceutically acceptable salt thereof.

In a sixth aspect of the present invention, there is provided a method for the treatment of a disease caused by infection with a *mycobacterium* in a mammal in need thereof, comprising administering to said mammal a therapeutically effective amount of a compound of Formula (I) or a pharmaceutically acceptable salt thereof.

In a seventh aspect of the present invention, there is provided the use of a compound of Formula (I) or pharmaceutically acceptable salt thereof, in the manufacture of a medicament for use in the treatment of a mycobacterial infection or a disease caused by infection with a *mycobacterium*.

In an eighth aspect of the present invention, there is provided a pharmaceutical composition comprising (a) a compound of Formula (I) as hereinbefore described or pharmaceutically acceptable salt thereof; and (b) a pharmaceutically acceptable excipient.

In a ninth aspect of the present invention, there is provided a combination of (a) a compound of Formula (I) as hereinbefore described or pharmaceutically acceptable; and (b) at least one other anti-mycobacterial agent.

DETAILED DESCRIPTION OF THE INVENTION

As described above, one aspect of the invention relates to a compound of Formula (I) or a pharmaceutically acceptable salt thereof:

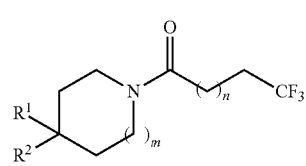

(I)

wherein n is 1 or 2;

m is 0 or 1;

$R^1$ is H or F; and $R^2$ is pyridyl optionally substituted by one or two substituents independently selected from fluoro, chloro, bromo, cyano, methyl optionally substituted by one or more fluoro, and methoxy optionally substituted by one or more fluoro, or $R^2$ is pyrazinyl optionally substituted at the meta position by a substituent selected from fluoro, chloro, bromo, cyano, methyl optionally substituted by one or more fluoro, and methoxy optionally substituted by one or more fluoro, or $R^2$ is pyrazinyl optionally substituted at the para position by fluoro or chloro, wherein when $R^1$ is H, $R^2$ is substituted, and when m is 0, $R^1$ is H.

In one embodiment, the compound of the invention is a compound of Formula (I), as defined above.

In one embodiment, n is 1.

In one embodiment, m is 1.

In one embodiment, $R^1$ is H.

In one embodiment, n is 1, m is 1 and $R^1$ is H.

In one embodiment, particularly when $R^1$ is H, $R^2$ is substituted pyridyl, which may be 2-pyridyl, 3-pyridyl or 4-pyridyl, wherein the substituents are as defined in claim 1.

In one embodiment, when $R^2$ is pyridyl, it is a pyridyl substituted by one or two substituents independently selected from fluoro, chloro, bromo, cyano, methyl optionally substituted by one or more fluoro, and methoxy optionally substituted by one or more fluoro.

In one embodiment, when $R^2$ is pyridyl, it is a pyridyl substituted by one or two substituents independently selected from fluoro, chloro, bromo, cyano, methyl, trifluoromethyl and methoxy.

In one embodiment, when $R^2$ is pyridyl, it is a pyridyl substituted by one or two substituents independently selected from fluoro, chloro, methyl optionally substituted by one or more fluoro and methoxy optionally substituted by one or more fluoro.

In one embodiment, when $R^2$ is pyridyl, it is a pyridyl substituted by one or two substituents independently selected from fluoro, chloro, methyl, trifluoromethyl and methoxy.

In one embodiment, when $R^2$ is 2-pyridyl or 4-pyridyl, it is substituted by one or two substituents independently selected from chloro, fluoro, bromo, cyano, methyl optionally substituted by one or more fluoro, and methoxy optionally substituted by one or more fluoro.

In one embodiment, when $R^2$ is 2-pyridyl, it is substituted by one or two substituents independently selected from chloro, fluoro and trifluoromethyl.

In one embodiment, when $R^2$ is 4-pyridyl, it is substituted by one or two substituents independently selected from fluoro, chloro, methyl and trifluoromethyl.

In one embodiment, when $R^2$ is 3-pyridyl, it is substituted by one or two substituents independently selected from chloro, fluoro, bromo, cyano, methyl optionally substituted by one or more fluoro, and methoxy optionally substituted by one or more fluoro, wherein when the substituent is trifluoromethyl it is attached to the 5-position of the pyridine ring, and when the substituent is methoxy it is attached to the 6-position of the pyridine ring.

In one embodiment, when $R^2$ is 3-pyridyl, it is substituted by one or two substituents independently selected from chloro, fluoro, methoxy and trifluoromethyl, wherein when the substituent is trifluoromethyl it is attached to the 5-position of the pyridine ring, and when the substituent is methoxy it is attached to the 6-position of the pyridine ring. In this embodiment, a methoxy substituent may also be attached to the 5-position of the pyridine ring.

In one embodiment, when $R^2$ is pyrazinyl, it is substituted by chloro at the meta position or para position, or it is substituted by trifluoromethyl at the meta position.

In one embodiment, n is 1, m is 1 and $R^2$ is pyridyl substituted by one or two substituents, wherein when $R^2$ is 2-pyridyl or 4-pyridyl, the substituents are independently selected from chloro, fluoro, bromo, cyano, methyl optionally substituted by one or more fluoro, and methoxy optionally substituted by one or more fluoro; and when $R^2$ is 3-pyridyl, the substituents are independently selected from chloro, fluoro, bromo, cyano, methyl optionally substituted by one or more fluoro, and methoxy optionally substituted by one or more fluoro, wherein when the substituent is trifluoromethyl it is attached to the 5-position of the pyridine ring, and when the substituent is methoxy it is attached to the 6-position of the pyridine ring.

In one embodiment, n is 1, m is 1 and $R^2$ is pyridyl substituted by one or two substituents, wherein when $R^2$ is 2-pyridyl, the substituents are independently selected from chloro, fluoro and trifluoromethyl;

when $R^2$ is 3-pyridyl, the substituents are independently selected from chloro, fluoro, methoxy and trifluoromethyl, wherein when the substituent is trifluoromethyl it is attached to the 5-position of the pyridine ring, and when the substituent is methoxy it is attached to the 6-position of the pyridine ring; and when $R^2$ is 4-pyridyl, the substituents are independently selected from fluoro, chloro, methyl and trifluoromethyl.

In one embodiment, n is 1, m is 1 and $R^2$ is 3-pyridyl substituted by one or two substituents independently selected from chloro, fluoro, methoxy and trifluoromethyl, wherein when the substituent is trifluoromethyl it is attached to the 5-position of the pyridine ring, and when the substituent is methoxy it is attached to the 6-position of the pyridine ring.

In one embodiment, $R^2$ is 3-pyridyl substituted by chloro, fluoro or trifluoromethyl, or $R^2$ is 4-pyridyl substituted by fluoro or trifluoromethyl.

In one embodiment, n is 1, m is 1 and $R^2$ is 3-pyridyl substituted by chloro or fluoro, or $R^2$ is 4-pyridyl substituted by fluoro or trifluoromethyl.

In one embodiment, $R^2$ is 4-pyridyl substituted by one substituent which is trifluoromethyl.

In one embodiment, $R^2$ is pyridyl optionally substituted by one or two substituents independently selected from fluoro, chloro, methyl, trifluoromethyl, and methoxy, wherein when the substituent is trifluoromethyl it is attached at the meta position of the pyridine ring; or $R^2$ is pyrazinyl meta substituted by one or two substituents independently selected from fluoro, chloro and trifluoromethyl; or $R^2$ is pyrazinyl para substituted by fluoro or chloro.

In one embodiment, n is 1, m is 1, $R^1$ is H and $R^2$ is pyridyl substituted by one or two substituents independently selected from fluoro, chloro, methyl, trifluoromethyl, and methoxy, wherein when the substituent is trifluoromethyl it is attached at the meta position of the pyridine ring; or $R^2$ is pyrazinyl meta substituted by one or two substituents independently selected from fluoro, chloro and trifluoromethyl; or $R^2$ is pyrazinyl para substituted by fluoro or chloro.

In one embodiment, $R^2$ is pyridyl substituted by one or two substituents independently selected from fluoro, chloro, methyl, trifluoromethyl, and methoxy, wherein when the substituent is trifluoromethyl it is attached at the meta position of the pyridine ring; or $R^2$ is pyrazinyl meta substituted by one or two substituents independently selected from fluoro, chloro and trifluoromethyl; or $R^2$ is pyrazinyl para substituted by fluoro or chloro.

In one embodiment, n is 1, m is 1, $R^1$ is H and $R^2$ is pyridyl substituted by one substituent selected from fluoro, chloro, methyl, trifluoromethyl, and methoxy, wherein when the substituent is trifluoromethyl it is attached at the meta position of the pyridine ring; or $R^2$ is pyrazinyl meta substituted by one substituent selected from fluoro, chloro and trifluoromethyl; or $R^2$ is pyrazinyl para substituted by fluoro or chloro.

In one embodiment, n is 1, m is 1, $R^1$ is H and $R^2$ is 2-pyridyl substituted by one or two substituents independently selected from fluoro, chloro and trifluoromethyl; or $R^2$ is 3-pyridyl substituted by one or two substituents independently selected from fluoro, chloro, methoxy and trifluoromethyl; or $R^2$ is 4-pyridyl substituted by one or two substituents independently selected from fluoro, chloro, methyl and trifluoromethyl; or $R^2$ is pyrazinyl meta substituted by one substituent selected from fluoro, chloro and trifluoromethyl; or $R^2$ is pyrazinyl para substituted by fluoro or chloro.

In one embodiment, n is 1, m is 1, $R^1$ is H and $R^2$ is 4-pyridyl substituted by one substituent which is trifluoromethyl.

In another embodiment, $R^2$ is 3-pyridyl substituted by one substituent which is chloro.

In one embodiment, n is 1 and m is 0. As noted above, when m is 0, $R^1$ is H. In this embodiment, $R^2$ is preferably pyridyl substituted by one or two substituents independently selected from fluoro, chloro, bromo, cyano, methyl optionally substituted by one or more fluoro, and methoxy optionally substituted by one of more fluoro. The pyridyl may be 2-pyridyl, 3-pyridyl or 4-pyridyl. In this embodiment, $R^2$ is preferably 3-pyridyl or 4-pyridyl substituted by one or two substituents.

In one embodiment, n is 1, m is 0 and $R^2$ is substituted pyridyl, which may be 2-pyridyl, 3-pyridyl or 4-pyridyl, wherein the substituent is selected from chloro and trifluoromethyl. In this embodiment, $R^2$ is preferably substituted 3-pyridyl or 4-pyridyl, particularly 3-pyridyl.

In one embodiment, n is 1, m is 0, $R^1$ is H and $R^2$ is substituted pyridyl, which may be 2-pyridyl, 3-pyridyl or 4-pyridyl, wherein the substituents are as defined in claim 1. In this embodiment, $R^2$ is preferably substituted 3-pyridyl or 4-pyridyl. In particular, when m is 0, $R^2$ is 3-pyridyl substituted by one substituent which is chloro.

In one embodiment, $R^1$ is F. In this particular embodiment, wherein $R^1$ is F, $R^2$ is pyridyl substituted by one substituent selected from fluoro, chloro and trifluoromethyl. Alternatively, $R^2$ may be pyrazinyl substituted by chloro. In a further embodiment, $R^2$ is 3-pyridyl or 4-pyridyl substituted by one substituent, wherein the substituent is chloro, fluoro or trifluoromethyl. In an alternative embodiment, $R^2$ is unsubstituted pyridyl, in particular 2-pyridyl.

In an embodiment, when $R^1$ is F, $R^2$ is selected from unsubstituted pyridyl or pyridyl substituted by one substituent selected from fluoro, chloro and trifluoromethyl.

In an embodiment, when $R^1$ is F, $R^2$ is selected from unsubstituted 2-pyridyl and 3-pyridyl; or 2-pyridyl substituted by trifluoromethyl; or 3-pyridyl substituted by fluoro, chloro or trifluoromethyl; or 4-pyridyl substituted by fluoro, chloro or trifluoromethyl.

Alternatively, when $R^1$ is F, $R^2$ is 3-pyridyl or 4-pyridyl substituted by one or two substituents independently selected from fluoro, chloro, bromo, cyano, methyl optionally substituted by one or more fluoro, or methoxy optionally substituted by one of more fluoro. In one particular embodiment, the substituent is fluoro or chloro.

In one embodiment, $R^2$ is substituted by one substituent selected from fluoro, chloro, bromo, cyano, methyl optionally substituted by one or more fluoro, or methoxy optionally substituted by one of more fluoro.

In all of the above described embodiments, it is preferable that $R^2$, when substituted, is substituted at the meta position.

In one embodiment, when $R^2$ is pyridyl, it is substituted by one substituent at the meta position which is selected from chloro, fluoro, methyl, methoxy and trifluoromethyl.

In one embodiment, when $R^2$ is pyrazinyl, it is substituted by one substituent at the meta position which is fluoro, chloro or trifluoromethyl.

In all of the above described embodiments, it is preferable that $R^2$, when substituted, is substituted by one substituent only.

Particular compounds which are useful in the present invention include:

4,4,4-trifluoro-1-[4-fluoro-4-(3-pyridyl)-1-piperidyl]butan-1-one;

4,4,4-trifluoro-1-[4-(5-fluoro-3-pyridyl)-1-piperidyl]butan-1-one;

4,4,4-trifluoro-1-[4-(6-fluoro-3-pyridyl)-1-piperidyl]butan-1-one;

4,4,4-trifluoro-1-[4-[6-(trifluoromethyl)-3-pyridyl]-1-piperidyl]butan-1-one;

4,4,4-trifluoro-1-[4-[4-(trifluoromethyl)-2-pyridyl]-1-piperidyl]butan-1-one;

4,4,4-trifluoro-1-[4-[5-(trifluoromethyl)-3-pyridyl]-1-piperidyl]butan-1-one;

4,4,4-trifluoro-1-[4-[6-(trifluoromethyl)-2-pyridyl]-1-piperidyl]butan-1-one;

4,4,4-trifluoro-1-[4-(6-fluoro-2-pyridyl)-1-piperidyl]butan-1-one;

4,4,4-trifluoro-1-[4-(6-methoxy-3-pyridyl)-1-piperidyl]butan-1-one;

4,4,4-trifluoro-1-[4-[2-(trifluoromethyl)-3-pyridyl]-1-piperidyl]butan-1-one;

4,4,4-trifluoro-1-[4-(5-methoxy-3-pyridyl)-1-piperidyl]butan-1-one;

1-[4-(3,5-difluoro-2-pyridyl)-1-piperidyl]-4,4,4-trifluorobutan-1-one;

1-[4-(2,6-difluoro-3-pyridyl)-1-piperidyl]-4,4,4-trifluorobutan-1-one;

4,4,4-trifluoro-1-[4-(5-fluoro-2-pyridyl)-1-piperidyl]butan-1-one;

4,4,4-trifluoro-1-(4-(2-(trifluoromethyl)pyridin-4-yl)piperidin-1-yl)butan-1-one;

4,4,4-trifluoro-1-(4-(2-fluoropyridin-4-yl)piperidin-1-yl)butan-1-one;

4,4,4-trifluoro-1-(4-(5-(trifluoromethyl)pyrazin-2-yl)piperidin-1-yl)butan-1-one;

4,4,4-trifluoro-1-(4-(2-methylpyridin-4-yl)piperidin-1-yl)butan-1-one;

1-(4-(5,6-difluoropyridin-3-yl)piperidin-1-yl)-4,4,4-trifluorobutan-1-one;

4,4,4-trifluoro-1-(4-(6-(trifluoromethyl)pyrazin-2-yl)piperidin-1-yl)butan-1-one;

1-(4-(2-chloropyridin-4-yl)piperidin-1-yl)-4,4,4-trifluorobutan-1-one;

4,4,4-trifluoro-1-(4-(3-fluoropyridin-4-yl)piperidin-1-yl)butan-1-one;

1-(4-(6-chloropyridin-2-yl)piperidin-1-yl)-4,4,4-trifluorobutan-1-one;

1-(4-(5-chloropyridin-3-yl)-4-fluoropiperidin-1-yl)-4,4,4-trifluorobutan-1-one;
1-(4-(5-chloropyridin-3-yl)piperidin-1-yl)-4,4,4-trifluorobutan-1-one;
1-(4-(5-chloropyridin-3-yl)piperidin-1-yl)-5,5,5-trifluoropentan-1-one;
1-(4-(6-chloropyrazin-2-yl)piperidin-1-yl)-4,4,4-trifluorobutan-1-one;
4,4,4-trifluoro-1-(4-fluoro-4-(pyridin-2-yl)piperidin-1-yl)butan-1-one;
4,4,4-trifluoro-1-(4-fluoro-4-(5-(trifluoromethyl)pyridin-3-yl)piperidin-1-yl)butan-1-one;
4,4,4-trifluoro-1-(4-fluoro-4-(2-(trifluoromethyl)pyridin-4-yl)piperidin-1-yl)butan-1-one;
1-(4-(6-chloropyrazin-2-yl)-4-fluoropiperidin-1-yl)-4,4,4-trifluorobutan-1-one;
4,4,4-trifluoro-1-(4-fluoro-4-(2-fluoropyridin-4-yl)piperidin-1-yl)butan-1-one;
4,4,4-trifluoro-1-[4-fluoro-4-[4-(trifluoromethyl)-2-pyridyl]-1-piperidyl]butan-1-one;
4,4,4-trifluoro-1-[4-fluoro-4-[4-(trifluoromethyl)-2-pyridyl]-1-piperidyl]butan-1-one;
1-(3-(5-chloropyridin-3-yl)pyrrolidin-1-yl)-4,4,4-trifluorobutan-1-one; and
1-[4-(2-chloro-4-pyridyl)-4-fluoro-1-piperidyl]-4,4,4-trifluoro-butan-1-one.

In one embodiment, the compound of the invention is 4,4,4-trifluoro-1-(4-(2-(trifluoromethyl)pyridin-4-yl)piperidin-1-yl)butan-1-one having the following structure:

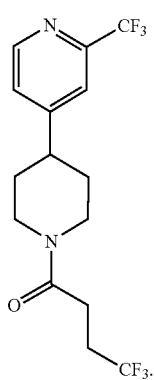

Also disclosed herein is a compound of Formula (II) or pharmaceutically acceptable salt thereof:

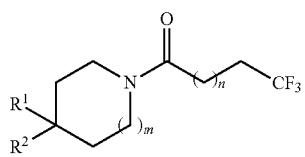

(II)

wherein n is 1 or 2; m is 0 or 1; $R^1$ is H or F; and
$R^2$ is pyridyl, pyrazinyl, pyrimidinyl or pyridazinyl, each of which is optionally substituted by one or two substituents independently selected from fluoro, chloro, bromo, cyano, methyl optionally substituted by one or more fluoro, and methoxy optionally substituted by one or more fluoro, wherein when $R^1$ is H and $R^2$ is pyridyl, the pyridyl is substituted, and when m is 0, $R^1$ is H, with the proviso that the compound is other than

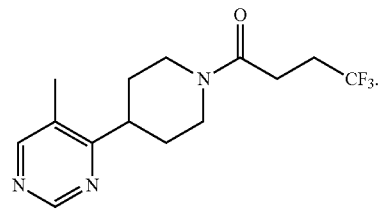 [SMILES: Cc1cncnc1C1CCN(C(=O)CCC(F)(F)F)CC1]

For the avoidance of doubt,

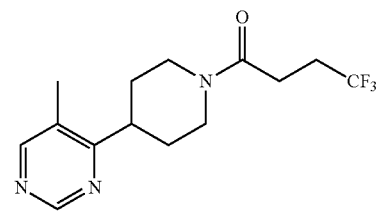 [SMILES: Cc1cncnc1C1CCN(C(=O)CCC(F)(F)F)CC1]

has the name 4,4,4-trifluoro-1-(4-(5-methylpyrimidin-4-yl)piperidin-1-yl)butan-1-one.

Each of the above described embodiments also apply in respect of Formula (II).

Terms and Definitions

As used herein, the term "pyridyl" refers to a pyridine substituent group, which includes 2-pyridyl, 3-pyridyl and 4-pyridyl. For the avoidance of doubt, the following IUPAC numbering system in relation to 2-pyridyl, 3-pyridyl and 4-pyridyl is used:

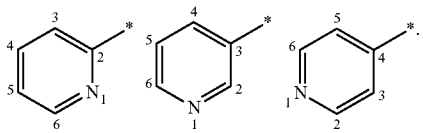

As depicted above, * represents the point of attachment.

When the term "meta" or "para" is used in relation to pyridyl or pyrazinyl, it is intended to take its normal meaning in the art, i.e., meta substitution relative to the point of attachment or para substitution relative to the point of attachment.

For the avoidance of doubt, when the term "meta" is used in relation to substitution with reference to 2-pyridyl it is intended to mean substitution at the 4- or 6-position, as defined above.

For the avoidance of doubt, when the term "meta" is used in relation to substitution with reference to 3-pyridyl it is intended to mean substitution at the 5-position, as defined above.

For the avoidance of doubt, when the term "meta" is used in relation to substitution with reference to 4-pyridyl it is intended to mean substitution at the 2- or 6-position, as defined above.

As used herein, the term "pyrazinyl" refers to a pyrazine substituent group. When the term "meta" or "para" are used in relation to substitution with reference to pyrazinyl, they are intended to take their normal meaning in the art, i.e., meta or para substituted relative to the point of attachment.

For the avoidance of doubt, when the term "para" is used in relation to substitution with reference to a pyrazinyl it is intended to mean that substitution is directly opposition the point of attachment, i.e. at the 5-position as depicted below:

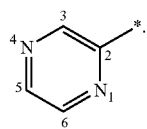

For the avoidance of doubt, when the term "meta" is used in relation to substitution with reference to pyrazinyl it is intended to mean that that substitution is at the 6-position when depicted as above.

As used herein, the terms "pyrimidinyl" and "pyridazinyl" refer a pyrimidine or pyridazine substituent group.

As used herein, the term "cyano" refers to —CN.

As used herein, the term "methyl optionally substituted by one or more fluoro" refers to a methyl group which may be substituted by one, two or three fluorine atoms. Therefore, the term "methyl optionally substituted by one or more fluoro" includes methyl, mono-fluoromethyl (—CH$_2$F), di-fluoromethyl (—CHF$_2$) and trifluoromethyl (—CF$_3$).

As used herein, the term "methoxy optionally substituted by one or more fluoro" refers to a methoxy group wherein the carbon of the methyl group may be substituted by one, two or three fluorine atoms. Therefore, the term "methyl optionally substituted by one or more fluoro" includes methoxy, mono-fluoromethoxy (—OCH$_2$F), di-fluoromethoxy (—OCHF$_2$) and trifluoromethoxy (—OCF$_3$).

The term "compounds of the invention" as used herein means a compound of Formula (I) or a pharmaceutically acceptable salt thereof. The term "a compound of the invention" means any one of the compounds of the invention as defined above.

Furthermore, it will be understood that phrases such as "a compound of Formula (I) or a pharmaceutically acceptable salt thereof" or "compounds of the invention" are intended to encompass the compound of Formula (I), a pharmaceutically acceptable salt or solvate of the compound of Formula (I), or any pharmaceutically acceptable combination of these. Thus by way of non-limiting example used here for illustrative purpose, "a compound of Formula (I) or a pharmaceutically acceptable salt thereof" encompasses a pharmaceutically acceptable salt of a compound of Formula (I) which is present as a solvate, and this phrase also encompasses a mixture of a compound of Formula (I) and a pharmaceutically acceptable salt of a compound of Formula (I).

It is to be understood that references herein to a compound of Formula (I) or a pharmaceutically acceptable salt thereof includes a compound of Formula (I) as a free base or as a pharmaceutically acceptable salt thereof. Thus, in one embodiment, the invention is directed to a compound of Formula (I). In another embodiment, the invention is directed to a pharmaceutically acceptable salt of a compound of Formula (I).

The term "pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Pharmaceutically acceptable salts include, amongst others, those described in Berge, J. Pharm. Sci., 1977, 66, 1-19, or those listed in P H Stahl and C G Wermuth, editors, *Handbook of Pharmaceutical Salts; Properties, Selection and Use, Second Edition* Stahl/Wermuth: Wiley-VCH/VHCA, 2011 (see http://wiley.com/WileyCDA/WileyTitle/productCd-3906390519.html).

Suitable pharmaceutically acceptable salts can include acid addition salts. Such salts can be formed by reaction with the appropriate acid, optionally in a suitable solvent such as an organic solvent, to give the salt which can be isolated by crystallisation and filtration.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, cam phorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

As used herein, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder.

An appropriate "therapeutically effective amount" will depend upon a number of factors including, for example, the age and weight of the subject, the precise condition requiring treatment and its severity, the nature of the formulation, and the route of administration, and will ultimately be at the discretion of the attendant physician.

The compounds of Formula (I), wherein m is 0, may contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in Formula (I), or in any chemical structure illustrated herein, is not specified, the structure is intended to encompass any stereoisomer and all mixtures thereof. Thus, compounds of Formula (I) containing one or more chiral centres may be used as racemic modifications including racemic mixtures and racemates, enantiomerically-enriched mixtures, or as enantiomerically-pure individual stereoisomers.

Compound Preparation

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention. Specific compounds of the invention can be prepared according to the experimental procedures disclosed in the Examples section.

The general procedures used to synthesise the compounds of Formula (I) are described in reaction Schemes 1-17 below and are illustrated in the Examples.

Preparation of Compounds of Formula (I)

Compounds of Formula (I) wherein m=1, n=1 or 2, $R^1$ is H and $R^2$ are as defined hereinbefore may be prepared according to Scheme 1 by BOC deprotection of amino compounds of Formula (III) using hydrogen chloride followed by coupling of the corresponding HCl salt of Formula (II) with commercially available 4,4,4-trifluorobutanoic acid or 5,5,5-trifluoropentanoic or with Intermediate of Formula (IV). Alternatively, compounds with Formula (I) can be prepared by reaction of the corresponding commercially available amino compounds as HCl salts of Formula (II) with 4,4,4-trifluorobutanoylbenzotriazole.

Alternatively, compounds with Formula (I) wherein m=1, n=1, $R^1$ is H and $R^2$ are as defined hereinbefore may be prepared according to Scheme 2 by catalytic hydrogenation of compounds of Formula (V).

Compound of Formula (VI) which is a pyridine compound of Formula (I) wherein m=1, n=1, $R^1$ is H and $R^2$ is 5-fluoro-3-pyridyl can be prepared according Scheme 3 by coupling compound of Formula (VII) with (5-fluoro-3-pyridyl)boronic acid.

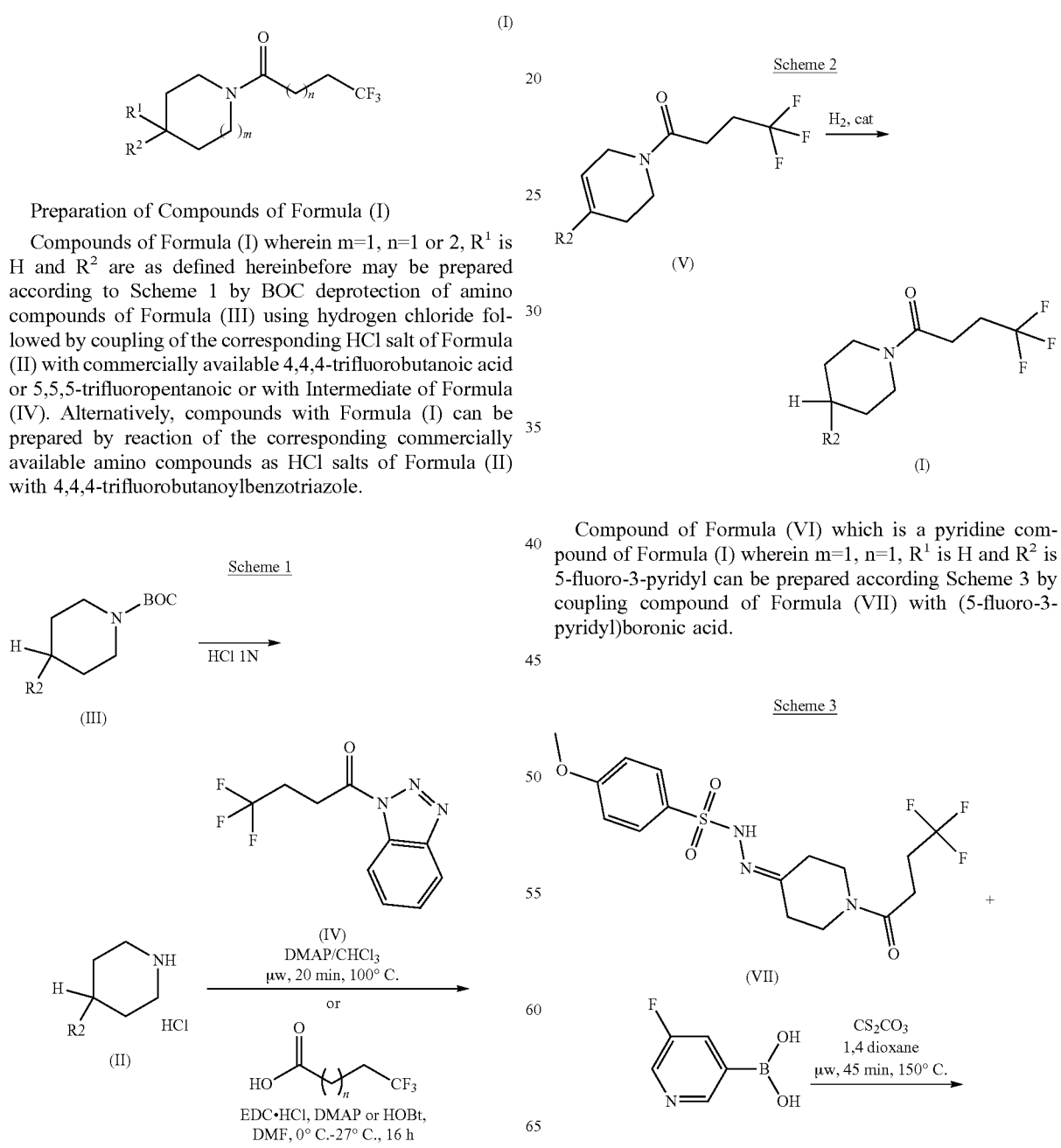

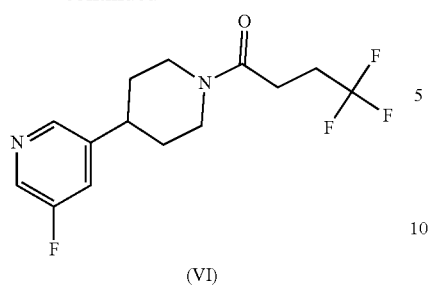

(VI)

Compounds of Formula (VIII) which are 4-fluoropiperidine compounds of Formula (I) wherein m=1, n=1, $R^1$ is F and $R^2$ are as defined hereinbefore may be prepared according to Scheme 4 by fluorination of the corresponding 4-hydroxypiperidines of Formula (IX).

Scheme 4

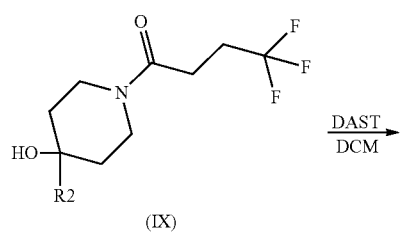

(IX)

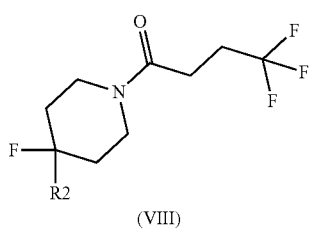

(VIII)

Alternatively, compound with Formula (X) which is 4-fluoropiperidine compound of Formula (I) wherein m=1, n=1, $R^1$ is F and $R^2$ is 5-chloropyridin-3-yl can be prepared according to Scheme 5 by coupling of the corresponding amine HCl salt of Formula (XI) with 4,4,4-trifluorobutanoic acid.

Scheme 5

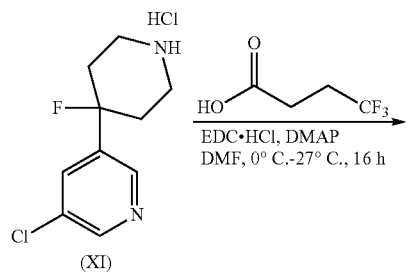

(XI)

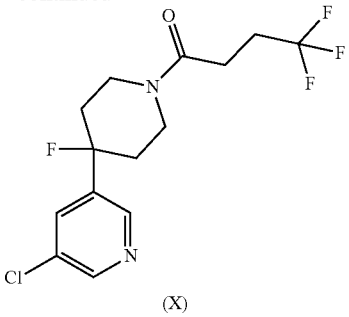

(X)

Compound of Formula (XII) which is a 6-chloropyzarin2-yl compound of Formula (I) wherein m=1, n=1, $R^1$ is H and $R^2$ is 6-chloropyzarin2-yl can be prepared according Scheme 6 by chlorination of corresponding 6-aminopyzarin2-yl compound of Formula (XIII).

Scheme 6

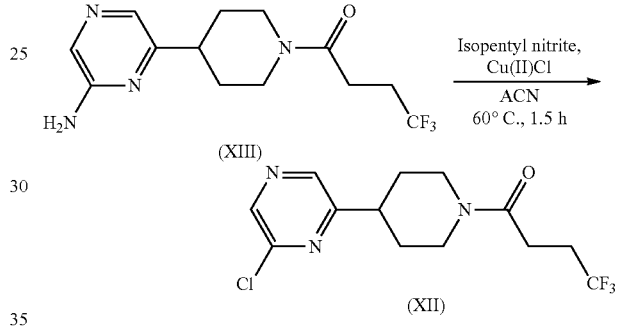

Compound of Formula (XIV) which is a pyrrolidine compound of Formula (I) wherein m=0, n=1, $R^1$ is H and $R^2$ is 5-chloropyridin2-yl can be prepared according Scheme 7 by coupling of the corresponding HCl salt of Formula (XV) with 4,4,4-trifluorobutanoic acid.

Scheme 7

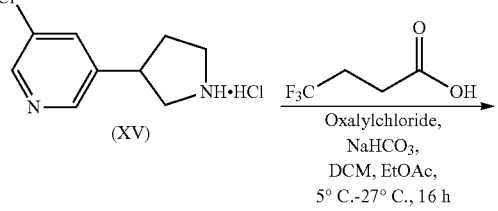

Preparation of Intermediates

Intermediate of Formula (IV) can be prepared according to Scheme 8 by coupling the commercially available 4,4,4-trifluorobutanoic acid with 1H-benzotriazole in presence of thionyl chloride.

Scheme 8

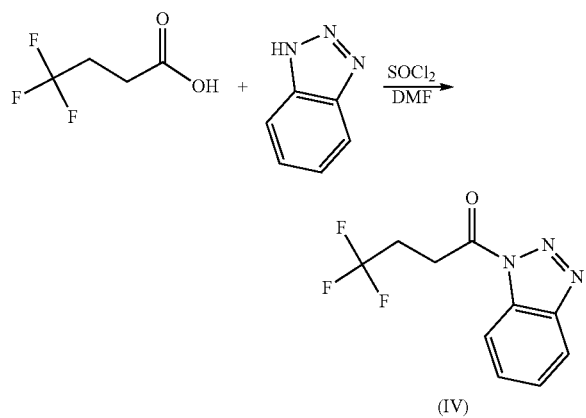

Piperidine intermediates of Formula (V) wherein m=1, n=1, R¹ is H and R² are as defined hereinbefore may be prepared according to Scheme 9 by BOC deprotection of amino compounds of Formula (XVI) using hydrogen chloride followed by coupling of the corresponding HCl salt with Intermediate of Formula (IV) 4,4,4-trifluorobutanoyl-benzotriazole. Intermediates of Formula (XVI) can be prepared by coupling of commercially available tert-butyl 4-(4,4,5,5-tetramethyl-1,3,2-dioxaborolan-2-yl)-5,6-dihydropyridine-1 (2H)-carboxylate with the corresponding bromine derivative.

Scheme 9

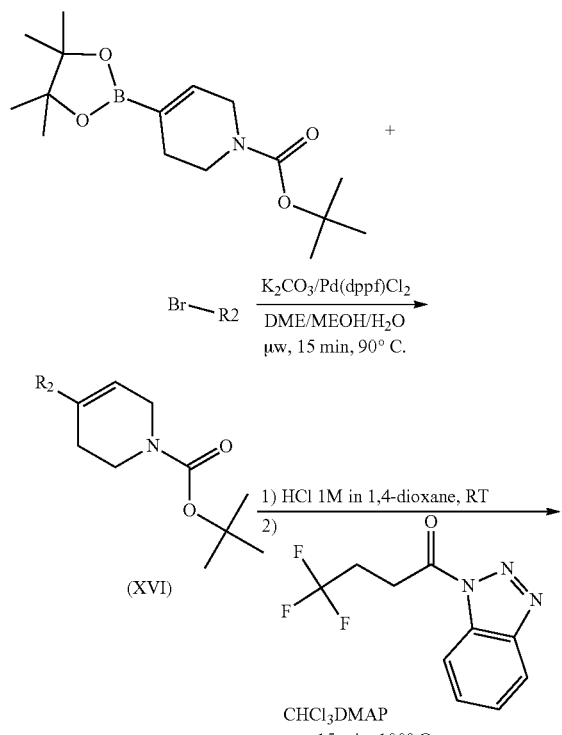

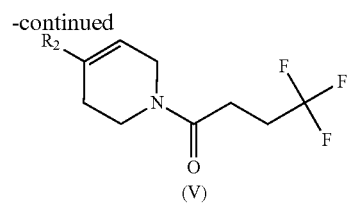

Alternatively, piperidine intermediates of Formula (V) wherein m=1, n=1, R¹ is H and R² are as defined hereinbefore may be prepared according to Scheme 10 by coupling of intermediate of Formula (XVII) with the corresponding commercially available bromine derivative. Intermediate of Formula (XVII) can be prepared by BOC deprotection of commercially available tert-butyl 4-(4,4,5,5-tetramethyl-1,3,2-dioxaborolan-2-yl)-5,6-dihydropyridine-1 (2H)-carboxylate using hydrogen chloride followed by coupling of the corresponding HCl salt of Formula (XVIII) with 4,4,4-trifluorobutanoic acid.

Scheme 10

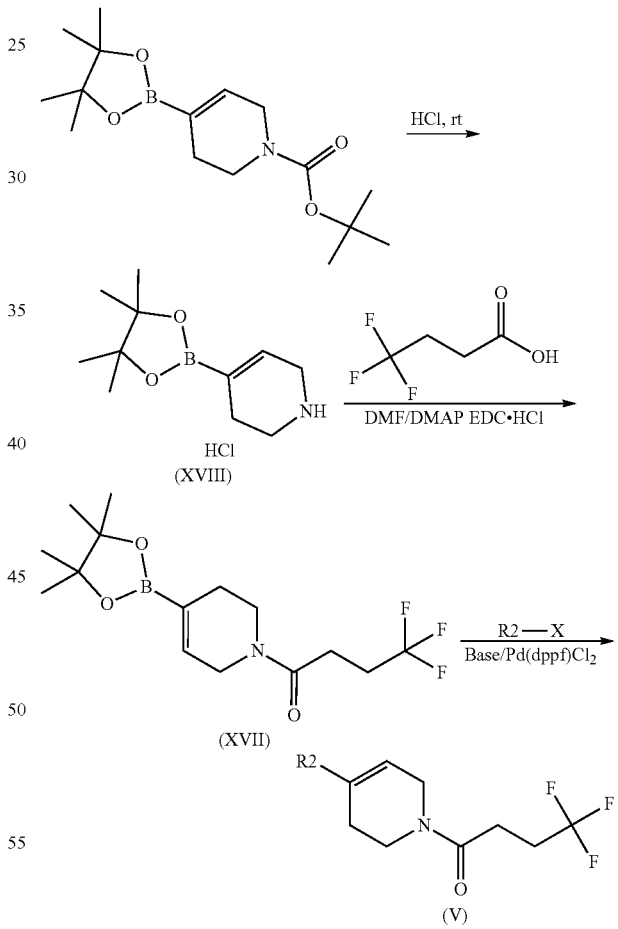

Intermediate of Formula (VII) may be prepared according to Scheme 11 by reaction of commercially available 4-methoxybenzenesulfonohydrazide with protected aminoketone of Formula (XIX) in methanol. Intermediate of Formula (XIX) can be quickly synthesized by coupling reaction of benzotriazole of Formula (IV) with commercially available piperidin-4-one hydrochloride in the presence of 4-dimethylaminopyridine.

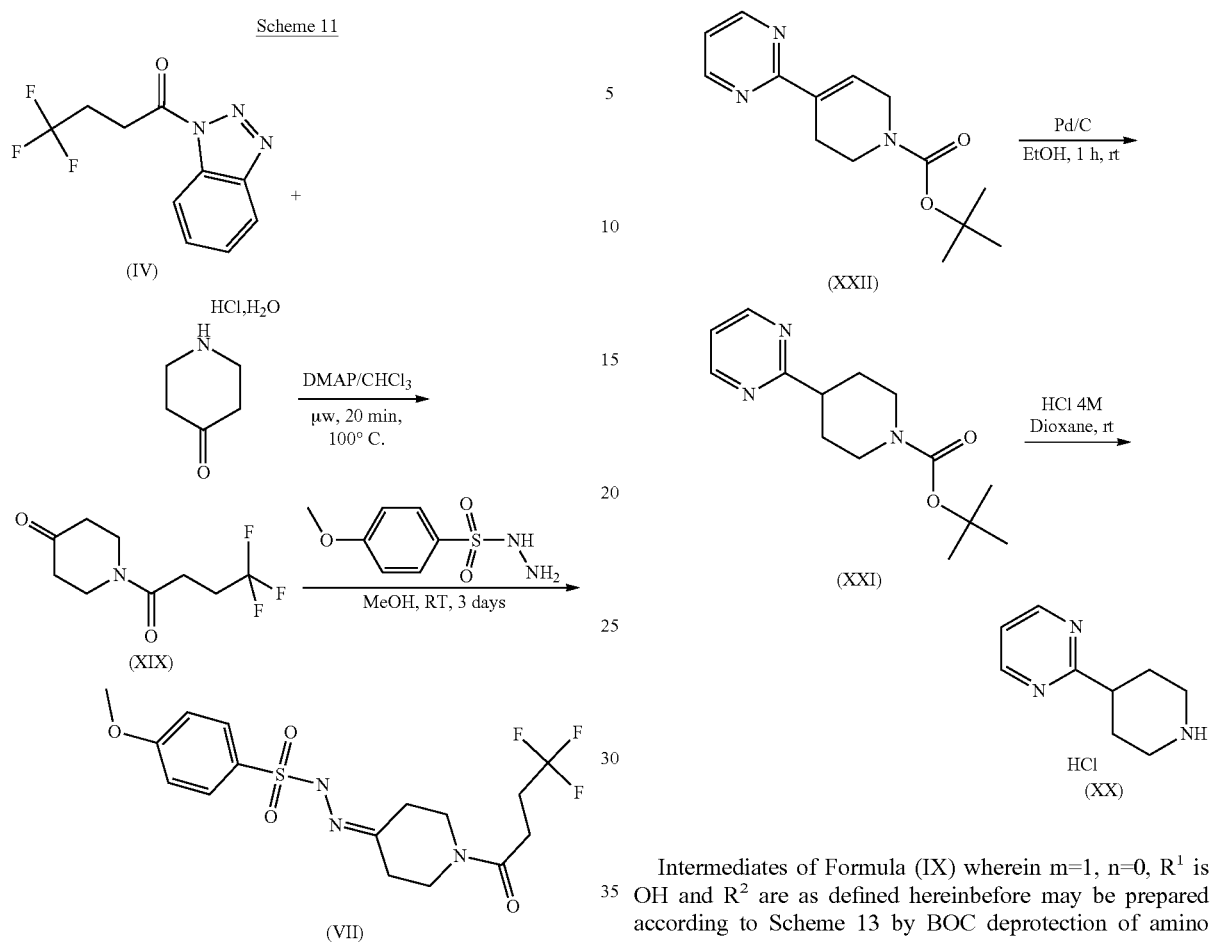

Intermediate of Formula (XX) may be prepared according to Scheme 12 by cleavage of N-Boc protecting group of intermediate of Formula (XXI) under standard acidic conditions. Intermediate of Formula (XXI) can be obtained from alkene of Formula (XXII) by hydrogenation under catalytic conditions. Intermediate of Formula (XXII) can be prepared by Suzuki coupling of commercially available tert-butyl 4-(4,4,5,5-tetramethyl-1,3,2-dioxaborolan-2-yl)-5,6-dihydropyridine-1(2H)-carboxylate and 2-bromopyrimidine under standard conditions.

Intermediates of Formula (IX) wherein m=1, n=0, $R^1$ is OH and $R^2$ are as defined hereinbefore may be prepared according to Scheme 13 by BOC deprotection of amino compounds of Formula (XXIV) using hydrogen chloride followed by coupling of the corresponding HCl salt of Formula (XXIII) with commercially available 4,4,4-trifluorobutanoic acid. Intermediates of Formula (XXIV) can be prepared by butyllithium-mediated coupling of the corresponding Bromide derivative with the commercially avalilable ketone tert-butyl 4-oxopiperidine-1-carboxylate.

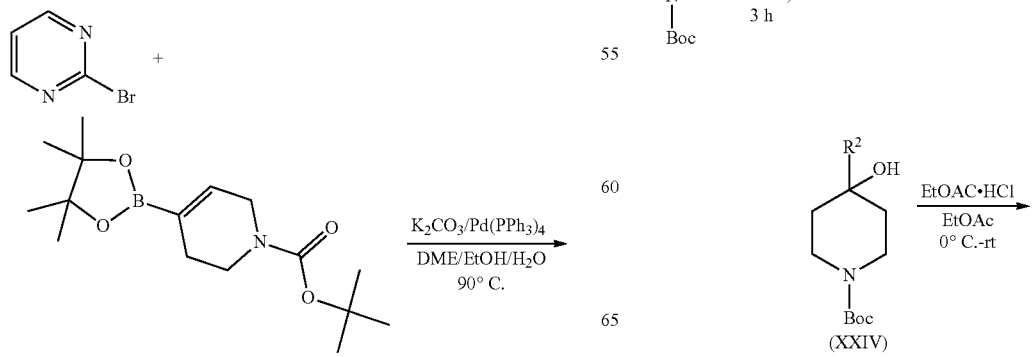

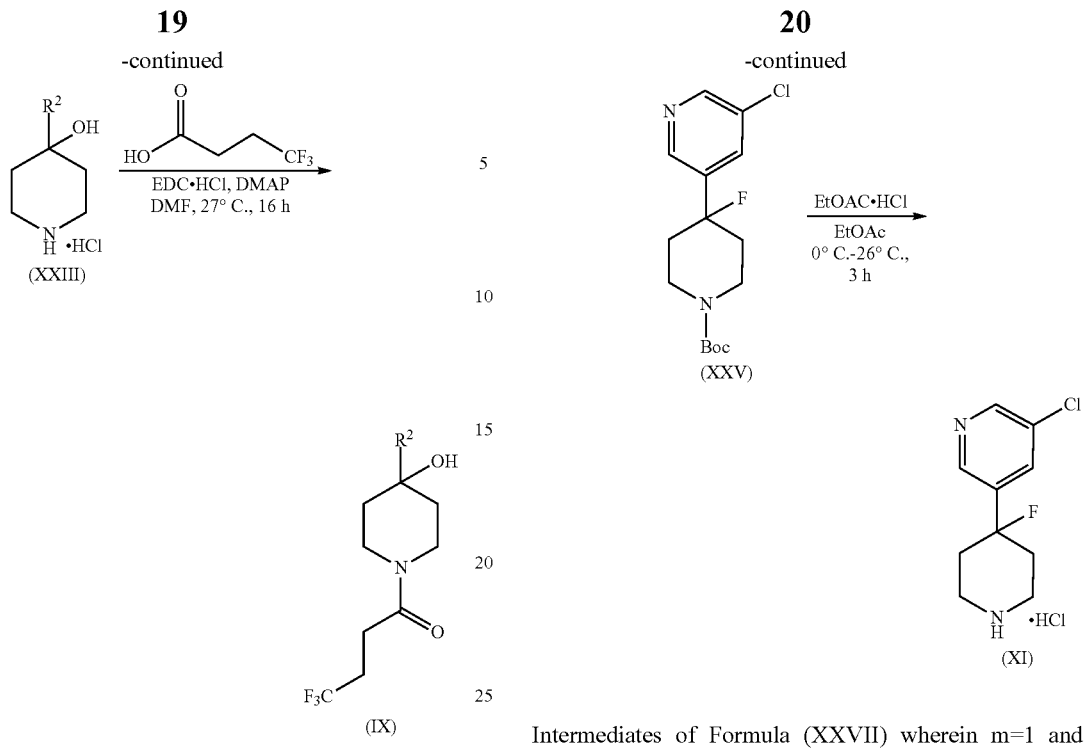

Intermediate of Formula (XI) may be prepared according to Scheme 14 by fluorination of 4-hydroxypiperidine of Formula (XXVI) followed by coupling of the corresponding HCl salt of Formula (XXV) with commercially available 4,4,4-trifluorobutanoic acid. Intermediate of Formula (XXVI) can be prepared by butyllithium-mediated coupling of 3-bromo-5-chloropyridine with tert-butyl 4-oxopiperidine-1-carboxylate.

Intermediates of Formula (XXVII) wherein m=1 and Formula (XV) wherein m=0 may be prepared according to Scheme 15 by chlorination of corresponding aminopyridine compound of Formula (XXIX) followed by cleavage of N-Boc protective group of intermediate of Formula (XXVIII) under standard acidic conditions. Aminopyridine compound of Formula (XXIX) where m=0,1 can be prepared by catalytic reduction of double bond of compound with Formula (XXX).

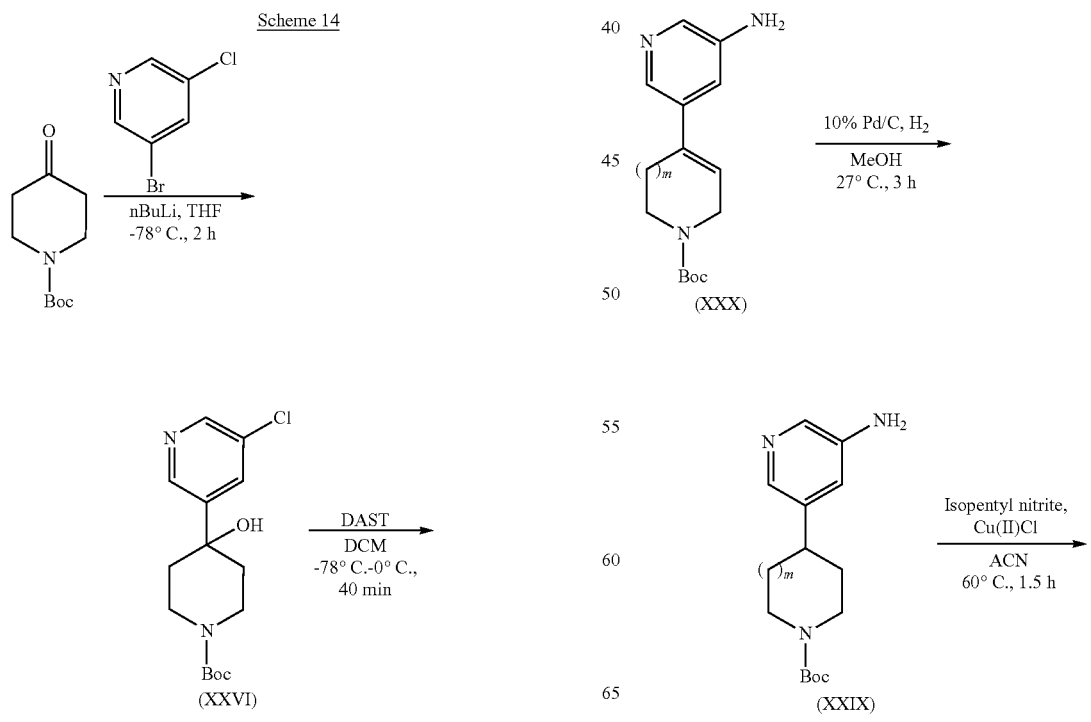

-continued

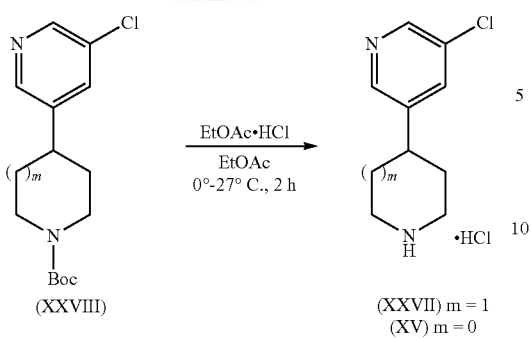

Intermediate of Formula (XXX) wherein m=1 may be prepared according to Scheme 16 by coupling of commercially available tert-butyl 4-(4,4,5,5-tetramethyl-1,3,2-dioxaborolan-2-yl)-5,6-dihydropyridine-1(2H)-carboxylate and 5-bromopyrazin-3-amine.

Scheme 16

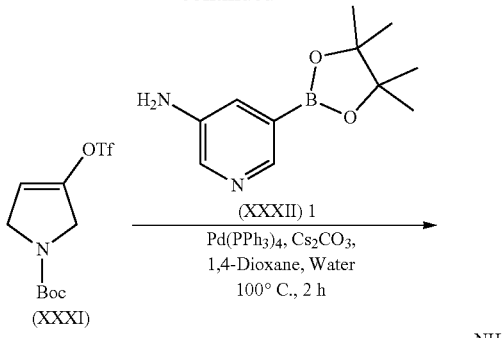

Pyrrolidine intermediate of Formula (XXX) wherein m=0 may be prepared according to Scheme 17 by suzuki coupling of aminopyridilboronate compound of Formula (XXXII) and triflate compound of Formula (XXXI) under standard conditions. Triflate compound of Formula (XXXI) can be obtained by reaction alkylation of commercially available tert-butyl 3-oxopyrrolidine-1-carboxylate with 1,1,1-trifluoro-N-phenyl-N-((trifluoromethyl)sulfonyl) methanesulfonamide in the presence of NaHMDS. Intermediate of Formula (XXXII) can be easily prepared by Pd-mediated coupling of commercially available 5-bromopyridin-3-amine with 4,4,4',4',5,5,5',5'-octamethyl-2,2'-bi(1,3,2-dioxaborolane) under standard basic conditions.

Scheme 17

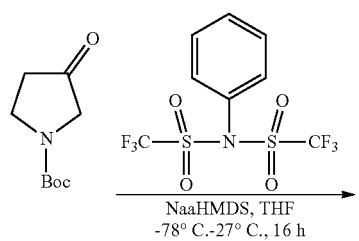

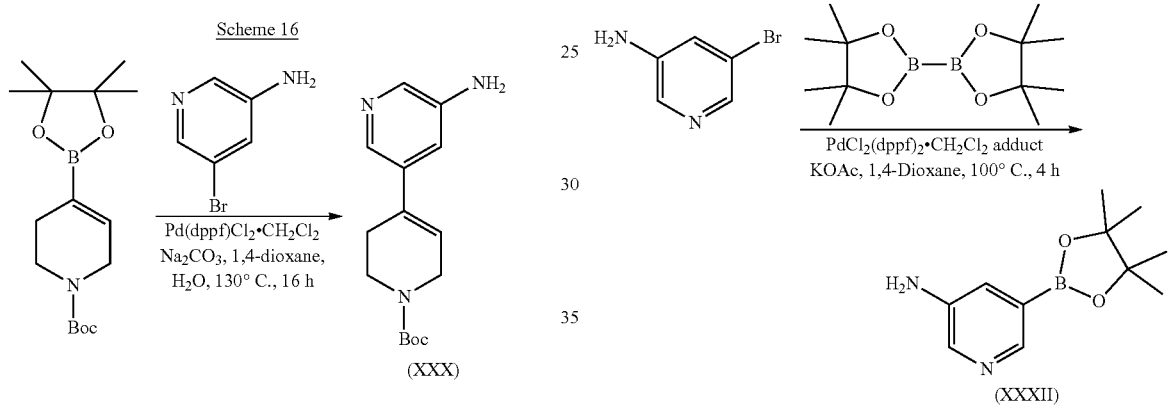

Methods of Use

In one aspect, the invention relates to a compound of Formula (I), or a pharmaceutically acceptable salt thereof, for use in therapy.

In one aspect, the invention relates to a compound of Formula (I), or a pharmaceutically acceptable salt thereof, for use in the treatment of a mycobacterial infection. A mycobacterial infection is one caused by infection with a *mycobacterium*.

The *mycobacterium* may be a member of one of the following groups of *mycobacterium*: *Mycobacterium tuberculosis* complex (MTC), *Mycobacterium avium* complex (MAC), *Mycobacterium gordonae* clade, *Mycobacterium kansasii* clade, *Mycobacterium chelonae* clade, *Mycobacterium fortuitum* clade, *Mycobacterium parafortuitum* clade or *Mycobacterium vaccae* clade. The *mycobacterium* may also be *Mycobacterium ulcerans* or *Mycobacterium leprae*.

In one embodiment, the *mycobacterium* is a member of the *Mycobacterium tuberculosis* complex (MTC).

Members of *Mycobacterium tuberculosis* complex (MTC) include *Mycobacterium tuberculosis*, *Mycobacterium africanum*, *Mycobacterium bovis*, *Mycobacterium bovis* BCG, *Mycobacterium* canetti, *Mycobacterium caprae*, *Mycobacterium microti* and *Mycobacterium pinnipedii*. These mycobacteria are causative agents of human and animal tuberculosis. *Mycobacterium tuberculosis* is the major cause of human tuberculosis.

In one embodiment, the infection is a *Mycobacterium tuberculosis* infection. In other words, the mycobacterial infection is caused by infection with *Mycobacterium tuberculosis*.

In one embodiment, the *Mycobacterium tuberculosis* is multidrug-resistant. In another embodiment the *Mycobacterium tuberculosis* is resistant to ethionamide.

Members of *Mycobacterium avium* complex (MAC) include *Mycobacterium avium*, *Mycobacterium avium* paratuberculosis, *Mycobacterium avium* silaticum, *Mycobacterium avium* hominissuis, *Mycobacterium* columbiense and *Mycobacterium indicus* pranii.

Members of *Mycobacterium gordonae* clade include *Mycobacterium asiaticum* and *Mycobacterium gordonae*.

Members of *Mycobacterium kansasii* clade include *Mycobacterium* gastri and *Mycobacterium kansasii*.

Members of *Mycobacterium chelonae* clade include *Mycobacterium abscessus*, *Mycobacterium bolletii* and *Mycobacterium chelonae*.

Members of *Mycobacterium fortuitum* clade include *Mycobacterium boenickei*, *Mycobacterium brisbanense*, *Mycobacterium cosmeticum*, *Mycobacterium fortuitum*, *Mycobacterium fortuitum* subspecies acetamidolyticum, *Mycobacterium houstonense*, *Mycobacterium mageritense*, *Mycobacterium neworleansense*, *Mycobacterium peregrinum*, *Mycobacterium porcinum*, *Mycobacterium senegalense* and *Mycobacterium septicum*.

Members of *Mycobacterium parafortuitum* clade include *Mycobacterium austroafricanum*, *Mycobacterium diernhoferi*, *Mycobacterium frederiksbergense*, *Mycobacterium hodleri*, *Mycobacterium neoaurum* and *Mycobacterium parafortuitum*.

Therefore, the mycobacterial infection may be caused by infection with a *mycobacterium* selected from the following: *Mycobacterium tuberculosis*, *Mycobacterium africanum*, *Mycobacterium bovis*, *Mycobacterium bovis* BCG, *Mycobacterium canetti*, *Mycobacterium caprae*, *Mycobacterium microti*, *Mycobacterium pinnipedii*, *Mycobacterium avium*, *Mycobacterium avium paratuberculosis*, *Mycobacterium avium silaticum*, *Mycobacterium avium hominissuis*, *Mycobacterium columbiense*, *Mycobacterium indicus pranii*, *Mycobacterium asiaticum*, *Mycobacterium gordonae*, *Mycobacterium gastri*, *Mycobacterium kansasii*, *Mycobacterium abscessus*, *Mycobacterium bolletii*, *Mycobacterium chelonae*, include *Mycobacterium boenickei*, *Mycobacterium brisbanense*, *Mycobacterium cosmeticum*, *Mycobacterium fortuitum*, *Mycobacterium fortuitum* subspecies acetamidolyticum, *Mycobacterium houstonense*, *Mycobacterium mageritense*, *Mycobacterium neworleansense*, *Mycobacterium peregrinum*, *Mycobacterium porcinum*, *Mycobacterium senegalense*, *Mycobacterium septicum*, *Mycobacterium austroafricanum*, *Mycobacterium diernhoferi*, *Mycobacterium frederiksbergense*, *Mycobacterium hodleri*, *Mycobacterium neoaurum*, *Mycobacterium parafortuitum*, *Mycobacterium ulcerans* and *Mycobacterium leprae*.

In another aspect, the invention relates to a compound of Formula (I), or a pharmaceutically acceptable salt thereof, for use in the treatment of a disease caused by infection with a *mycobacterium*, where the *mycobacterium* is selected from those hereinbefore described. Diseases caused by infection with a *mycobacterium* include, but are not limited to, tuberculosis (e.g. from *Mycobacterium tuberculosis*), leprosy (e.g. from *Mycobacterium leprae*), Johne's disease (e.g. from *Mycobacterium avium* subspecies paratuberculosis), Buruli or Bairnsdale ulcer (e.g. from *Mycobacterium ulceran*), Crohn's disease (e.g. from *Mycobacterium avium* subspecies paratuberculosis), pulmonary disease or pulmonary infection, pneumonia, bursa, synovial, tendon sheaths, localized abscess, lymphadenitis, skin and soft tissue infections, Lady Windermere syndrome (e.g. from *Mycobacterium avium* complex (MAC)), MAC lung disease, disseminated *Mycobacterium avium* complex (DMAC), disseminated *Mycobacterium avium intracellulare* complex (DMAIC), hot-tub lung (e.g. from *Mycobacterium avium* complex), MAC mastitis, MAC pyomyositis, or granuloma disease.

In one embodiment, the disease is tuberculosis. Thus, one aspect of the invention relates to a compound of Formula (I), or a pharmaceutically acceptable salt thereof, for use in the treatment of tuberculosis.

In another embodiment, the invention relates to a method of treatment of a mycobacterial infection in a mammal in need thereof, said treatment comprising administering to said mammal a therapeutically effective amount of a compound of Formula (I), or pharmaceutically acceptable salt thereof. As described herein, a mycobacterial infection is one caused by infection with a *mycobacterium*. The *mycobacterium* is as hereinbefore described.

In one embodiment, the invention relates to a method of treatment of a *Mycobacterium tuberculosis* infection.

In another embodiment, the invention relates to a method of treatment of a disease caused by infection with a *mycobacterium* in a mammal in need thereof, said treatment comprising administering to said mammal a therapeutically effective amount of a compound of Formula (I), or a pharmaceutically acceptable salt thereof.

In one embodiment, the disease is tuberculosis. Therefore, also described herein is a method of treatment of tuberculosis in a mammal in need thereof, said treatment comprising administering to said mammal a therapeutically effective amount of a compound of Formula (I), or a pharmaceutically acceptable salt thereof.

In one embodiment, the mammal is a human.

It will be appreciated by those skilled in the art that references herein to treatment refer to the treatment of established conditions. However, compounds of the invention may, depending on the condition, also be useful in the prevention of certain diseases. Thus, in one embodiment, there is provided the treatment or prevention of a disease such as TB. In another embodiment, there is provided the treatment of a disease such as TB. In a further embodiment, there is provided the prevention of a disease such as TB.

In another embodiment, the invention relates to use of a compound of Formula (I), or a pharmaceutically acceptable salt thereof, in the manufacture of a medicament for use in the treatment of a mycobacterial infection or in the treatment of a disease caused by infection with a *mycobacterium*.

Also described herein is the use of a compound of Formula (I), or a pharmaceutically acceptable salt thereof, in the manufacture of a medicament for use in the treatment of tuberculosis.

In one embodiment, a compound of Formula (I) of pharmaceutically acceptable salt thereof, for use in the treatment of TB, is co-administered with a thioamide. In a further embodiment, the thioamide is ethionamide. In an alternative embodiment, the thioamide is prothionamide.

Consequently, in one embodiment there is provided a pharmaceutical composition for use in the treatment of TB, wherein said composition comprises (a) a compound of Formula (I); (b) a thioamide, for example ethionamide or prothionamide; and optionally (c) a pharmaceutically acceptable excipient.

In another embodiment, the invention relates to a method of treatment of a mycobacterial infection in a mammal in need thereof, said treatment comprising administering to said mammal a therapeutically effective amount of a compound of Formula (I), or pharmaceutically acceptable salt thereof, in combination with a thioamide, wherein said thioamide may be ethionamide. In an alternative embodiment, the thioamide is prothionamide. As described herein, a mycobacterial infection is one caused by infection with a *mycobacterium*. The *mycobacterium* is as hereinbefore described.

In one embodiment, the mycobacterial infection is a *Mycobacterium tuberculosis* infection.

In another embodiment, the invention relates to a method of treatment of a disease caused by infection with a *mycobacterium* in a mammal in need thereof, said treatment comprising administering to said mammal a therapeutically effective amount of a compound of Formula (I), or a pharmaceutically acceptable salt thereof, in combination with a thioamide, wherein said thioamide may be ethionamide. In an alternative embodiment, the thioamide is prothionamide.

In one embodiment, the disease is tuberculosis. Therefore, also described herein is a method of treatment of tuberculosis in a mammal in need thereof, said treatment comprising administering to said mammal a therapeutically effective amount of a compound of Formula (I), or a pharmaceutically acceptable salt thereof, in combination with a thioamide, wherein said thioamide may be ethionamide. In an alternative embodiment, the thioamide is prothionamide.

In another embodiment, the invention relates to use of a compound of Formula (I), or a pharmaceutically acceptable salt thereof, in combination with a thioamide (for example, ethionamide), in the manufacture of a medicament for use in the treatment of a mycobacterial infection or in the treatment of a disease caused by infection with a *mycobacterium*. In an alternative embodiment, the thioamide is prothionamide.

Also described herein is the use of a compound of Formula (I), or a pharmaceutically acceptable salt thereof, in combination with a thioamide (for example, ethionamide) in the manufacture of a medicament for use in the treatment of tuberculosis. In an alternative embodiment, the thioamide is prothionamide.

In an embodiment, the compound of Formula (I) for use in the above described methods and treatments is 4,4,4-trifluoro-1-(4-(2-(trifluoromethyl)pyridin-4-yl)piperidin-1-yl)butan-1-one having the following structure:

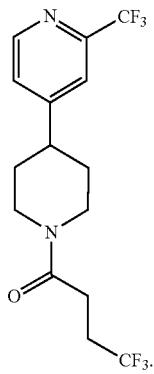 [SMILES: O=C(CCC(F)(F)F)N1CCC(c2ccnc(C(F)(F)F)c2)CC1]

Pharmaceutical Compositions

The compounds of Formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of Formula (I), or a pharmaceutically acceptable salt thereof, and a pharmaceutically acceptable excipient.

Pharmaceutical compositions may be administered by any appropriate route, for example by the oral (including buccal or sublingual), rectal, inhaled, intranasal, topical (including buccal, sublingual or transdermal) or parenteral (including subcutaneous, intramuscular, intravenous or intradermal) route. In particular, pharmaceutical compositions of the invention may be administered by oral or intravenous route.

Suitable pharmaceutically acceptable excipients include the following types of excipients: carriers, diluents, fillers, binders, disintegrants, lubricants, glidants, granulating agents, coating agents, wetting agents, solvents, co-solvents, suspending agents, emulsifiers, sweeteners, flavouring agents, flavour-masking agents, colouring agents, anti-caking agents, humectants, chelating agents, plasticisers, viscosity increasing agents, antioxidants, preservatives, stabilisers, surfactants and buffering agents.

Suitable methods for formulating compounds of the invention will be familiar to those skilled in the art, which are described in Remington: The Science and Practice of Pharmacy, 21$^{st}$ Edition 2006.

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

When the compounds of the invention or pharmaceutically acceptable salts thereof are used in the treatment of tuberculosis, they may be employed alone or in combination with a further therapeutic agent, such as a further antimycobacterial agent, for example an anti-tuberculosis agent and/or antiviral agent, including antiretroviral agents.

For example, the present invention relates to compounds of Formula (I) or pharmaceutically acceptable salts thereof, in combination with a further anti-tuberculosis agent. In an embodiment, the combination comprises two, three, four, five, six or seven additional anti-tuberculosis agents. For example, in the treatment of multidrug-resistant tuberculosis, it is common that combinations of four or more drugs are administered to patients. For example, in the treatment of drug-sensitive tuberculosis, it is common that combinations of three or four drugs are administered to patients.

The further anti-tuberculosis agent is an agent in development, approved or recommended for the treatment of tuberculosis and may be selected from isoniazid, rifampin, pyrazinamide, ethambutol, moxifloxacin, rifapentine, clofazimine, ethionamide, prothionamide, isoxyl, thiacetazone, rifabutin, a diarylquinoline such as bedaquiline (TMC207) or TBAJ-587, nitroimidazo-oxazine PA-824, delamanid (OPC-67683), an oxazolidinone such as linezolid, tedizolid, radezolid, sutezolid (PNU-100480), posizolid (AZD-5847) or TBI-223, EMB analogue SQ109, OPC-167832, GSK3036656 (also known as GSK070), GSK2556286, GSK3211830, a benzothiazinone such as BTZ043 or PBTZ169, an azaindole such as TBA-7371, a dinitrobenzamide, or a beta-lactam such as meropenem, faropenem, ertapenem, tebipenem or beta-lactam combinations such as AUGMENTIN (amoxicillin-clavulanate).

In an embodiment, the anti-tuberculosis agent may be selected from isoniazid, rifampin, pyrazinamide, ethambutol, moxifloxacin, rifapentine, clofazimine, ethionamide, prothionamide, isoxyl, thiazetazone, bedaquiline (TMC207), nitroimidazo-oxazine PA-824, delamanid (OPC-67683), an oxazolidinone such as linezolid, tedizolid, radezolid, sutezolid (PNU-100480), or posizolid (AZD-5847), EMB analogue SQ109, OPC-167832, GSK3036656A (also known as GSK070), GSK2556286, GSK3211830 and a benzothiazinone or a dinitrobenzamide.

A combination according to the present invention may further comprise an antiviral agent, including an antitretroviral agent.

Such antiretroviral agents may be selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir and darunavir.

A compound of the invention (i.e. a compound of Formula (I) or pharmaceutically acceptable salt thereof) may be used in combination with an anti-tuberculosis agent that is activatable via the EthA pathway. A person skilled in the art is able to determine if a particular compound is activatable via the EthA pathway, for example, by applying the method described in the following publication: "Activation of the prodrug ethionamide is regulated by mycobacteria" A. R. Baulard et al., Journal of Biological Chemistry, 2000, pages 28326-28331.

More particularly, the anti-tuberculosis agent may be chosen from the thioamide family, such as ethionamide, prothionamide, isoxyl and thiazetazone.

In one embodiment, a compound of the invention (i.e. a compound of Formula (I) or pharmaceutically acceptable salt thereof) is used in combination with ethionamide. In this embodiment, the compounds of the invention (i.e. a compound of Formula (I) or pharmaceutically acceptable salt thereof) have shown to potentiate the activity of ethionamide.

The combinations may conveniently be presented for use in the form of a pharmaceutical composition or formulation. Therefore, also contemplated herein is a pharmaceutical composition comprising (a) a compound of the invention (i.e. a compound of Formula (I) or pharmaceutically acceptable salt thereof), as herein described, together with (b) one or more pharmaceutically acceptable carriers as herein described, and (c) at least one other anti-tuberculosis drug and (d) optionally an antiviral agent including antiretroviral agents.

A compound of the invention (i.e. a compound of Formula (I) or pharmaceutically acceptable salt thereof) and further therapeutic agent may be administered together or separately and, when administered separately, this may occur separately or sequentially in any order (by the same or by different routes of administration). The amount of a compound of the invention (i.e. compound of Formula (I) or pharmaceutically acceptable salt thereof) and the further therapeutically active agent(s) and the relative timings of administration will be selected in order to achieve the desired combined therapeutic effect.

EXAMPLES

The invention will now be illustrated by way of the following non-limiting examples. While particular embodiments of the invention are described below a skilled person will appreciate that various changes and modifications can be made. References to preparations carried out in a similar manner to, or by the general method of, other preparations, may encompass variations in routine parameters such as time, temperature, workup conditions, minor changes in reagents amounts, etc.

Abbreviations

The following list provides definitions of certain abbreviations and symbols as used herein. It will be appreciated that the list is not exhaustive, but the meaning of those abbreviations and symbols not herein below defined will be readily apparent to those skilled in the art. In describing the invention, chemical elements are identified in accordance with the Periodic Table of the Elements.

ACN/MeCN Acetonitrile
anh Anhydrous
aq. Aqueous
$CDCl_3$ Deuterated chlorofom
$CD_2Cl_2$ Deuterated dichloromethane
CyHex Cyclohexane
DAST Diethylaminosulfur trifluoride
DCM Dichloromethane
DIPEA Diisopropylethylamine
DMAP 4-Dimethylaminopyridine
DME Dimethoxyethane
DMF Dimethylformamide
DMSO-d$_6$ Deuterated dimethylsulfoxide
dppf 1,1'-Bis(diphenylphosphino)ferrocene
EDC.HCl N-(3-Dimethylaminopropyl)-N'-ethylcarbodiimide hydrochloride
EtOAc Ethyl acetate
EtOH Ethanol
HBTU N,N,N',N'-Tetramethyl-O-(1H-benzotriazol-1-yl)uronium hexafluorophosphate
HOBt 1-Hydroxybenzotriazole hydrate
HPLC High Performance Liquid Chromatography
Int. Intermediate
M Molar
MeOH Methanol
MS Mass spectroscopy
min Minutes
N Normal
NaH Sodium hydride
NaHMDS Sodium bis(trimethylsilyl)amide
NMR Nuclear Magnetic Resonance
pet Petroleum
Ref. Ex. Reference Example
rt Room temperature
TFA Trifluoroacetic acid
TEA Triethylamine
THF Tetrahydrofuran Proton nuclear magnetic resonance ($^1$H NMR) spectra were recorded, and chemical shifts are reported in parts per million (δ) downfield from the internal standard tetramethylsilane (TMS). Abbreviations for NMR data are as follows:

s=singlet, d=doublet, t=triplet, q=quartet, m=multiplet, app=apparent, br=broad. Mass spectra were obtained using electrospray (ES) ionization techniques. All temperatures are reported in degrees centigrade.

In certain of the following Intermediates and Examples, starting materials are identified by reference to other Intermediate or Example numbers. This does not signify that the actual material from any particular Intermediate or Example was necessarily used in a subsequent step exemplified herein, but is used as a short-hand means of denoting the relevant compound name.

Intermediates

Intermediate 1: 1-(benzotriazol-1-yl)-4,4,4-trifluoro-butan-1-one

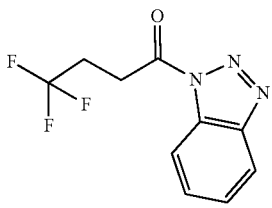 [SMILES: O=C(CCC(F)(F)F)n1nnc2ccccc21]

Thionyl chloride (SIGMA-ALDRICH, 6.74 mL, 93 mmol) and 1H-benzotriazole (ALFA-AESAR, 31.2 g, 262 mmol) in DCM (150 mL) were added dropwise to a solution of 4,4,4-trifluorobutanoic acid (FLUOROCHEM, 12 g, 85 mmol) in DCM (150 mL). The reaction mixture was stirred at rt 12 h. The precipitate was filtered off and the filtrate was dried in vacuo to yield title compound (19.6 g, 94%) as an off-white solid. $^1$H NMR (300 MHz, CD$_2$Cl$_2$) δ ppm: 8.28 (d, J=8.3 Hz, 1H), 8.15 (d, J=8.4 Hz, 1H), 7.75-7.69 (m, 1H), 7.60-7.54 (m, 1H), 3.77 (t, J=7.8 Hz, 2H), 2.91-2.73 (m, 2H). [ES+MS] m/z 244 (MH$^+$).

Intermediate 2: 1-(4,4,4-trifluorobutanoyl)piperidin-4-one

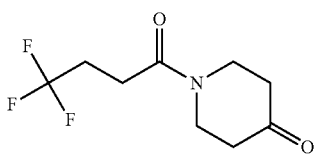

To a solution of piperidin-4-one hydrate hydrochloride (SIGMA-ALDRICH, 7.05 g, 45.9 mmol) and 4-DMAP (SIGMA-ALDRICH, 5.6 g, 45.84 mmol) in chloroform (16 mL) was added Intermediate 1 (10.0 g, 41.12 mmol). The solution was exposed to microwave irradiation for 15 min at 100° C. The reaction mixture was washed with a saturated solution of Na$_2$CO$_3$ (three times) and a 1M aqueous solution of HCl. The organic layer was washed with brine, dried over (anh) MgSO$_4$ and evaporated to give title compound 1-(4,4,4-trifluorobutanoyl)piperidin-4-one (4.63 g, 49.2%) as an orange oil. $^1$H NMR (300 MHz, CD$_2$Cl$_2$) δ ppm: 3.86 (t, J=6.4 Hz, 2H), 3.73 (t, J=6.3 Hz, 2H), 2.69-2.61 (m, 2H), 2.58-2.42 (m, 6H). [ES+MS] m/z 224 (MH$^+$).

Intermediate 3: 4-methoxy-N-[[1-(4,4,4-trifluorobutanoyl)-4-piperidylidene]amino]benzene sulfonamide

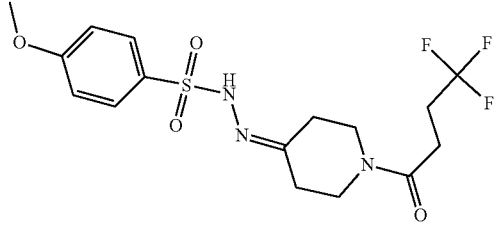 [SMILES: COc1ccc(S(=O)(=O)NN=C2CCN(C(=O)CCC(F)(F)F)CC2)cc1]

To a solution of 4-methoxybenzenesulfonohydrazide (prepared according to the method set out in J. Org. Chem. 2014, p328-338) (4.2 g, 20.77 mmol) in MeOH (90 mL) was added Intermediate 2 (4.63 g, 20.74 mmol). The reaction mixture was stirred at rt for 3 days. Solvents were removed in vacuo to give of title compound (8.39 g, 96.1%) as a white solid. $^1$H NMR (300 MHz, CD$_2$Cl$_2$) δ ppm: 7.87-7.81 (m, 2H), 7.25-7.20 (m, 1H), 7.03-6.98 (m, 2H), 3.87 (s, 3H), 3.73-3.62 (m, 2H), 3.58-3.53 (m, 2H), 2.60-2.31 (m, 8H). [ES+MS] m/z 408 (MH$^+$).

Intermediate 4: tert-butyl 4-(6-fluoro-3-pyridyl)-3,6-dihydro-2H-pyridine-1-carboxylate

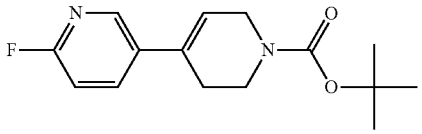 [SMILES: CC(C)(C)OC(=O)N1CC=C(c2ccc(F)nc2)CC1]

Tert-butyl 4-(4,4,5,5-tetramethyl-1,3,2-dioxaborolan-2-yl)-3,6-dihydro-2H-pyridine-1-carboxylate (ENAMINE, 1.01 g, 3.27 mmol), 5-bromo-2-fluoro-pyridine (ALFA-AESAR, 0.33 mL, 3.23 mmol) and K2003 (SIGMA-ALDRICH, 903.5 mg, 6.54 mmol) were suspended in a mixture of DME/MeOH/H$_2$O (2/1/2, 5 mL) under inert atmosphere. Then Pd(dppf)Cl$_2$ (ACROS, 264.2 mg, 0.32 mmol) was added under argon and the sealed tube was submitted to microwave irradiation at 90° C. for 15 min. Water was added to the reaction mixture which was extracted with EtOAc (×2). The organic layer was washed with brine, dried over (anh) MgSO$_4$ and evaporated to give 1.45 g of crude as a purple oil. The residue was purified on silica gel using a linear gradient of DCM/MeOH as eluents to give unclean brown oil. The residue was then purified by preparative HPLC (OmniSpher C18 column, 10µ, 41×250 mm) gradient 30 min 10% to 100% ACN/H$_2$O (0.1% formic acid) to give the title compound (587.1 mg, 53.7%) as an orange oil. [ES+MS] m/z 279 (MH$^+$).

Intermediates 5-15 were prepared by methods analogous to that described for Intermediate 4 but replacing the 5-bromo-2-fluoro-pyridine with that indicated in Table 1. Modifications in the purification step are also indicated.

TABLE 1

| Int. | Structure | Starting material | Physical data |
| --- | --- | --- | --- |
| 5 | (see footnote a) | FLUOROCHEM | $^1$H NMR (300 MHz, CD$_2$Cl$_2$) δ ppm: 8.75 (d, J = 2.0 Hz, 1H), 7.84-7.81 (m, 1H), 7.65 (d, J = 8.2 Hz, 1H), 6.28-6.18 (m, 1H), 4.10 (q, J = 3.0 Hz, 2H), 3.65 (t, J = 5.7 Hz, 2H), 2.51-2.55 (m, 2H), 1.47 (s, 9H). [ES + MS] m/z 329 (MH$^+$). |
| 6 | (see footnote a) | | $^1$H NMR (300 MHz, CD$_2$Cl$_2$) δ ppm: 8.73-8.72 (m, 1H), 7.65-7.55 (m, 1H), 7.38-7.36 (m, 1H), 6.75-6.73 (m, 1H), 4.15-4.12 (m, 2H), 3.64 (t, J = 5.7 Hz, 2H), 2.67-2.61 (m, 2H), 1.47 (s, 9H). [ES + MS] m/z 329 (MH$^+$). |
| 7 | (see footnote a) | FLUOROCHEM | $^1$H NMR (300 MHz, CD$_2$Cl$_2$) δ ppm: 8.83-8.74 (m, 2H), 7.89-7.87 (m, 1H), 6.26-6.16 (m, 1H), 4.09 (q, J = 3.0 Hz, 2H), 3.65 (t, J = 3.0 Hz, 2H), 2.56-2.51 (m, 2H), 1.14 (s, 9H). [ES + MS] m/z 329 (MH$^+$). |
| 8 | (see footnote a) | FLUOROCHEM | $^1$H NMR (300 MHz, CD$_2$Cl$_2$) δ ppm: 7.88-7.82 (m, 1H), 7.60-7.52 (m, 2H), 6.76-6.72 (m, 1H), 4.13 (q, J = 3.0 Hz, 2H), 3.64 (t, J = 5.7 Hz, 2H), 2.68-2.62 (m, 2H), 1.47 (s, 9H). [ES + MS] m/z 329 (MH$^+$). |
| 9 | (see footnote a) | | $^1$H NMR (300 MHz, CD$_2$Cl$_2$) δ ppm: 7.80-7.72 (m, 1H), 7.27-7.24 (m, 1H), 6.81-6.77 (m, 1H), 6.73-6.69 (m, 1H), 4.12-4.09 (m, 2H), 3.61 (t, J = 5.7 Hz, 2H), 2.59-2.53 (m, 2H), 1.46 (s, 9H). [ES + MS] m/z 279 (MH$^+$). |
| 10 | (see footnote a) | | $^1$H NMR (300 MHz, CD$_2$Cl$_2$) δ ppm: 8.16 (d, J = 2.4 Hz, 1H), 7.63-7.60 (m, 1H), 6.71-6.68 (m, 1H), 5.99-5.95 (m, 1H), 4.05-4.02 (m, 2H), 3.90 (s, 3H), 3.61 (t, J = 5.7 Hz, 2H), 2.49-2.45 (m, 2H), 1.46 (s, 9H). [ES + MS] m/z 291 (MH$^+$). |
| 11 | (see footnote a) | MATRIX SCIENTIFIC | $^1$H NMR (300 MHz, CD$_2$Cl$_2$) δ ppm: 8.61-8.59 (m, 1H), 7.63-7.60 (m, 1H), 7.49-7.45 (m, 1H), 5.68-5.58 (m, 1H), 4.02 (q, J = 2.9 Hz, 2H), 3.61 (t, J = 5.6 Hz, 2H), 2.35-2.33 (m, 2H), 1.47 (s, 9H). [ES + MS] m/z 329 (MH$^+$). |

TABLE 1-continued

| Int. | Structure | Starting material | Physical data |
|---|---|---|---|
| 12 | see footnote a) | FLUOROCHEM | $^1$H NMR (300 MHz, CD$_2$Cl$_2$) δ ppm: 8.24 (d, J = 1.4 Hz, 1H), 8.17 (d, J = 2.6 Hz, 1H), 7.17-7.15 (m, 1H), 6.16-6.06 (m, 1H), 4.08-4.05 (m, 2H), 3.86 (s, 3H), 3.62 (t, J = 5.7 Hz, 2H), 2.52-2.48 (m, 2H), 1.46 (s, 9H). [ES + MS] m/z 291 (MH$^+$). |
| 13 | see footnote a) | FLUOROCHEM | $^1$H NMR (300 MHz, CD$_2$Cl$_2$) δ ppm: 8.31-8.29 (m, 1H), 7.26-7.19 (m, 1H), 6.53-6.40 (m, 1H), 4.10 (q, J = 3.0 Hz, 2H), 3.60 (t, J = 5.7 Hz, 2H), 2.66-2.61 (m, 2H), 1.46 (s, 9H). [ES + MS] m/z 297 (MH$^+$). |
| 14 | see footnote a) | FLUOROCHEM | $^1$H NMR (300 MHz, CD$_2$Cl$_2$) δ ppm: 7.84-7.75 (m, 1H), 6.85-6.81 (m, 1H), 6.05-5.95 (m, 1H), 4.08-4.04 (m, 2H), 3.60 (t, J = 5.7 Hz, 2H), 2.47-2.43 (m, 2H), 1.46 (s, 9H). [ES + MS] m/z 297 (MH$^+$). |
| 15 | see footnote a) | | $^1$H NMR (300 MHz, CD$_2$Cl$_2$) δ ppm: 8.94 (d, J = 4.9 Hz, 1H), 7.44 (d, J = 4.9 Hz, 1H), 7.39-7.29 (m, 1H), 4.20-4.16 (m, 2H), 3.62 (t, J = 5.7 Hz, 2H), 2.74-2.68 (m, 2H), 1.47 (s, 9H). [ES + MS] m/z 330 (MH$^+$). | a) purification on silica gel using a linear gradient of DCM/MeOH.

Intermediate 16: 4,4,4-trifluoro-1-[4-(6-fluoro-3-pyridyl)-3,6-dihydro-2H-pyridin-1-yl]butan-1-one

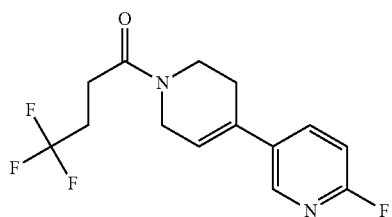 [SMILES: O=C(CCC(F)(F)F)N1CC=C(c2ccc(F)nc2)CC1]

To a solution of Intermediate 4 (587.1 mg, 1.76 mmol) in DCM (9 mL) was added dropwise a 4M solution of HCl in dioxane (SIGMA-ALDRICH, 5.27 mL, 12 eq) at rt. Then the reaction mixture was stirred overnight and solvent was evaporated to give 519.4 mg of 2-fluoro-5-(1,2,3,6-tetrahydropyridin-4-yl)pyridine hydrochloride as an orange solid which was dried under vacuum. Chloroform (4.6 mL), DMAP (SIGMA-ALDRICH, 305.8 mg, 2.5 mmol) and Intermediate 1, (547.6 mg, 2.25 mmol) were added to the orange residue and the solution was exposed to microwave irradiation for 15 min at 100° C. The reaction mixture was washed with a saturated solution of Na$_2$CO$_3$ (three times) and a 1M aqueous solution of HCl. The organic layer was washed with brine, dried over (anh) MgSO$_4$ and evaporated. The residue was purified by preparative HPLC (OmniSpher C18 column, 10μ, 41×250 mm) gradient 30 min 10% to 100% ACN/H$_2$O (0.1% formic acid) to give title compound 4,4,4-trifluoro-1-[4-(6-fluoro-3-pyridyl)-3,6-dihydro-2H-pyridin-1-yl]butan-1-one (121.0 mg, 17.8%) as a white solid. $^1$H NMR (300 MHz, CD$_2$Cl$_2$) δ ppm: 8.22-8.20 (m, 1H), 7.82-7.76 (m, 1H), 6.94-6.90 (m, 1H), 6.13-6.03 (m, 1H), 4.24-4.21 (m, 1H), 4.14-4.11 (m, 1H), 3.82 (t, J=5.8 Hz, 1H), 3.67 (t, J=5.8 Hz, 1H), 2.68-2.49 (m, 6H), 1.53 (s, 9H). [ES+MS] m/z 303 (MH$^+$).

Intermediate 16 was also prepared by method described in Table 3.

Intermediates 17-27 were prepared by methods analogous to that described for Intermediate 16 but replacing Intermediate 4 with that indicated in Table 2. Modifications in the purification step are also indicated.

TABLE 2

| Int. | Structure | Starting Int. | Physical data |
|---|---|---|---|
| 17 | (structure: 4,4,4-trifluorobutanoyl-tetrahydropyridine linked to 2-(trifluoromethyl)pyridin-5-yl) See footnote a) | 5 | $^1$H NMR (300 MHz, CD$_2$Cl$_2$) δ ppm: 8.76-8.74 (m, 1H), 7.85-7.82 (m, 1H), 7.66 (d, J = 8.1 Hz, 1H), 6.30-6.20 (m, 1H), 4.27 (q, J = 2.9 Hz, 1H), 4.17 (q, J = 2.9 Hz, 1H), 3.84 (t, J = 5.7 Hz, 1H), 3.70 (t, J = 5.7 Hz, 1H), 2.69-2.46 (m, 6H). [ES + MS] m/z 353 (MH$^+$). |
| 18 | (structure: 4,4,4-trifluorobutanoyl-tetrahydropyridine linked to 4-(trifluoromethyl)pyridin-2-yl) See footnote a) | 6 | [ES + MS] m/z 353 (MH$^+$). |
| 19 | (structure: 4,4,4-trifluorobutanoyl-tetrahydropyridine linked to 5-(trifluoromethyl)pyridin-3-yl) See footnote a) | 7 | $^1$H NMR (300 MHz, CD$_2$Cl$_2$) δ ppm: 8.83-8.77 (m, 2H), 7.90-7.87 (m, 1H), 6.28-6.18 (m, 1H), 4.26 (q, J = 2.9 Hz, 1H), 4.16 (q, J = 2.9 Hz, 1H), 3.84 (t, J = 5.7 Hz, 1H), 3.70 (t, J = 5.7 Hz, 1H), 2.69-2.46 (m, 6H). [ES + MS] m/z 353 (MH$^+$). |
| 20 | (structure: 4,4,4-trifluorobutanoyl-tetrahydropyridine linked to 6-(trifluoromethyl)pyridin-2-yl) See footnote a) | 8 | $^1$H NMR (300 MHz, CD$_2$Cl$_2$) δ ppm: 7.91-7.84 (m, 1H), 7.64-7.54 (m, 2H), 6.79-6.72 (m, 1H), 4.30 (q, J = 3.0 Hz, 1H), 4.20 (q, J = 3.0 Hz, 1H), 3.84 (t, J = 5.8 Hz, 1H), 3.68 (t, J = 5.8 Hz, 1H), 2.78-2.45 (m, 6H). [ES + MS] m/z 353 (MH$^+$). |
| 21 | (structure: 4,4,4-trifluorobutanoyl-tetrahydropyridine linked to 6-fluoropyridin-2-yl) See footnote a) | 9 | $^1$H NMR (300 MHz, CD$_2$Cl$_2$) δ ppm: 7.77-7.75 (m, 1H), 7.27-7.25 (m, 1H), 6.80-6.70 (m, 2H), 4.24-4.16 (m, 2H), 3.79-3.62 (m, 2H), 2.63-2.53 (m, 2H). [ES + MS] m/z 303 (MH$^+$). |

TABLE 2-continued

| Int. | Structure | Starting Int. | Physical data |
|---|---|---|---|
| 22 | See footnote a) | 10 | [ES + MS] m/z 315 (MH⁺). |
| 23 | See footnote a) | 11 | [ES + MS] m/z 353 (MH⁺). |
| 24 | See footnote b) | 12 | ¹H NMR (300 MHz, CD$_2$Cl$_2$) δ ppm: 8.26-8.24 (m, 1H), 8.19-8.18 (m, 1H), 7.17-7.16 (m, 1H), 6.18-6.09 (m, 1H), 4.25-4.22 (m, 1H), 4.15-4.12 (m, 1H), 3.87 (s, 3H), 3.82 (t, J = 5.7 Hz, 1H), 3.67 (t, J = 5.7 Hz, 1H), 2.69-2.45 (m, 6H). [ES + MS] m/z 315 (MH⁺). |
| 25 | See footnote b) | 13 | ¹H NMR (300 MHz, CD$_2$Cl$_2$) δ ppm: 8.32-8.30 (m, 1H), 7.29-7.19 (m, 1H), 6.55-6.49 (m, 1H), 4.28-4.25 (m, 1H), 4.18-4.16 (m, 1H), 3.80 (t, J = 5.7 Hz, 1H), 3.65 (t, J = 5.7 Hz, 1H), 2.76-2.72 (m, 1H), 2.69-2.44 (m, 5H). [ES + MS] m/z 321 (MH⁺). |
| 26 | See footnote b) | 14 | ¹H NMR (300 MHz, CD$_2$Cl$_2$) δ ppm: 7.84-7.76 (m, 1H), 6.87-6.83 (m, 1H), 6.06-6.00 (m, 1H), 4.27-4.21 (m, 1H), 4.14-4.11 (m, 1H), 3.80 (t, J = 5.7 Hz, 1H), 3.65 (t, J = 5.7 Hz, 1H), 2.68-2.45 (m, 6H). [ES + MS] m/z 321 (MH⁺). |

TABLE 2-continued

| Int. | Structure | Starting Int. | Physical data |
|---|---|---|---|
| 27 | 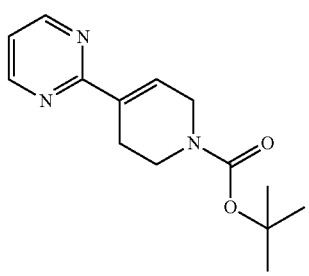 See footnote b) | 15 | [ES + MS] m/z 354 (MH⁺). | a) Preparative HPLC (OmniSpher C18 column, 10 μ, 41 × 250 mm) gradient 30 min 10% to 100% ACN/H₂O (0.1% formic acid)
b) Preparative HPLC (OmniSpher C18 column, 10 μ, 41 × 250 mm) gradient 35 min 10% to 100% ACN/H₂O (0.1% formic acid)

Intermediate 28: tert-butyl 4-(pyrimidin-2-yl)-1,2,3,6-tetrahydropyridine-1-carboxylate Tetrakis(triphenylphosphine)palladium(0) (ALFA-AESAR, 148 mg, 0.128 mmol) was added to a suspension of tert-butyl 4-(4,4,5,5-tetramethyl-1,3,2-dioxaborolan-2-yl)-5,6-dihydropyridine-1(2H)-carboxylate (ALFA-AESAR, 381 mg, 1.23 mmol), 2-bromopyrimidine (ALFA-AESAR, 195 mg, 1.23 mmol) and potassium carbonate (ALFA-AESAR, 351 mg, 2.54 mmol) in DME/EtOH/H₂O 2:1:2 (5 mL). The mixture was heated overnight at 90° C. UPLC-MS showed complete conversion of starting materials. The reaction mixture was diluted with water and extrated with EtOAc. Combined organic layers were dried over (anh) Na₂SO₄, filtered and concentrated under reduced pressure to give crude reaction mixture. The residue was purified by flash chromatography on silica gel using a linear gradient of CyHex/EtOAc as eluents to yield title compound. ¹H NMR (400 MHz, DMSO-d₆) δ ppm: 8.80 (d, J=4.8 Hz, 2H), 7.36 (t, J=4.8 Hz, 1H), 7.19 (br s, 1H), 4.16-4.05 (m, 2H), 3.55 (t, J=5.6 Hz, 2H), 2.66-2.57 (m, 2H), 1.45 (s, 9H). ES+MS] m/z 262 (MH⁺).

Intermediate 29: tert-butyl 4-(pyrimidin-2-yl)piperidine-1-carboxylate

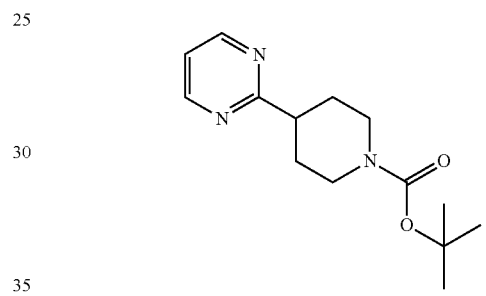

Intermediate 28 (400 mg, 1.53 mmol) was dissolved in EtOH (30 mL), then 10% Pd/C (ALFA-AESAR, 80 mg) was added and the mixture was stirred under H₂ at ambient pressure for 1 h. Monitoring by UPLC showed the complete consumption of the starting material. The catalyst was removed by filtration and the solvent evaporated to give the crude, which was purified by flash chromatography on silica gel using a linear gradient of CyHex/AcOEt as eluents to afford title compound (336.8 mg, 84%) as a white solid. ¹H NMR (400 MHz, DMSO-d₆) δ ppm: 8.76 (d, J=4.8 Hz, 2H), 7.35 (t, J=4.8 Hz, 1H), 4.02 (br d, J=12.3 Hz, 2H), 3.06-2.96 (m, 1H), 2.88 (br s, 2H), 1.97-1.86 (m, 2H), 1.68-1.59 (m, 2H), 1.45 (s, 9H).

Intermediate 30: 2-(piperidin-4-yl)pyrimidine Hydrochloride

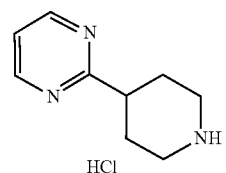 [SMILES: c1cnc(C2CCNCC2)nc1 ; Cl]

To a solution of Intermediate 29 (337 mg, 1.28 mmol) in 1,4-dioxane (3.2 mL), at 0° C. a solution of HCl 4M in 1,4-dioxane (ALFA-AESAR, 3.2 mL, 12.8 mmol) was added and the mixture was stirred at rt overnight. Monitoring by UPLC and TLC showed the reaction was completed. The solvent was removed under vacuum to afford title compound (295 mg, quantitative), which was used in the next step without further purification. ¹H NMR (400 MHz, DMSO-$d_6$) δ ppm: 9.12 (br s, 5H), 8.88 (br s, 4H), 8.79 (d, J=5.0 Hz, 7H), 7.40 (t, J=4.9 Hz, 4H), 3.38-3.28 (m, 2H), 3.21-3.11 (m, 1H), 3.09-2.97 (m, 2H), 2.17-2.08 (m, 2H), 2.05-1.92 (m, 2H). [ES+MS] m/z 164 (MH$^+$).

Intermediate 31: 4-(4,4,5,5-tetramethyl-1,3,2-dioxaborolan-2-yl)-1,2,3,6-tetrahydropyridine Hydrochloride (Commercially Available)

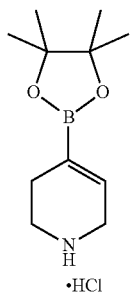

Tert-butyl 4-(4,4,5,5-tetramethyl-1,3,2-dioxaborolan-2-yl)-5,6-dihydropyridine-1(2H)-carboxylate (ARK PHARMA, 25 g, 80.851 mmol) was dissolved in 250 mL of EtOAc and HCl 4N in EtOAc (SYMAX FINE CHEMICALS, 250 mL) was added at 0° C. The mixture was allowed to 26° C. and stirred for 3 h. The reaction mixture was evaporated under reduced pressure. The crude was washed with diethyl ether and filtered to give title compound (20 g, quantitative). ¹H NMR (400 MHz, DMSO-$d_6$) δ ppm: 9.30 (br s, 2H), 6.40-6.30 (m, 1H), 3.64-3.52 (m, 2H), 3.15-3.00 (m, 2H), 2.34-2.22 (m, 2H), 1.21 (s, 12H).

Intermediate 32: 4,4,4-trifluoro-1-(4-(4,4,5,5-tetramethyl-1,3,2-dioxaborolan-2-yl)-5,6-dihydropyridin-1(2H)-yl)butan-1-one

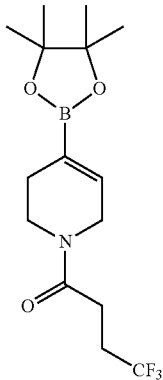 [SMILES: CC1(C)OB(C2=CCN(C(=O)CCC(F)(F)F)CC2)OC1(C)C]

To a solution of Intermediate 31 (750 mg, 3.0 mmol), 4,4,4-trifluorobutanoic acid (COMBIBLOCKS, 477 mg, 3.36 mmol) in DMF (10 mL) were added DMAP (AVRA, 1117 mg, 9.162 mmol) and EDC.HCl (SILVERY CHEMICALS, 1458 mg, 7.63 mmol) at 0° C. The reaction mixture was allowed to 27° C. and stirred for 16 h. The reaction mixture was quenched with ice cold water (100 mL) and extracted with EtOAc (3×30 mL). The organic layer was washed with brine (30 mL), dried over (anh) Na2SO4, filtered and the filtrate was evaporated under reduced pressure. The crude was purified by silica chromatography column using a linear gradient of petroleum ether/EtOAc as eluents to yield the title compound (410 mg, 41%) as a colorless liquid. 1H NMR (400 MHz, CDCl3) δ ppm: 6.55-6.40 (m, 1H), 4.15-3.96 (m, 2H), 3.69-3.43 (m, 2H), 2.63-2.42 (m, 4H), 2.35-2.22 (m, 2H), 1.31-1.22 (m, 12H). [ES+MS] m/z 332 (MH$^-$).

Intermediate 33: 4,4,4-trifluoro-1-(4-pyrimidin-5-yl-3,6-dihydro-2H-pyridin-1-yl)butan-1-one

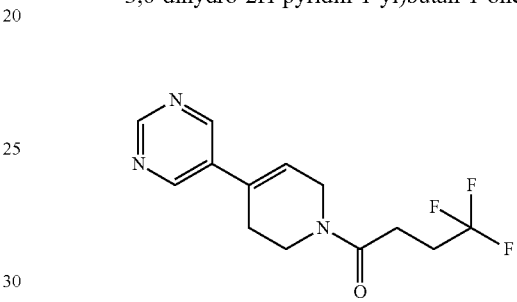

Intermediate 32 (400 mg, 1.2 mmol), 5-bromopyrimidine (ALFA-AESAR, 191 mg, 1.2 mmol) and K2CO$_3$ (SIGMA-ALDRICH, 332 mg, 2.4 mmol) were suspended in a mixture of DME/MeOH/H$_2$O (1/0.5/1, 2.5 mL) under inert atmosphere. Pd(dppf)Cl$_2$ (ACROS, 88 mg, 0.12 mmol) was added under argon and the sealed tube was submitted to microwave irradiation at 90° C. for 15 min. Water was added to the reaction mixture which was extracted with EtOAc (×2). The organic layer was washed with brine, dried over (anh) MgSO$_4$ and evaporated. The residue was purified by preparative HPLC (OmniSpher C18 column, 10µ,41×250 mm) gradient 30 min 10% to 100% ACN/H$_2$O (0.1% formic acid) to give title compound (160 mg, 46.7%) as a pale yellow oil. ¹H NMR (300 MHz, CD$_2$Cl$_2$) δ ppm: 9.05 (s, 1H), 8.74 (s, 2H), 6.25-6.19 (m, 1H), 4.26 (d, J=3.6 Hz, 1H), 4.18 (d, J=3.6 Hz, 1H), 3.84 (t, J=5.8 Hz, 1H), 3.71 (t, J=5.8 Hz, 1H), 2.69-2.55 (m, 6H). [ES+MS] m/z 286 (MH$^+$).

Intermediates 34-35 were prepared by methods analogous to that described for Intermediate 33 but replacing 5-bromopyrimidine with that indicated in Table 3. Modifications in the purification step are also indicated.

TABLE 3

| Int. | Structure | Starting material | Physical data |
|---|---|---|---|
| 34 | (structure) | (structure) ALFA-AESAR | $^1$H NMR (300 MHz, CD$_2$Cl$_2$) δ ppm: 8.25 (t, J = 3.4 Hz, 1H), 7.87-7.80 (m, 1H), 6.98-6.94 (m, 1H), 6.16-6.08 (m,1H), 4.26 (q, J = 2.9 Hz, 1H), 4.16 (q, J = 2.9 Hz, 1H), 3.86 (t, J = 5.7 Hz, 1H), 3.71 (t, J = 5.7 Hz, 1H), 2.71-2.48 (m, 6H). [ES + MS] m/z 303 (MH$^+$). |
| 35 | (structure) See footnote a) | (structure) SIGMA-ALDRICH | [ES + MS] m/z 286 (MH$^+$). | a) In DME/EtOH/H$_2$O (1/0.5/1, 3 mL), microwave irradiation at 80° C. for 90 min. Purification by flash chromatography on silica gel using a linear gradient of EtOAc/MeOH as eluents.

Intermediate 36 (4,4,4-trifluoro-1-(2'-(trifluoromethyl)-5,6-dihydro-[4,4'-bipyridin]-1(2H)-yl)butan-1-one)

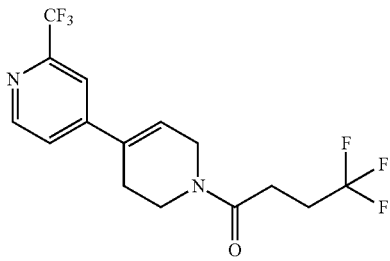 [SMILES: O=C(CCC(F)(F)F)N1CC=C(c2ccnc(C(F)(F)F)c2)CC1]

The solution of Intermediate 32 (110 g, 330.33 mmol), 4-chloro-2-(trifluoromethyl)pyridine (FRAPP'S CHEMICALS, 80.95 g, 445.94 mmol) in 1,4-dioxane (1100 mL) was nitrogen purged for 30 min. Followed by the addition of a solution of sodium carbonate (CHEMLABS, 70 g, 660.66 mmol) and Pd(dppf)$_2$Cl$_2$·CH$_2$Cl$_2$ complex (JOHNSON MATTHEY CATALYSTS, 26.9 g, 33.033 mmol) at 27° C. The reaction mixture was heated to 120° C. and stirred for 4 h at the same temperature. The progress of the reaction was monitored by TLC. On completion of the reaction, the reaction mixture was filtered through Celite and washed with EtOAc (4×500 mL). The filtrate was evaporated under reduced pressure. The crude was purified by column chromatography using a linear gradient of petroleum ether/EtOAc as eluents. The pure fractions were collected and concentrated under reduced pressure to afford tittle compound, (65 g, 53%) as a brown color thick liquid. $^1$H NMR (400 MHz, CDCl$_3$) δ ppm: 8.74-8.67 (m, 1H), 7.69-7.61 (m, 1H), 7.47-7.40 (m, 1H), 6.47-6.30 (m, 1H), 4.38-4.30 (m, 1H), 4.24-4.18 (m, 1H), 3.93-3.85 (m, 1H), 3.75-3.68 (m, 1H), 2.76-2.46 (m, 6H). [ES+MS] m/z 353 (MH$^+$).

Intermediates 37-44 were prepared by methods analogous to that described for Intermediate 36 but replacing the 4-chloro-2-(trifluoromethyl)pyridine with that indicated in Table 4.

TABLE 4

| Int. | Structure | Starting material | Physical data |
|---|---|---|---|
| 37 | (structure) | (structure) COMBI BLOCKS | $^1$H NMR (400 MHz, CDCl$_3$) δ ppm: 8.39-8.31 (m, 1H), 7.31-7.27 (m, 1H), 7.18 (d, J = 5.1 Hz, 1H), 6.40-6.24 (m, 1H), 4.34-4.27 (m, 1H), 4.21-4.15 (m, 1H), 3.88-3.81 (m, 1H), 3.74-3.65 (m, 1H), 2.72-2.45 (m, 6H). [ES + MS] m/z 319 (MH$^+$). |
| 38 | (structure) | (structure) COMBI BLOCKS | $^1$H NMR (400 MHz, CDCl$_3$) δ ppm: 8.50-8.27 (m, 2H), 7.22-7.14 (m, 1H), 6.25-6.18 (m, 1H), 4.35-4.25 (m, 1H), 4.20-4.16 (m, 1H), 3.90-3.80 (m, 1H), 3.70-3.62 (m, 1H), 2.70-2.46 (m, 6H). [ES + MS] m/z 303 (MH$^+$). |

TABLE 4-continued

| Int. | Structure | Starting material | Physical data |
|---|---|---|---|
| 39 | 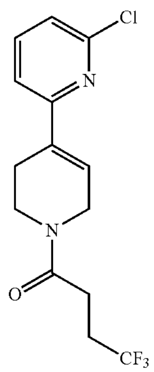 | COMBI BLOCKS | ¹H NMR (400 MHz, CDCl₃) δ ppm: 7.68-7.60 (m, 1H), 7.31-7.28 (m, 1H), 7.25-7.19 (m, 1H), 6.79-6.62 (m, 1H), 4.38-4.30 (m, 1H), 4.22-4.16 (m, 1H), 3.90-3.80 (m, 1H), 3.70-3.60 (m, 1H), 2.79-2.22 (m, 6H). [ES + MS] m/z 319 (MH⁺). |
| 40 | See footnote a) | OAKWOOD | ¹H NMR (400 MHz, CDCl₃) δ ppm: 8.92-8.75 (m, 2H), 6.90-6.80 (m, 1H), 4.42-4.38 (m, 1H), 4.30-4.24 (m, 1H), 3.92-3.84 (m, 1H), 3.78-3.70 (m, 1H), 2.84-2.49 (m, 6H). [ES + MS] m/z 354 (MH⁺). |
| 41 | 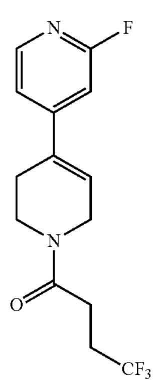 | COMBI BLOCKS | ¹H NMR (400 MHz, CDCl₃) δ ppm: 8.18 (br d, J = 5.5 Hz, 1H), 7.16 (br d, J = 5.0 Hz, 1H), 6.86 (br d, J = 6.4 Hz, 1H), 6.39-6.25 (m, 1H), 4.33-4.27 (m, 1H), 4.21-4.15 (m, 1H), 3.89-3.83 (m, 1H), 3.75-3.66 (m, 1H), 2.68-2.48 (m, 6H). [ES + MS] m/z 303 (MH⁺). |
| 42 | See footnote a) | COMBI BLOCKS | ¹H NMR (400 MHz, CDCl₃) δ ppm: 8.46 (d, J = 5.3 Hz, 1H), 7.11 (s, 1H), 7.06 (s, 1H), 6.33-6.19 (m, 1H), 4.31-4.25 (m, 1H), 4.18-4.14 (m, 1H), 3.88-3.81 (m, 1H), 3.72-3.66 (m, 1H), 2.77-2.47 (m, 9H). [ES + MS] m/z 299 (MH⁺). |
| 43 | | COMBI BLOCKS | ¹H NMR (400 MHz, CDCl₃) δ ppm: 7.98 (br d, J = 7.7 Hz, 1H), 7.62-7.46 (m, 1H), 6.21-6.01 (m, 1H), 4.32-4.06 (m, 2H), 3.90-3.83 (m, 1H), 3.74-3.68 (m, 1H), 2.76-2.33 (m, 6H). [ES + MS] m/z 321 (MH⁺). |
| 44 | | OAKWOOD | ¹H NMR (400 MHz, CDCl₃) δ ppm: 8.97-8.90 (m, 1H), 8.85-8.79 (m, 1H), 6.88-6.81 (m, 1H), 4.41-4.36 (m, 1H), 4.29-4.24 (m, 1H), 3.93-3.87 (m, 1H), 3.75-3.71 (m, 1H), 2.81-2.50 (m, 6H). [ES + MS] m/z 354. (MH⁺). | a) Purification by flash chromatography on silica gel using a linear gradient of DCM/MeOH as eluents.

Intermediate 45: 1-(4-(6-aminopyrazin-2-yl)-5,6-dihydropyridin-1(2H)-yl)-4,4,4-trifluorobutan-1-one

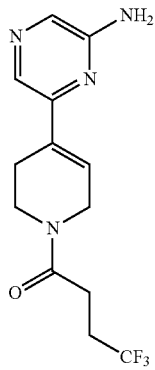

To a stirred solution of Intermediate 32 (600 mg, 1.8018 mmol) in 1,4-dioxane (10 mL) were added 6-bromopyrazin-2-amine (COMBI BLOCKS, 314 mg, 1.802 mmol), sodium carbonate (CHEMLABS, 477 mg, 4.504 mmol) and water (1 mL) and the reaction mixture was degassed with argon for 10 min at 26° C. Then added Pd(dppf)$_2$Cl$_2$.CH$_2$Cl$_2$ (ALFA-AESAR, 147 mg, 0.1802 mmol) at 26° C. and the reaction mixture was heated to 130° C. in microwave for 1 h. The reaction mixture was diluted with a mixture of MeOH, DCM (50 mL) and filtered through Celite pad. The filtrate was concentrated under reduced pressure and the crude was purified by neutral alumina chromatography column using a linear gradient of DCM/MeOH as eluents to yield the title compound (600 mg, 53%) as a black gummy liquid. $^1$H NMR (400 MHz, CDCl$_3$) δ ppm: 8.07-7.95 (m, 1H), 7.87 (d, J=6.1 Hz, 1H), 6.71-6.58 (m, 1H), 4.52 (br s, 2H), 4.35-4.25 (m, 1H), 4.23-4.10 (m, 1H), 3.84 (t, J=5.8 Hz, 1H), 3.72-3.62 (m, 1H), 2.90-2.10 (m, 4H). [ES+MS] m/z 301 (MH$^+$).

Intermediate 46: tert-butyl 5-amino-5',6'-dihydro-[3,4'-bipyridine]-1'(2'H)-carboxylate

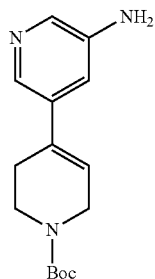 [SMILES: CC(C)(C)OC(=O)N1CC=C(c2cncc(N)c2)CC1]

Intermediate 46 was prepared using analogous method to that described for Intermediate 45 but replacing Intermediate 32 with tert-butyl 4-(4,4,5,5-tetramethyl-1,3,2-dioxaborolan-2-yl)-5,6-dihydropyridine-1(2H)-carboxylate and also replacing 6-bromopyrazin-2-amine with 5-bromopyridin-3-amine (COMBI BLOCKS, 560 mg, 3.2362 mmol). $^1$H NMR (400 MHz, CDCl$_3$) δ ppm: 8.06 (d, J=1.5 Hz, 1H), 7.98 (d, J=2.6 Hz, 1H), 6.92 (t, J=2.2 Hz, 1H), 6.04 (br s, 1H), 4.07 (br d, J=2.8 Hz, 2H), 3.78-3.66 (m, 2H), 3.63 (t, J=5.7 Hz, 2H), 2.55-2.41 (m, 2H), 1.49 (s, 9H). [ES+MS] m/z 276 (MH$^+$).

Intermediate 47: tert-butyl 4-(5-aminopyridin-3-yl)piperidine-1-carboxylate

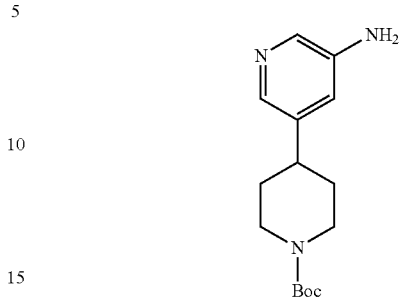

To a solution of Intermediate 46 (800 mg, 2.909 mmol) in MeOH (20 mL) was added 10% Pd/C (HINDUSTAN, 400 mg) at 27° C. The reaction mixture was stirred for 3 h under hydrogen atmosphere (balloon pressure) at the same temperature. The reaction mixture was filtered through Celite pad under nitrogen atmosphere and the filtrate was concentrated under reduced pressure to yield the title compound (600 mg, 67%) as a black gummy liquid. $^1$H NMR (400 MHz, CDCl$_3$) δ ppm: 8.04-7.83 (m, 2H), 6.80 (s, 1H), 4.32-4.15 (m, 2H), 3.98-3.35 (m, 2H), 2.89-2.70 (m, 2H), 2.64-2.57 (m, 1H), 1.80 (br d, J=12.9 Hz, 2H), 1.69-1.56 (m, 2H), 1.48 (s, 9H). [ES+MS] m/z 278 (MH$^+$).

Intermediate 48: tert-butyl 4-(5-chloropyridin-3-yl)piperidine-1-carboxylate

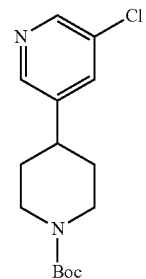 [SMILES: CC(C)(C)OC(=O)N1CCC(c2cncc(Cl)c2)CC1]

To a solution of Intermediate 47 (600 mg, 2.166 mmol) in ACN (10 mL) was added isopentyl nitrite (RNR, 381 mg, 3.249 mmol) drop wise at 27° C. and stirred for 10 min, followed by the addition of copper(II) chloride (ALFA-AESAR, 437 mg, 3.249 mmol) at the same temperature. The reaction mixture was heated to 60° C. and stirred for 1.5 h at the same temperature. The reaction mixture was concentrated under reduced pressure, the residue was dissolved in EtOAc (50 mL) and filtered through Celite pad. Water (60 mL) was added to the filtrate and extracted with EtOAc (3×50 mL). The combined organic layer was dried over (anh) Na$_2$SO$_4$, filtered and the filtrate was concentrated under reduced pressure. The crude was purified by silica chromatography column using a gradient of DCM/MeOH as eluents to yield the title compound (350 mg) as a brown liquid. $^1$H NMR (400 MHz, CDCl$_3$) δ ppm: 8.57-8.26 (m, 2H), 7.51 (s, 1H), 2.95-2.73 (m, 2H), 2.73-2.59 (m, 1H), 1.92-1.78 (m, 2H), 1.70-1.56 (m, 4H), 1.48 (s, 9H). [ES+MS] m/z 297 (MH$^+$).

Intermediate 49: 3-chloro-5-(piperidin-4-yl)pyridine Hydrochloride

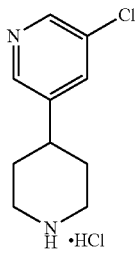 [SMILES: Clc1cncc(C2CCNCC2)c1 ; Cl]

To a solution of Intermediate 48 (350 mg, 1.182 mmol) EtOAc (5 mL) was added 4M HCl in EtOAc (HYCHEM, 3 mL) at 0° C. The reaction mixture was allowed to 27° C. and stirred for 2 h at the same temperature. The reaction mixture was concentrated under reduced pressure and the resulting residue was washed with diethyl ether, dried under vacuum to yield the title compound (300 mg) as an off white gummy solid. $^1$H NMR (400 MHz, DMSO-$d_6$) δ ppm: 9.05-8.67 (m, 2H), 8.59-8.38 (m, 2H), 7.80 (s, 1H), 3.45-3.25 (m, 2H), 2.98 (q, J=11.5 Hz, 3H), 2.06-1.80 (m, 4H). [ES+MS] m/z 197 (MH$^+$).

Intermediate 50: 1-(4-(6-aminopyrazin-2-yl)piperidin-1-yl)-4,4,4-trifluorobutan-1-one

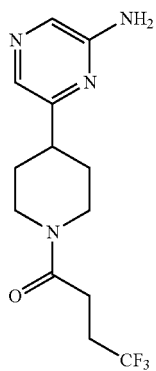 [SMILES: Nc1cncc(C2CCN(C(=O)CCC(F)(F)F)CC2)n1]

To a solution of Intermediate 45 (600 mg, 2.0 mmol) in MeOH (10 mL) was added 10% Pd/C (HINDUSTAN, 300 mg) at 27° C. The reaction mixture was stirred for 2 h under hydrogen atmosphere (balloon pressure) at the same temperature. The reaction mixture was filtered through Celite pad under nitrogen atmosphere and the filtrate was concentrated under reduced pressure to yield the title compound (400 mg, 42%) as a black gummy liquid. $^1$H NMR (400 MHz, CDCl$_3$) δ ppm: 7.84 (s, 1H), 7.79 (s, 1H), 4.51 (br s, 2H), 4.02-3.90 (m, 2H), 3.24-3.14 (m, 1H), 2.60-2.44 (m, 4H), 1.91 (br d, J=15.3 Hz, 2H), 1.76-1.70 (m, 2H). [ES+MS] m/z 303 (MH$^+$).

Intermediate 51: tert-butyl 4-hydroxy-4-(pyridin-2-yl)piperidine-1-carboxylate

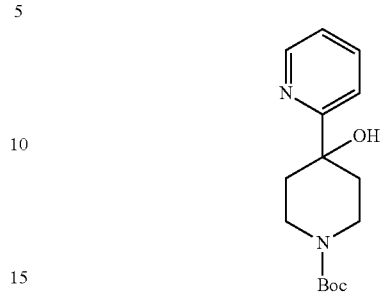

To a suspension of tert-butyl 4-oxopiperidine-1-carboxylate (ASHVARSHA, 1 g, 5.018 mmol) and 2-bromopyridine (MERCK, 1.03 g, 6.524 mmol) in DCM (10 mL) was added n-butyl lithium (2.5 M in Hexane) (HYCHEM, 2 mL, 5.018 mmol) at −78° C. The reaction mixture was stirred for 3 h at −78° C. The reaction mixture was quenched with saturated ammonium chloride solution (50 mL) and extracted with DCM (3×70 mL). The organic layer was washed with brine solution (50 mL), dried over (anh) Na$_2$SO$_4$, filtered and the filtrate was concentrated under reduced pressure. The crude was purified by silica chromatography column using a linear gradient of petroleum ether/EtOAc as eluents to yield the title compound (750 mg, 50.7%) as a pale yellow liquid. $^1$H NMR (400 MHz, CDCl$_3$) δ ppm: 8.54 (d, J=4.6 Hz, 1H), 7.77-7.69 (m, 1H), 7.33 (d, J=7.9 Hz, 1H), 7.25-7.19 (m, 1H), 4.16-4.01 (m, 2H), 3.29 (br t, J=12.3 Hz, 2H), 2.00-1.87 (m, 2H), 1.60 (br d, J=12.1 Hz, 2H), 1.49 (s, 9H). [ES+MS] m/z 279 (MH$^+$).

Intermediates 52-55 were prepared by methods analogous to that described for intermediate 51 but replacing the bromo compound with that indicated in Table 5.

TABLE 5

| Int. | Structure | Starting material | Physical data |
|---|---|---|---|
| 52 | (pyridine with CF$_3$, piperidine-OH, N-Boc) | 3-bromo-5-(trifluoromethyl)pyridine, COMBI BLOCKS | $^1$H NMR (400 MHz, CDCl$_3$) δ ppm: 8.92 (d, J = 2.2 Hz, 1H), 8.85-8.75 (m, 1H), 8.06 (d, J = 2.3 Hz, 1H), 4.39-3.78 (m, 3H), 3.48-3.04 (m, 2H), 2.57-2.37 (m, 1H), 1.86-1.70 (m, 2H), 1.51-1.43 (m, 9H). [ES + MS] m/z 347 (MH$^+$). |
| 53 | (2-CF$_3$-pyridine, piperidine-OH, N-Boc) | 4-bromo-2-(trifluoromethyl)pyridine, ALFA-AESAR | $^1$H NMR (400MHz, CDCl$_3$) δ ppm: 8.71 (d, J = 5.3 Hz, 1H), 7.81 (d, J = 0.9 Hz, 1H), 7.61-7.47 (m, 1H), 4.20-4.04 (m, 2H), 3.21 (br t, J = 12.3 Hz, 2H), 2.03-1.91 (m, 2H), 1.70 (br d, J = 12.5 Hz, 2H), 1.54-1.44 (m, 9H). [ES + MS] m/z 347 (MH$^+$). |

TABLE 5-continued

| Int. | Structure | Starting material | Physical data |
|---|---|---|---|
| 54 | (pyrazine-Cl with piperidin-4-ol N-Boc) | (pyrazine-Cl-Br) COMBI BLOCKS | $^1$H NMR (400 MHz, CDCl$_3$) δ ppm: 8.67 (s, 1H), 8.54 (s, 1H), 4.18-4.03 (m, 2H), 3.24 (d, J = 11.8 Hz, 3H), 2.17-1.96 (m, 2H), 1.71 (d, J = 13.3 Hz, 2H), 1.49 (s, 9H). [ES + MS] m/z 314 (MH$^+$). |
| 55 | (pyridine-F with piperidin-4-ol N-Boc) | (pyridine-F-Br) COMBI BLOCKS | $^1$H NMR (400 MHz, CDCl$_3$) δ ppm: 8.18 (d, J = 5.3 Hz, 1H), 7.26-7.20 (m, 1H), 7.06 (d, J = 1.5 Hz, 1H), 4.19-3.99 (m, 2H), 3.21 (t, J = 12.6 Hz, 2H), 2.02-1.86 (m, 2H), 1.76-1.58 (m, 2H), 1.48 (s, 9H). [ES + MS] m/z 297 (MH$^+$). |
| 55a | (pyridine-Cl with piperidin-4-ol N-Boc) | (pyridine-Cl-Br) ENAMINE | $^1$H NMR (300 MHz, CDCl$_3$) δ ppm: 8.27 (d, J = 5.3 Hz, 1H), 7.45 (d, J = 1.3 Hz, 1H), 7.26-7.29 (m, 1H), 4.02 (d, J = 12.4 Hz, 2H), 3.19 (t, J = 12.4 Hz, 2H), 2.75 (brs, 1H), 1.91-1.85 (m, 2H), 1.68 (d, J = 13.0 Hz, 2H), 1.45 (s, 9H). [ES + MS] m/z 313 (MH$^+$). |

Intermediate 56: tert-butyl 4-(5-chloropyridin-3-yl)-4-hydroxypiperidine-1-carboxylate

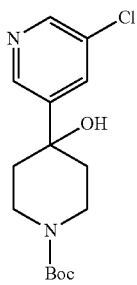 [SMILES: CC(C)(C)OC(=O)N1CCC(O)(c2cncc(Cl)c2)CC1]

To a stirred solution of tert-butyl 4-oxopiperidine-1-carboxylate (VASUDHA CHEMICALS, 3.0 g, 15.056 mmol) and 3-bromo-5-chloropyridine (COMBI BLOCKS, 2.89 g, 15.056 mmol) in THF (30 mL) was added n-butyl lithium (1.6 M in Hexane) (HYCHEM, 9.4 mL, 15.056 mmol) dropwise at −78° C. The reaction mixture was stirred for 2 h at −78° C. The reaction mixture was quenched with saturated ammonium chloride solution (50 mL) and extracted with EtOAc (2×50 mL). The combined organic layers were washed with saturated brine solution (100 mL), dried over (anh) Na$_2$SO$_4$ and filtered. The filtrate was concentrated under reduced pressure and the crude was purified by silica chromatography column using a linear gradient of petroleum ether/EtOAc as eluents to yield the title compound (2.0 g, 40%) as a brown thick liquid. $^1$H NMR (400 MHz, CDCl$_3$) δ ppm: 8.60 (d, J=2.1 Hz, 1H), 8.49 (d, J=2.3 Hz, 1H), 7.81 (t, J=2.2 Hz, 1H), 4.17-4.02 (m, 2H), 3.22 (t, J=13.1 Hz, 2H), 2.03-1.92 (m, 2H), 1.78-1.70 (m, 2H), 1.49 (s, 9H). [ES+MS] m/z 313 (MH$^+$).

Intermediate 57: 4-(pyridin-2-yl)piperidin-4-ol hydrochloride

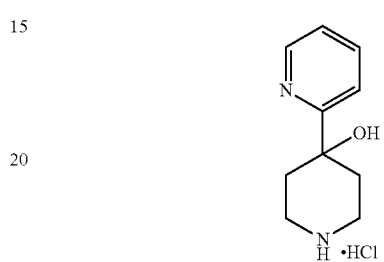

To a solution of Intermediate 51 (750 mg, 3.493 mmol) in EtOAc (7 mL) was added 4M HCl in EtOAc (HYCHEM, 7 mL) at 0° C. The reaction mixture was allowed to 26° C. and stirred for 3 h at the same temperature. The reaction mixture was concentrated under reduced pressure to yield the title compound (550 mg, 39%) as a white solid. $^1$H NMR (400 MHz, DMSO-d$_6$) δ ppm: 9.29-8.93 (m, 2H), 8.64 (br d, J=3.9 Hz, 1H), 8.13 (br s, 1H), 7.82 (br d, J=7.9 Hz, 1H), 7.56 (br s, 1H), 3.33-3.09 (m, 4H), 2.46-2.34 (m, 2H), 1.82 (br d, J=14.3 Hz, 2H). [ES+MS] m/z 179 (MH$^+$).

Intermediates 58-61 were prepared by methods analogous to that described for intermediate 57 but replacing the Intermediate 51 with the intermediates indicated in Table 6.

TABLE 6

| Int. | Structure | Starting Int. | Physical data |
|---|---|---|---|
| 58 | (pyridine-CF$_3$ with piperidin-4-ol HCl) See footnote a) | 52 | $^1$H NMR (400 MHz, DMSO-d$_6$) δ ppm: 9.18-9.01 (m, 3H), 9.00-8.88 (m, 1H), 8.19 (d, J = 2.2 Hz, 1H), 3.30-3.04 (m, 4H), 2.41-2.28 (m, 2H), 1.96-1.78 (m, 2H). [ES + MS] m/z 247 (MH$^+$). |
| 59 | (pyridine-CF$_3$ with piperidin-4-ol HCl) See footnote b) | 53 | $^1$H NMR (400 MHz, DMSO-d$_6$) δ ppm: 9.32-9.00 (m, 2H), 8.79 (d, J = 5.0 Hz, 1H), 7.92 (s, 1H), 7.74 (d, J = 4.2 Hz, 1H), 3.30-3.05 (m, 4H), 2.40-2-3 (m, 2H), 1.78 (br d, J = 13.8 Hz, 2H). [ES + MS] (MH$^+$). |

TABLE 6-continued

| Int. | Structure | Starting Int. | Physical data |
|---|---|---|---|
| 60 | (pyrazine with Cl, piperidine-OH, NH·HCl) See footnote a) | 54 | ¹H NMR (400 MHz, DMSO-d₆) δ ppm: 9.38 (br d, J = 10.8 Hz, 1H), 8.93 (s, 2H), 8.74 (s, 1H), 7.09 (s, 1H), 3.37-2.94 (m, 4H), 2.36-2.20 (m, 2H), 1.86 (d, J = 14.0 Hz, 2H). [ES + MS] m/z 214 (MH⁺). |
| 61 | (2-fluoropyridine, piperidine-OH, NH·HCl) See footnote a) | 55 | ¹H NMR (400 MHz, DMSO-d₆) δ ppm: 9.44 (s, 1H), 9.23 (s, 1H), 8.25 (d, J = 5.3 Hz, 1H), 7.45-7.35 (m, 1H), 7.18 (d, J = 1.5 Hz, 1H), 3.30-3.07 (m, 4H), 2.41-2.27 (m, 2H), 1.78 (d, J = 14.0 Hz, 2H). [ES + MS] m/z 197 (MH⁺). | a) Purified by washed with diethyl ether
b) Purified by washed with n-pentane.

Intermediate 62: 4,4,4-trifluoro-1-(4-hydroxy-4-(pyridin-2-yl)piperidin-1-yl)butan-1-one To a solution of Intermediate 57 (550 mg, 2.570 mmol), EDC.HCl (SILVERY, 1.22 g, 6.425 mmol) and 4,4,4-trifluorobutanoic acid (MATRIX, 437 mg, 3.084 mmol) in DMF was added DMAP (AVRA, 940 mg, 7.710 mmol) at 27° C. The resultant reaction mixture was stirred for 16 h at 26° C. The reaction mixture was diluted with water (50 mL) and extracted with EtOAc (3×100 mL). Combined organic layers were washed with brine solution (100 mL), dried over (anh) NaSO₄ filtered and concentrated under reduced pressure. The crude was purified by silica chromatography column using a linear gradient of petroleum ether/EtOAc as eluents to yield the title compound (450 mg, 53.69%) as a pale yellow liquid. ¹H NMR (400 MHz, CDCl₃) δ ppm: 8.56 (d, J=5.0 Hz, 1H), 7.78-7.71 (m, 1H), 7.32 (d, J=8.1 Hz, 1H), 7.25 (br d, J=5.0 Hz, 1H), 5.32 (s, 1H), 4.72-4.61 (m, 1H), 3.88-3.74 (m, 1H), 3.74-3.62 (m, 1H), 3.26-3.07 (m, 1H), 2.67-2.48 (m, 4H), 2.01-1.86 (m, 2H), 1.79-1.60 (m, 2H). [ES+MS] m/z 303 (MH⁺).

Intermediates 63-66 were prepared by methods analogous to that described for Intermediate 62 but replacing the Intermediate 57 with the intermediates indicated in Table 7.

TABLE 7

| Int. | Structure | Starting Int. | Physical data |
|---|---|---|---|
| 63 | (5-CF₃-pyridin-3-yl, piperidine-OH, N-C(O)CH₂CH₂CF₃) | 58 | ¹H NMR (400 MHz, CDCl3) δ ppm: 8.90 (d, J = 2.2 Hz, 1H), 8.80 (d, J = 2.0 Hz, 1H), 8.07 (t, J = 2.2 Hz, 1H), 4.69-4.57 (m, 1H), 3.86-3-76 (m, 1H), 3.71-3.57 (m, 1H), 3.18-3.06 (m, 1H), 2.73-2.41 (m, 4H), 2.12-1.81 (m, 4H). [ES + MS] m/z 371 (MH⁺). |

TABLE 7-continued

| Int. | Structure | Starting Int. | Physical data |
|---|---|---|---|
| 64 | (pyridine with CF3, 4-hydroxypiperidine, N-acyl with CH2CH2CF3) | 59 | $^1$H NMR (400 MHz, CDCl$_3$) δ ppm: 8.73 (d, J = 5.3 Hz, 1H), 7.81 (d, J = 1.1 Hz, 1H), 7.60-7.52 (m, 1H), 4.66 (br d, J = 11.8 Hz, 1H), 3.87-3.74 (m, 1H), 3.71-3.57 (m, 1H), 3.18-3.06 (m, 1H), 2.74-2.46 (m, 4H), 2.14-1.73 (m, 5H). [ES + MS] m/z 371 (MH$^+$). |
| 65 | (6-chloropyrazine, 4-hydroxypiperidine, N-acyl with CH2CH2CF3) See footnote a) | 60 | $^1$H NMR (400 MHz, CDCl$_3$) δ ppm: 8.67 (s, 1H), 8.56 (s, 1H), 4.75-4.59 (m, 1H), 3.88-3.76 (m, 1H), 3.70-3.57 (m, 1H), 3.37 (s, 1H), 3.20-3.09 (m, 1H), 2.72-2.45 (m, 4H), 2.13-1.97 (m, 2H), 1.87-1.75 (m, 2H). [ES + MS] m/z 338 (MH$^+$). |
| 66 | (2-fluoropyridine, 4-hydroxypiperidine, N-acyl with CH2CH2CF3) | 61 | $^1$H NMR (400 MHz, CDCl$_3$) δ ppm: 8.21 (d, J = 5.3 Hz, 1H), 7.25-7.19 (m, 1H), 7.05 (d, J = 1.6 Hz, 1H), 4.65-4.57 (m, 1H), 3.79 (d, J = 13.7 Hz, 1H), 3.65-3.53 (m, 1H), 3.14-3.03 (m, 1H), 2.72-2.40 (m, 4H), 2.07-1.87 (m, 2H), 1.79 (t, J = 17.0 Hz, 2H). [ES + MS] m/z 321 (MH$^+$). | a) Continued for the next step without purification

Intermediate 66a: tert-butyl 4-hydroxy-4-[4-(trifluoromethyl)-2-pyridyl]piperidine-1-carboxylate

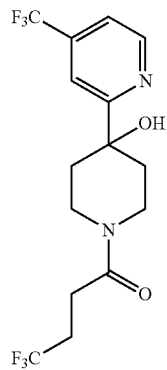 [SMILES: O=C(CCC(F)(F)F)N1CCC(O)(c2cc(C(F)(F)F)ccn2)CC1]

A solution of 2-bromo-4-(trifluoromethyl)pyridine (FLUOROCHEM, 139 μL, 1.12 mmol) in anhydrous DCM (3 mL) was cooled at −78° C. under Argon. Then, n-BuLi 2.5 M in hexanes (0.450 mL, 1.12 mmol) was added dropwise and the resulting orange solution was stirred at −78° C. during 30 minutes. Intermediate 2 (250 mg, 1.12 mmol) in anhydrous DCM (1.5 mL+1.5 mL rinse) was slowly added at −78° C. and the reaction mixture was stirred during 2 hours. (LCMS monitoring). The reaction was quenched with sat. NH$_4$Cl solution (15 mL), extracted with DCM and the organic phase was washed with brine (25 mL). The organic phase was dried over MgSO$_4$ and concentrated in vacuo. The crude mixture was purified on preparative HPLC (ACN/H$_2$O/HCOOH, 10/90 to 100/0, 32 min) to yield the title compound (111 mg, 27%) as a colorless oil. 1H NMR (300 MHz, CDCl3) δ ppm: 8.75 (d, J=5.3 Hz, 1H), 7.58 (s, 1H), 7.49 (d, J=5.3 Hz; 1.3 Hz, 1H), 4.67 (d, J=13.1 Hz, 1H), 3.82 (d, J=13.1 Hz, 1H), 3.71-3.61 (m, J=12.8 Hz, 2.5 Hz, 1H), 3.21-3.11 (m, J=12.8 Hz, 2.8 Hz, 1H), 2.69-2.60 (m, 2H), 2.60-2.46 (m, 2H), 2.06-1.93 (m, 2H), 1.72 (brt, J=12.1 Hz, 2H). [ES+MS] m/z 371 (MH+).

Intermediate 66b: tert-butyl 4-hydroxy-4-[4-(trifluoromethyl)-2-pyridyl]piperidine-1-carboxylate

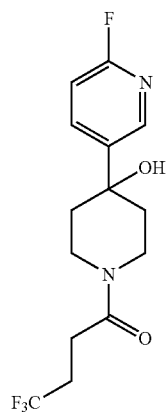 [SMILES: O=C(CCC(F)(F)F)N1CCC(O)(c2ccc(F)nc2)CC1]

Intermediate 66b was prepared by method analogous to that described for Intermediate 66a, replacing 2-bromo-4-(trifluoromethyl)pyridine with 5-bromo-2-fluoro-pyridine (FLUOROCHEM). 1H NMR (300 MHz, CD$_2$Cl$_2$) δ ppm: 8.28-8.27 (m, 1H), 7.96-7.89 (m, 1H), 6.95-6.90 (m, 1H), 4.51-4.45 (m, 1H), 3.77-3.71 (m, 1H), 3.63-3.53 (m, 1H), 3.32 (s, 1H), 3.14-3.05 (m, 1H), 2.64-2.39 (m, 4H), 1.97-1.5 (m, 4H). [ES+MS] m/z 321 (MH+).

Intermediate 67: tert-butyl 4-(5-chloropyridin-3-yl)-4-fluoropiperidine-1-carboxylate

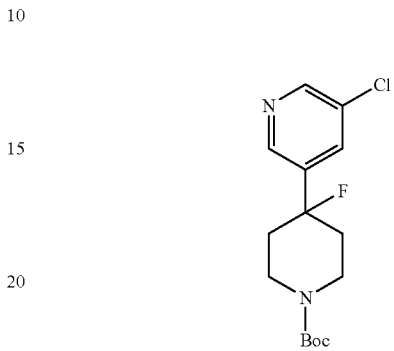

To a solution of Intermediate 56 (1.5 g, 4.796 mmol) in DCM (27 mL) was added a solution of DAST (ALFA-AESAR, 0.628 mL, 4.796 mmol) in DCM (3 mL) drop wise at −78° C. The reaction mixture was allowed to 0° C. and stirred for 40 min at the same temperature. The reaction mixture was quenched with saturated sodium bicarbonate solution (200 mL) and extracted with DCM (2×50 mL). Combined organic layers were dried over (anh) Na$_2$SO$_4$, filtered and concentrated under reduced pressure. The crude was purified by silica chromatography column using a linear gradient of petroleum ether/EtOAc as eluents to yield the title compound (800 mg, 63%) as a colorless thick liquid. $^1$H NMR (400 MHz, CDCl$_3$) δ ppm: 8.54 (d, J=2.3 Hz, 1H), 8.49 (d, J=1.9 Hz, 1H), 7.71 (t, J=2.2 Hz, 1H), 4.15 (s, 2H), 3.17 (s, 2H), 2.08-1.85 (m, 4H), 1.49 (s, 9H). [ES+MS] m/z 315 (MH$^+$).

Intermediate 67a: tert-butyl 4-(2-chloro-4-pyridyl)-4-fluoro-piperidine-1-carboxylate

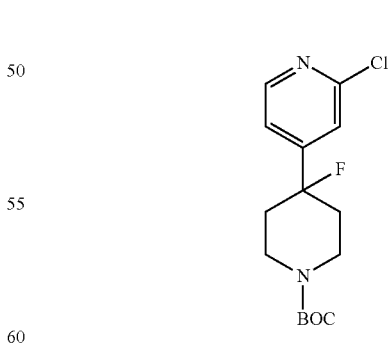

Intermediate 67a was prepared by method analogous to that described for Intermediate 67, replacing Intermediate 56 with Intermediate 55a. 1H NMR (300 MHz, CD$_2$Cl$_2$) δ ppm: 8.37 (d, J=5.2 Hz, 1H), 7.34 (d, J=1.4 Hz, 1H), 7.25-7.15 (m, 1H), 4.13 (d, J=12.4 Hz, 2H), 3.11 (d, J=11.6 Hz, 2H), 2.06-1.81 (m, 4H), 1.46 (s, 9H). [ES+MS] m/z 315 (MH+).

Intermediate 67b: 2-chloro-4-(4-fluoro-4-piperidyl)pyridine; 2,2,2-trifluoroacetic Acid

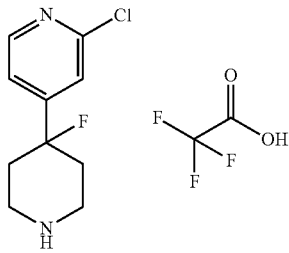 [SMILES: FC1(c2ccnc(Cl)c2)CCNCC1 ; O=C(O)C(F)(F)F]

Intermediate 67a (22.0 mg, 0.07 mmol) was dissolved in DCM (1.0 mL). A solution of 50:50 DCM/TFA (0.2 mL) was slowly added at RT. The solution was stirred at room temperature during 2 h. The solvent was removed under reduced pressure to yield the title compound (23 mg, 100%) as an off white solid. The crude was judged sufficiently pure to be used for the next step. [ES+MS] m/z 215 (MH+).

Intermediate 68: 3-chloro-5-(4-fluoropiperidin-4-yl)pyridine Hydrochloride

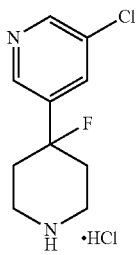 [SMILES: FC1(c2cncc(Cl)c2)CCNCC1 ; Cl]

To a solution of Intermediate 67 (800 mg, 2.541 mmol) in EtOAc (8 mL) was added 4M HCl in EtOAc (SYMAX FINE CHEMICALS, 8 mL) at 0° C. The reaction mixture was allowed to warm to 26° C. and stirred for 3 h at the same temperature. The reaction mixture was concentrated under reduced pressure and the residue was washed with diethyl ether (3×10 mL) and dried under vacuum to yield the title compound (650 mg) as a white solid. $^1$H NMR (400 MHz, DMSO-$d_6$) δ ppm: 9.64 (s, 1H), 9.38 (s, 1H), 8.74-8.60 (m, 2H), 7.97 (t, J=2.1 Hz, 1H), 3.42-3.31 (m, 2H), 3.21-3.04 (m, 2H), 2.69-2.55 (m, 2H), 2.29-2.16 (m, 2H). [ES+MS] m/z 215 (MH+—HCl).

Intermediate 69: 5-(4,4,5,5-tetramethyl-1,3,2-dioxaborolan-2-yl)pyridin-3-amine

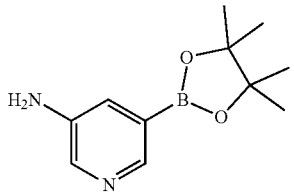 [SMILES: CC1(C)OB(c2cncc(N)c2)OC1(C)C]

To a stirred solution of 5-bromopyridin-3-amine (MANCHESTER ORGANICS, 1 g, 5.78 mmol) in 1,4-dioxane (15 mL) were added 4,4,4',4',5,5,5',5'-octamethyl-2,2'-bi(1,3,2-dioxaborolane) (ALFA-AESAR, 1.46 g, 5.78 mmol), potassium acetate (AVRA, 1.1 g, 11.56 mmol) and the reaction mixture was degassed with argon for 10 min. Followed by the addition of Pd(dppf)Cl$_2$.CH$_2$Cl$_2$ (ALFA-AESAR, 200 mg, 0.289 mmol). The reaction mixture was heated to 100° C. and stirred for 4 h. The reaction mixture was cooled to 27° C. and proceeded to next step without further purification. $^1$H NMR (400 MHz, CDCl$_3$) δ ppm: 8.36 (s, 1H), 8.22-8.13 (m, 1H), 8.10-7.95 (m, 1H), 7.36 (br s, 2H), 1.27 (s, 12H).

Intermediate 70: tert-butyl 3-(((trifluoromethyl)sulfonyl)oxy)-2,5-dihydro-1H-pyrrole-1-carboxylate

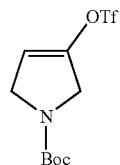

To a solution of tert-butyl 3-oxopyrrolidine-1-carboxylate (COM ACCERA CHEMBIO, 500 mg, 2.699 mmol) and N-phenylbis(trifluoromethanesulfonamide) (COMBI BLOCKS, 1.9 g, 5.398 mmol) in THF (10 mL) was added NaHMDS (1 M in THF) (HYCHEM, 5.39 mL, 5.398 mmol) in drop wise at −78° C. The reaction mixture was allowed to 27° C. and stirred for 16 h at the same temperature. Reaction mixture was quenched with saturated ammonium chloride solution (20 mL) and extracted with EtOAc (2×20 mL). Combined organic layers were washed with brine (50 mL), dried over (anh) Na$_2$SO$_4$, filtered and evaporated under reduced pressure. The crude was purified by silica chromatography column using a linear gradient of petroleum ether/EtOAc to yield the title compound (800 mg) as a pale yellow liquid. $^1$H NMR (400 MHz, CDCl$_3$) δ ppm: 7.01-6.94 (m, 1H), 4.28-4.17 (m, 4H), 1.48 (s, 9H).

Intermediate 71: tert-butyl 3-(5-aminopyridin-3-yl)-2,5-dihydro-1H-pyrrole-1-carboxylate

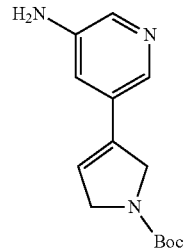

To a stirred solution of Intermediate 69 (reaction mixture) in 1,4-dioxane were added Intermediate 70 (800 mg, 2.521 mmol), cesium carbonate (ALFA-AESAR, 7.4 g, 22.692 mmol) and water (3.0 mL) and the reaction mixture was degassed with argon for 10 min. Followed by the addition of Pd(PPh$_3$)$_4$ (ALFA-AESAR, 200 mg, 0.176 mmol) at 27° C. The reaction mixture was heated to 100° C. and stirred for 2 h at the same temperature. The reaction mixture was filtered through Celite pad and the filtrate was concentrated under reduced pressure. The crude was purified by silica chromatography column using a linear gradient of petroleum ether/EtOAc as eluents to yield the title compound (300 mg) as a brown solid. $^1$H NMR (400 MHz, CDCl$_3$) δ ppm: 8.13-8.04 (m, 1H), 8.03-7.97 (m, 1H), 7.02-6.90 (m, 1H), 6.24-6.12 (m, 1H), 4.53-4.39 (m, 2H), 4.37-4.23 (m, 2H), 1.51 (s, 9H). [ES+MS] m/z 262 (MH$^+$).

Intermediate 72: tert-butyl 3-(5-aminopyridin-3-yl)pyrrolidine-1-carboxylate

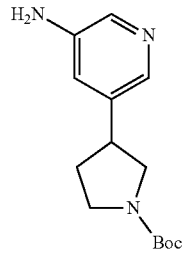

To a solution of Intermediate 71 (300 mg, 1.148 mmol) in MeOH (10 mL) was added 10% Pd/C (HINDUSTAN, 150 mg) at 27° C. The reaction mixture was stirred for 4 h under hydrogen atmosphere (balloon pressure) at the same temperature. The reaction mixture was filtered through Celite pad under nitrogen atmosphere and the filtrate was concentrated under reduced pressure to yield the title compound (300 mg) as a pale yellow thick liquid. $^1$H NMR (400 MHz, CDCl$_3$) δ ppm: 7.97 (d, J=2.6 Hz, 1H), 7.92 (d, J=1.9 Hz, 1H), 6.83 (t, J=2.2 Hz, 1H), 3.90-3.50 (m, 2H), 3.48-3.24 (m, 2H), 2.30-2.20 (m, 1H), 2.02-1.87 (m, 2H), 1.48 (s, 9H). [ES+MS] m/z 264 (MH$^+$).

Intermediate 73: tert-butyl 3-(5-chloropyridin-3-yl)pyrrolidine-1-carboxylate

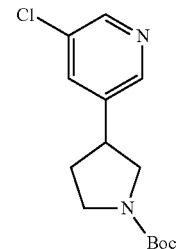 [SMILES: CC(C)(C)OC(=O)N1CCC(c2cncc(Cl)c2)C1]

To a solution of Intermediate 72 (300 mg, 1.139 mmol) in ACN (5 mL) was added copper(II) chloride (ALFA-AESAR, 230 mg, 1.708 mmol) in portion wise at 27° C. and stirred for 20 min at the same temperature. Followed by the addition of isoamyl nitrite (RNR, 0.25 mL, 1.708 mmol) in drop wise at 27° C. The reaction mixture was heated to 65° C. and stirred for 1.5 h. The reaction mixture was quenched with ice cold water (20 mL) and extracted with EtOAc (2×20 mL). The combined organic layers were washed with brine (50 mL), dried over (anh) Na$_2$SO$_4$, filtered and concentrated under reduced pressure. The crude was purified by silica chromatography column using a linear gradient of petroleum ether/EtOAc as eluents to yield the title compound (160 mg, 49%) as a pale yellow thick liquid. $^1$H NMR (400 MHz, CDCl$_3$) δ ppm: 8.47 (d, J=2.3 Hz, 1H), 8.39 (d, J=1.9 Hz, 1H), 7.54 (s, 1H), 3.93-3.52 (m, 2H), 3.51-3.24 (m, 2H), 2.37-2.26 (m, 1H), 1.73-1.53 (m, 2H), 1.48 (s, 9H). [ES+MS] m/z 283 (MH$^+$).

Intermediate 74: 3-chloro-5-(pyrrolidin-3-yl)pyridine Hydrochloride

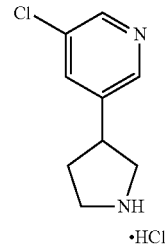 [SMILES: Clc1cncc(C2CCNC2)c1 ; Cl]

To a solution of Intermediate 73 (160 mg, 0.566 mmol) in EtOAc (2 mL) was added 4M HCl in EtOAc (SYMAX FINE CHEMICALS, 2 mL) at 0° C. The reaction mixture was allowed to 27° C. and stirred for 3 h at the same temperature. The reaction mixture was concentrated under reduced pressure to yield the title compound (120 mg) as a brown thick liquid. $^1$H NMR (400 MHz, DMSO-d$_6$) δ ppm: 9.66 (br s, 2H), 8.64-8.55 (m, 2H), 8.13 (s, 1H), 3.68-3.50 (m, 2H), 3.47-3.35 (m, 1H), 3.28-3.09 (m, 2H), 2.46-2.35 (m, 1H), 2.09-1.94 (m, 1H). [ES+MS] m/z 183 (MH$^+$).

EXAMPLES

Reference Example 1: 4,4,4-trifluoro-1-(4-pyrazin-2-yl-1-piperidyl)butan-1-one

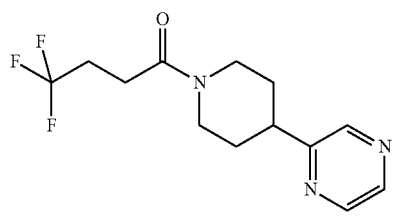 [SMILES: O=C(CCC(F)(F)F)N1CCC(c2cnccn2)CC1]

To a solution of 2-(4-piperidyl)pyrazine dihydrochloride (ENAMINE, 397.5 mg, 1.68 mmol) and DMAP (SIGMA-ALDRICH, 422.7 mg, 3.46 mmol) in chloroform (3.4 mL) was added Intermediate 1 (399.3 mg, 1.64 mmol). The solution was exposed to microwave irradiation for 15 min at 100° C. The reaction mixture was washed with a saturated solution of Na$_2$CO$_3$ (×2). The organic layer was washed with brine, dried over (anh) MgSO$_4$ and evaporated. The residue was purified by preparative HPLC (OmniSpher C18 column, 10 μm, 41×250 mm) gradient 15 min 10% to 100% ACN/H$_2$O (0.1% formic acid) to give title compound (353.3 mg, 74.9%) as a white solid. $^1$H NMR (300 MHz, CD$_2$Cl$_2$) δ ppm: 8.48-8.47 (m, 2H), 8.41-8.39 (m, 1H), 4.74-4.67 (m, 1H), 3.99-3.92 (m, 1H), 3.23-3.14 (m, 1H), 3.05-2.94 (m, 1H), 2.77-2.67 (m, 1H), 2.64-2.57 (m, 2H), 2.55-2.42 (m, 2H), 2.00-1.92 (m, 2H), 1.87-1.65 (m, 2H). [ES+MS] m/z 288 (MH$^+$).

Example 2: 4,4,4-trifluoro-1-[4-fluoro-4-(3-pyridyl)-1-piperidyl]butan-1-one

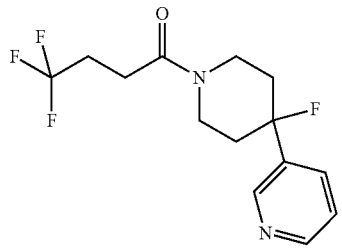 [SMILES: O=C(CCC(F)(F)F)N1CCC(F)(c2cccnc2)CC1]

Example 2 was prepared by method analogous to that described for Example 1, replacing 2-(4-piperidyl)pyrazine dihydrochloride with 3-(4-fluoro-4-piperidyl)pyridine dihydrochloride (ENAMINE, 0.38 mmol). ¹H NMR (300 MHz, CD₂Cl₂) δ ppm: 8.63-8.62 (m, 1H), 8.57-8.54 (m, 1H), 7.71-7.67 (m, 1H), 7.35-7.31 (m, 1H), 4.68-4.62 (m, 1H), 3.87-3.80 (m, 1H), 3.57-3.47 (m, 1H), 3.07-2.98 (m, 1H), 2.67-2.45 (m, 4H), 2.14-1.86 (m, 4H). [ES+MS] m/z 305 (MH⁺).

Example 3: 4,4,4-trifluoro-1-[4-(5-fluoro-3-pyridyl)-1-piperidyl]butan-1-one

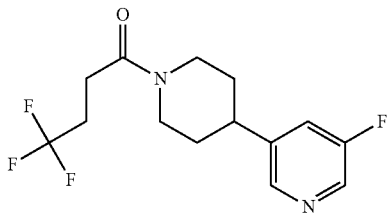 [SMILES: O=C(CCC(F)(F)F)N1CCC(c2cncc(F)c2)CC1]

A sealed tube was backfilled with argon and degassed 1,4-dioxane (4 mL) was added. Then Intermediate 3 (1.1 g, 2.7 mmol), (5-fluoro-3-pyridyl)boronic acid (ENAMINE, 575.0 mg, 4.08 mmol) and 052003 (SIGMA-ALDRICH, 1.35 g, 4.15 mmol) were added. The solution was exposed to microwave irradiation for 45 min at 150° C. The reaction mixture was quenched with a saturated solution of NaHCO₃ (2 mL) and extracted with DCM (×3). The organic layer was dried over (anh) MgSO₄ and evaporated. The residue was purified on silica gel using a linear gradient of DCM/MeOH to give 121.9 mg of as a white solid. The residue was purified by preparative HPLC (OmniSpher C18 column, 10μ,41×250 mm) gradient 30 min 10% to 100% ACN/H₂O (0.1% formic acid) to give title compound (95.0 mg, 11.5%) as a white solid. ¹H NMR (300 MHz, CD₂Cl₂) δ ppm: 8.32-8.30 (m, 2H), 7.28-7.23 (m, 1H), 4.78-4.71 (m, 1H), 3.99-3.92 (m, 1H), 3.20-3.11 (m, 1H), 2.90-2.80 (m, 1H), 2.71-2.43 (m, 5H), 1.96-1.87 (m, 2H), 1.68-1.51 (m, 2H). [ES+MS] m/z 305 (MH⁺).

Example 4: 4,4,4-trifluoro-1-[4-(6-fluoro-3-pyridyl)-1-piperidyl]butan-1-one

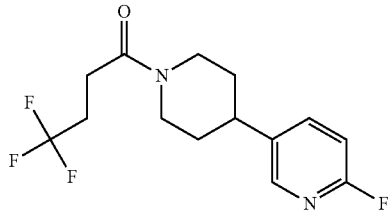 [SMILES: O=C(CCC(F)(F)F)N1CCC(c2ccc(F)nc2)CC1]

Intermediate 16 (121.0 mg, 0.4 mmol) was dissolved in MeOH (2 mL). Then ammonium formate (SIGMA-ALDRICH, 86.9 mg, 1.38 mmol) and 10% Pd/C (ALFA-AESAR, 44.0 mg, 0.04 mmol) were added slowly. The reaction mixture was heated at 65° C. for 3 h, cooled to rt and filtered over a pad of Celite and the filtrate was evaporated. The residue was purified by preparative HPLC (OmniSpher C18 column, 10p, 41×250 mm) gradient 30 min 10% to 100% ACN/H₂O (0.1% formic acid) to give title compound (49.4 mg, 40.1%) as a colorless oil. ¹H NMR (300 MHz, CD₂Cl₂) δ ppm: 8.06-8.04 (m, 1H), 7.67-7.57 (m, 1H), 6.91-6.87 (m, 1H), 4.78-4.70 (m, 1H), 3.99-3.91 (m, 1H), 3.20-3.10 (m, 1H), 2.85-2.77 (m, 1H), 2.70-2.43 (m, 5H), 1.95-1.83 (m, 1H), 1.67-1.50 (m, 1H). [ES+MS] m/z 305 (MH⁺).

Examples 5-16 were prepared by a method analogous to that described for Example 4, replacing Intermediate 16 with those indicated in Table 8. Modifications in the protocol and purification step are also indicated.

TABLE 8

| Ex. | Structure | Int. | Physical data |
| --- | --- | --- | --- |
| 5 | 4,4,4-trifluoro-1-[4-[6-(trifluoromethyl)-3-pyridyl]-1-piperidyl]butan-1-one<br>See footnotes a) and d) | 17<br>1.97 mmol | ¹H NMR (300 MHz, CD₂Cl₂) δ ppm: 8.60-8.59 (m, 1H), 7.73-7.63 (m, 2H), 4.81-4.73 (m, 1H), 4.01-3.94 (m, 1H), 3.22-3.13 (m, 1H), 2.95-2.86 (m, 1H), 2.73-2.43 (m, 5H), 1.99-1.87 (m, 2H), 1.72-1.56 (m, 2H). [ES + MS] m/z 355 (MH⁺). |

TABLE 8-continued

| Ex. | Structure | Int. | Physical data |
|---|---|---|---|
| 6 | 4,4,4-trifluoro-1-[4-[4-(trifluoromethyl)-2-pyridyl]-1-piperidyl]butan-1-one<br>See footnotes a) and d) | 18<br>1.96 mmol | $^1$H NMR (300 MHz, CD$_2$Cl$_2$) δ ppm: 8.71 (d, J = 4.9 Hz, 1H), 7.39-7.37 (m, 2H), 4.75-4.68 (m, 1H), 4.00-3.92 (m, 1H), 3.24-3.14 (m, 1H), 3.08-2.99 (m, 1H), 2.77-2.67 (m, 1H), 2.65-2.43 (m, 4H), 2.06-1.94 (m, 2H), 1.87-1.65 (m, 2H). [ES + MS] m/z 355 (MH$^+$). |
| 7 | 4,4,4-trifluoro-1-[4-[5-trifluoromethyl)-3-pyridyl]-1-piperidyl]butan-1-one<br>See footnotes a) and d) | 19<br>1.74 mmol | $^1$H NMR (300 MHz, CD$_2$Cl$_2$) δ ppm: 8.73 (d, J = 1.2 Hz, 1H), 6.68 (d, J = 2.0 Hz, 1H), 7.77-7.76 (m, 1H), 4.80-4.74 (m, 1H), 4.01-3.96 (m, 1H), 3.23-3.13 (m, 1H), 2.96-2.86 (m, 1H), 2.72-2.43 (m, 5H), 1.99-1.88 (m, 2H), 1.74-1.56 (m, 2H). [ES + MS] m/z 355 (MH$^+$). |
| 8 | 4,4,4-trifluoro-1-[4-[6-(trifluoromethyl)-2-pyridyl]-1-piperidyl]butan-1-one<br>See footnotes a) and d) | 20<br>1.57 mmol | $^1$H NMR (300 MHz, CD$_2$Cl$_2$) δ ppm: 7.86-7.81 (m, 1H), 7.55-7.53 (m, 1H), 7.38 (d, J = 7.9 Hz, 1H), 4.74-4.67 (m, 1H), 4.00-3.92 (m, 1H), 3.24-3.14 (m, 1H), 3.08-2.99 (m, 1H), 2.73 (dd, J = 12.9, 2.7 Hz, 1H), 2.65-2.43 (m, 4H), 2.07-1.93 (m, 2H), 1.86-1.68 (m, 2H). [ES + MS] m/z 355 (MH$^+$). |
| 9 | 4,4,4-trifluoro-1-[4-(6-fluoro-2-pyridyl)-1-piperidyl]butan-1-one<br>See footnotes a) and d) | 21<br>1.82 mmol | $^1$H NMR (300 MHz, CD$_2$Cl$_2$) δ ppm: 7.77-7.69 (m, 1H), 7.07-7.04 (m, 1H), 6.78-6.74 (m, 1H), 4.72-4.65 (m, 1H), 3.97-3.89 (m, 1H), 3.19-3.10 (m, 1H), 2.93-2.84 (m, 1H), 2.72-2.41 (m, 5H), 2.01-1.87 (m, 2H), 1.80-1.58 (m, 2H). [ES + MS] m/z 305 (MH$^+$). |

TABLE 8-continued

| Ex. | Structure | Int. | Physical data |
|---|---|---|---|
| 10 | 4,4,4-trifluoro-1-[4-(6-methoxy-3-pyridyl)-1-piperidyl]butan-1-one<br>See footnotes a) and d) | 22<br>2.07 mmol | $^1$H NMR (300 MHz, CD$_2$Cl$_2$) δ ppm: 8.01-7.99 (m, 1H), 7.48-7.41 (m, 1H), 6.71-6.68 (m, 1H), 4.75-4.68 (m, 1H), 3.97-3.89 (m, 1H), 3.88 (s, 3.19-3.09 (m, 1H), 2.78-2.43 (m, 6H), 1.92-1.81 (m, 2H), 1.65-1.48 (m, 2H). [ES + MS] m/z 317 (MH$^+$). |
| 11 | 4,4,4-trifluoro-1-[4-[2-(trifluoromethyl)-3-pyridyl]-1-piperidyl]butan-1-one<br>See footnotes b) and d) | 23<br>1.54 mmol | $^1$H NMR (300 MHz, CD$_2$Cl$_2$) δ ppm: 8.52-8.50 (m, 1H), 7.79 (d, J = 8.0 Hz, 1H), 7.49 (dd, J = 8.0, 4.6 Hz, 1H), 4.81-4.73 (m, 1H), 4.01-3.93 (m, 1H), 3.25-3.13 (m, 2H), 2.72-2.43 (m, 5H), 1.90-1.81 (m, 2H), 1.71-1.56 (m, 2H). [ES + MS] m/z 355 (MH$^+$). |
| 12 | 4,4,4-trifluoro-1-[4-(5-methoxy-3-pyridyl)-1-piperidyl]butan-1-one<br>See footnotes a) and e) | 24<br>1.86 mmol | $^1$H NMR (300 MHz, CD$_2$Cl$_2$) δ ppm: 8.13 (d, J = 2.8 Hz, 1H), 8.07 (d, J = 1.7 Hz, 1H), 7.03-7.02 (m, 1H), 4.77-4.70 (m, 1H), 3.98-3.91 (m, 1H), 3.83 (s, 3H), 3.19-3.09 (m, 1H), 2.84-2.73 (m, 1H), 2.69-2.43 (m, 5H), 1.95-1.83 (m, 2H), 1.69-1.52 (m, 2H). [ES + MS] m/z 317 (MH$^+$). |
| 13 | 1-[4-(3,5-difluoro-2-pyridyl)-1-piperidyl]-4,4,4-trifluoro-butan-1-one<br>See footnotes c) and e) | 25<br>1.32 mmol | $^1$H NMR (300 MHz, CD$_2$Cl$_2$) δ ppm: 8.26 (d, J = 2.4 Hz, 1H), 7.26-7.15 (m, 1H), 4.71-4.64 (m, 1H), 3.98-3.90 (m, 1H), 3.32-3.14 (m, 2H), 2.77-2.68 (m, 1H), 2.64-2.42 (m, 4H), 1.96-1.68 (m, 4H). [ES + MS] m/z 317 (MH$^+$). |

TABLE 8-continued

| Ex. | Structure | Int. | Physical data |
|---|---|---|---|
| 14 | 1-[4-(2,6-difluoro-3-pyridyl)-1-piperidyl]-4,4,4-trifluoro-butan-1-one<br>See footnotes c) and e) | 26<br>1.95 mmol | $^1$H NMR (300 MHz, CD$_2$Cl$_2$) δ ppm: 7.77-7.68 (m, 1H), 6.84-6.80 (m, 1H), 4.79-4.71 (m, 1H), 3.99-3.91 (m, 1H), 3.22-3.12 (m, 1H), 3.07-2.99 (m, 1H), 2.71-2.42 (m, 5H), 1.96-1.83 (m, 2H), 1.68-1.53 (m, 2H). [ES + MS] m/z 323 (MH$^+$). |
| Ref. Ex. 15 | 4,4,4-trifluoro-1-[4-[4-(trifluoromethyl)pyrimidin-2-yl]-1-piperidyl]butan-1-one<br>See footnotes a) and d) | 27<br>2.30 mmol | $^1$H NMR (300 MHz, CD$_2$Cl$_2$) δ ppm: 8.95 (d, J = 4.97 Hz, 1H), 7.50 (d, J = 5.01 Hz, 1H), 4.68-4.60 (m, 1H), 3.98-3.90 (m, 1H), 3.29-3.17 (m, 2H), 2.84-2.75 (m, 1H), 2.64-2.42 (m, 4H), 2.16-2.05 (m, 2H), 1.96-1.72 (m, 2H). [ES + MS] m/z 356 (MH$^+$). |
| Ref. Ex. 16 | 4,4,4-trifluoro-1-(4-pyrimidin-5-yl-1-piperidyl)butan-1-one<br>See footnote f) | 33<br>0.53 mmol | $^1$H NMR (300 MHz, CD$_2$Cl$_2$) δ ppm: 9.06 (s, 1H), 8.61 (s, 2H), 4.81-4.74 (m, 1H), 4.02-3.97 (m, 1H), 3.23-3.13 (m, 1H), 2.86-2.78 (m, 1H), 2.71-2.42 (m, 5H), 1.99-1.91 (m, 2H), 1.74-1.57 (m, 2H). [ES + MS] m/z 288 (MH$^+$). | a) The reaction mixture was heated at 65° C. for 1 h
b) The reaction mixture was heated at 65° C. for 1 h 30 min
c) The reaction mixture was heated at 65° C. for 30 min
d) Residue was purified by preparative HPLC (OmniSpher C18 column, 10μ, 41 × 250 mm) gradient 30 min 10% to 100% ACN/H$_2$O (0.1% formic acid)
e) Residue was purified by preparative HPLC (OmniSpher C18 column, 10μ, 41 × 250 mm) gradient 35 min 10% to 100% ACN/H$_2$O (0.1% formic acid)
f) The reaction mixture was heated at reflux for 6 h

Example 17: 4,4,4-trifluoro-1-[4-(5-fluoro-2-pyridyl)-1-piperidyl]butan-1-one

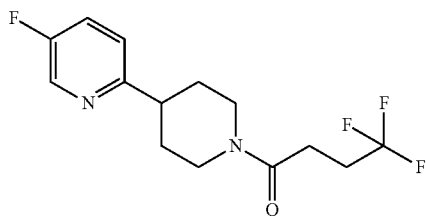 [SMILES: O=C(CCC(F)(F)F)N1CCC(c2ccc(F)cn2)CC1]

Intermediate 34 (150 mg, 0.49 mmol) was dissolved in MeOH (1 mL) then ammonium formate (SIGMA-ALDRICH, 94 mg, 1.49 mmol) and 10% Pd/C (ALFA-AESAR, 53 mg, 0.05 mmol) were added slowly. The reaction mixture was heated at reflux for 6 h then cooled to rt. As starting material remained, ammonium formate (SIGMA-ALDRICH, 94 mg, 1.49 mmol) and 10% Pd/C (ALFA-AESAR, 53 mg, 0.05 mmol) were added and the reaction mixture was heated again at reflux for 6 h then cooled to rt and filtered over a pad of Celite. The filtrate was evaporated to give brown oil which was purified by preparative HPLC (OmniSpher C18 column, 10μ,41×250 mm) gradient 19 min 10% to 100% ACN/H$_2$O (0.1% formic acid) to yield title compound (95 mg, 62%) as a colorless oil. $^1$H NMR (300 MHz, CD$_2$Cl$_2$) δ ppm: 8.07 (d, J=2.5 Hz, 1H), 7.69-7.62 (m, 1H), 6.93-6.89 (m, 1H), 4.79-4.73 (m, 1H), 4.01-3.95 (m, 1H), 3.22-3.18 (m, 1H), 2.89-2.78 (m, 1H), 2.72-2.59 (m, 5H), 2.58-2.45 (m, 2H), 1.96-1.87 (m, 2H). [ES+MS] m/z 305 (MH$^+$).

Example 18: 4,4,4-trifluoro-1-(4-(2-(trifluoromethyl)pyridin-4-yl)piperidin-1-yl)butan-1-one

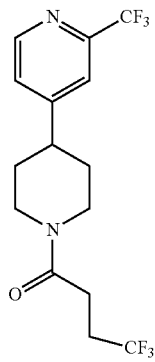 [SMILES: O=C(CCC(F)(F)F)N1CCC(c2ccnc(C(F)(F)F)c2)CC1]

To a solution of Intermediate 36 (75 g, 212.904 mmol) in MeOH (750 mL) was added 10% Pd/C (HINDUSTAN, 22.5 g) at 27° C. The reaction mixture was stirred at the same temperature under hydrogen atmosphere (30 psi) for 1 h in parr shaker. The progress of the reaction was monitored by TLC. On completion of the reaction, the reaction mixture was filtered through Celite and washed with MeOH (4×50 mL). The filtrate was concentrated under reduced pressure. The crude compound was purified by column chromatography (silica gel 100-200 mesh), eluted with a linear gradient of petroelum ether/EtOAc as eluents. The pure fractions were collected and concentrated under reduced pressure to afford tittle compound (55 g, 73%) as a pale yellow thick liquid. Note: The reaction was performed in multiple batches as 20 g×3 and 15 g×1. $^1$H NMR (400 MHz, CDCl$_3$) δ ppm: 8.69-8.64 (m, 1H), 7.52 (s, 1H), 7.35-7.29 (m, 1H), 4.87-4.79 (m, 1H), 4.05-3.96 (m, 1H), 3.25-3.15 (m, 1H), 2.92-2.82 (m, 1H), 2.75-2.47 (m, 5H), 2.03-1.92 (m, 2H), 1.73-1.58 (m, 2H). [ES+MS] m/z 355 (MH$^+$).

Reference Example 19: 4,4,4-trifluoro-1-[4-(pyridazin-3-yl)piperidin-1-yl]butan-1-one

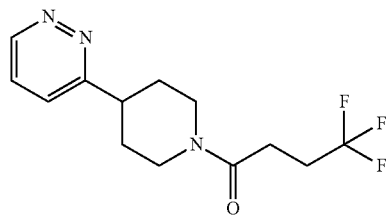 [SMILES: O=C(CCC(F)(F)F)N1CCC(c2cccnn2)CC1]

Intermediate 35 (44.5 mg, 0.16 mmol) was dissolved in EtOH (5 ml), then Pd/C 10% (10 mg) was added and the mixture was stirred under H$_2$ at ambient pressure for 5 h. Monitoring by UPLC showed the formation of the desired product. The catalyst was removed by filtration, the was solvent evaporated and the resulting crude was purified by preparative LCMS to give tittle compound (8.5 mg, 19%) as a pale yellow solid. $^1$H NMR (400 MHz, DMSO-d$_6$) δ ppm: 9.04-9.14 (m, 1H), 7.57-7.69 (m, 2H), 4.45-4.63 (m, 1H), 3.96-4.07 (m, 1H), 3.10-3.25 (m, 2H), 2.43-2.79 (m, 5H), 1.85-1.98 (m, 2H), 1.85-1.67 (m, 1H), 1.65-1.52 (m, 1H). [ES+MS] m/z 288 (MH$^+$).

Example 20: 4,4,4-trifluoro-1-(4-(2-fluoropyridin-4-yl)piperidin-1-yl)butan-1-one

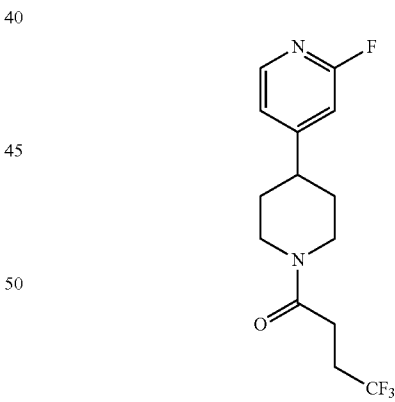

To a solution of Intermediate 41 (350 mg, 1.158 mmol) was dissolved in MeOH (5 mL) and 10% Pd/C (HINDUSTAN, 350 mg) was added at 26° C. The reaction mixture was stirred for 3 h under hydrogen atmosphere at 26° C. The reaction mixture was filtered through Celite and washed with MeOH (20 mL). The filtrate was concentrated under reduced pressure. The crude was purified by preparative HPLC (Kinetex C18 column, 5μ,30×150 mm) gradient 13 min 10% to 100% ACN/Amonium bicarbonate (10 mM aq solution) to yield the title compound (173 mg, 52%). $^1$H NMR (400 MHz, CDCl$_3$) δ ppm: 8.15 (d, J=5.2 Hz, 1H), 7.05-6.98 (m, 1H), 6.76 (s, 1H), 4.85-4.76 (m, 1H), 4.04-3.94 (m, 1H), 3.22-3.16 (m, 1H), 2.88-2.76 (m, 1H), 2.75-2.41 (m, 5H), 2.03-1.88 (m, 2H), 1.70-1.58 (m, 2H). [ES+ MS] m/z 305 (MH⁺).

Examples 21-24 were prepared by methods analogous to that described for Example 20, replacing intermediate 41 with those indicated in Table 9. Modifications in the purification step are also indicated.

TABLE 9

| Ex. | Structure | Int. | Physical data |
|---|---|---|---|
| Ref Ex. 21 | 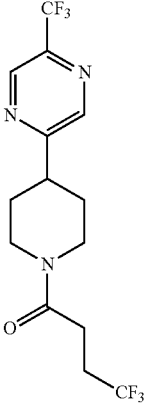<br>4,4,4-trifluoro-1-(4-(5-(trifluoromethyl)pyrazin-2-yl)piperidin-1-yl)butan-1-one<br>See footnote a) | 40<br>0.849 mmol | ¹H NMR (400 MHz, CDCl₃) δ ppm: 8.88 (s, 1H), 8.59 (s, 1H), 4.85-4.75 (m, 1H), 4.06-3.97 (m, 1H), 3.29-3.18 (m, 1H), 3.18-3.07 (m, 1H), 2.83-2.72 (m, 1H), 2.67-2.47 (m, 4H), 2.08-1.96 (m, 2H), 1.95-1.74 (m, 2H). [ES + MS] m/z 356 (MH⁺). |
| 22 | 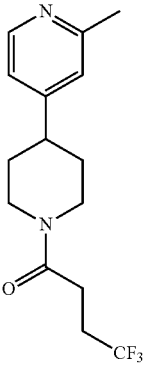 [SMILES: O=C(CCC(F)(F)F)N1CCC(c2ccnc(Cl)c2)CC1]<br>TB110<br>4,4,4-trifluoro-1-(4-(2-methylpyridin-4-yl)piperidin-1-yl)butan-1-one<br>See footnote b) | 42<br>1.34 mmol | 1H NMR (400 MHz, CDCl₃) δ ppm: 8.42 (d, J = 5.2 Hz, 1H), 6.98 (s, 1H), 6.95-6.89 (m, 1H), 4.83-4.75 (m, 1H), 4.01-3.92 (m, 1H), 3.25-3.11 (m, 1H), 2.78-2.47 (m, 9H), 1.97-1.86 (m, 2H), 1.69-1.54 (m, 2H). [ES + MS] m/z 301 (MH⁺). |

TABLE 9-continued

| Ex. | Structure | Int. | Physical data |
| --- | --- | --- | --- |
| 23 | 1-(4-(5,6-difluoropyridin-3-yl)piperidin-1-yl)-4,4,4-trifluorobutan-1-one<br>See footnote c) | 43<br>0.999 mmol | $^1$H NMR (400 MHz, CDCl$_3$) δ ppm: 7.85 (t, J = 2.0 Hz, 1H), 7.44-7.35 (m, 1H), 4.87-4.78 (m, 1H), 4.03-3.97 (m, 1H), 3.24-3.14 (m, 1H), 2.91-2.79 (m, 1H), 2.74-2.44 (m, 5H), 2.02-1.90 (m, 2H), 1.67-1.56 (m, 2H). [ES + MS] m/z 323 (MH$^+$). |
| 24 | 4,4,4-trifluoro-1-(4-(6-(trifluoromethyl)pyrazin-2-yl)piperidin-1-yl)butan-1-one<br>See footnote d) | 44<br>1.416 mmol | $^1$H NMR (400 MHz, CDCl$_3$) δ ppm: 8.83 (s, 1H), 8.70 (s, 1H), 4.81-4.74 (m, 1H), 4.05-3.97 (m, 1H), 3.29-3.19 (m, 1H), 3.18-3.08 (m, 1H), 2.84-2.73 (m, 1H), 2.67-2.48 (m, 4H), 2.10-1.98 (m, 2H), 1.95-1.74 (m, 2H). [ES + MS] m/z 356 (MH$^+$). | a) Purification by preparative HPLC (Kromasil column, 10μ, 21.2 × 250 mm) gradient 16 min 20% to 100% ACN/Ammonium bicarbonate (10 mM aq. solution).

b) Purification by preparative HPLC (Kinetex C-8 column, 5μ, 30 × 150 mm) gradient 14 min 10% to 100% ACN/Ammonium bicarbonate (10 mM aq. solution).

c) Purification by silica chromatography column using a linear gradient of petroleum ether/EtOAc as eluents and then by preparative HPLC (Sunfire C18 column, 5μ, 19 × 150 mm) gradient 15 min 10% to 100% ACN/Ammonium bicarbonate (10 nM aq. solution).

d) Purification by preparative HPLC (Kromasil C18 column, 5μ, 25 × 250 mm) gradient 15 min 40% to 100% ACN/Ammonium bicarbonate (10 mM aq. solution).

Example 25: 1-(4-(2-chloropyridin-4-yl)piperidin-1-yl)-4,4,4-trifluorobutan-1-one

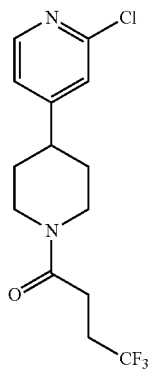

To a solution of Intermediate 37 (370 mg, 1.16 mmol) was dissolved in MeOH (10 mL) and platinum oxide (HINDUSTAN, 35 mg) was added at 26° C. The reaction mixture was stirred for 4 h under hydrogen atmosphere at 26° C. The reaction mixture was filtered through Celite and washed with MeOH (20 mL). The filtrate was concentrated under reduced pressure. The crude was purified by silica chromatography column using a linear gradient of petroleum ether/EtOAc as eluents and then by preparative HPLC (Kinetex C18 column, 5μ, 30×150 mm) gradient 13 min 10% to 100% ACN/Amonium bicarbonate (10 mM aq solution) to yield the title compound (115 mg, 30%). $^1$H NMR (400 MHz, CDCl$_3$) δ ppm: 8.32 (d, J=5.2 Hz, 1H), 7.19-7.15 (m, 1H), 7.07-7.02 (m, 1H), 4.85-4.76 (m, 1H), 4.03-3.93 (m, 1H), 3.25-3.10 (m, 1H), 2.83-2.72 (m, 1H), 2.71-2.46 (m, 5H), 1.99-1.88 (m, 2H), 1.69-1.57 (m, 2H). [ES+MS] m/z 321 (MH$^+$).

Examples 26-27 were prepared by methods analogous to that described for Example 25, replacing intermediate 37 with those indicated in Table 10. Modifications in the purification step are also indicated.

TABLE 10

| Ex. | Structure | Int. | Physical data |
|---|---|---|---|
| 26 | 4,4,4-trifluoro-1-(4-(3-fluoropyridin-4-yl)piperidin-1-yl)butan-1-one<br>See footnote a) | 38<br>0.86 mmol | $^1$H NMR (400 MHz, CDCl$_3$) δ ppm: 8.51-8.28 (m, 2H), 7.16-7.01 (m, 1H), 4.86-4.78 (m, 1H), 4.03-3.94 (m, 1H), 3.28-3.01 (m, 2H), 2.77-2.36 (m, 5H), 2.00-1.85 (m, 2H), 1.71-1.60 (m, 2H). [ES + MS] m/z 305 (MH$^+$). |
| 27 | 1-(4-(6-chloropyridin-2-yl)piperidin-1-yl)-4,4,4-trifluorobutan-1-one<br>See footnote b) | 39<br>0.878 mmol | $^1$H NMR (400 MHz, CDCl$_3$) δ ppm: 7.59 (t, J = 7.8 Hz, 1H), 7.19 (d, J = 7.9 Hz, 1H), 7.06 (d, J = 7.2 Hz, 1H), 4.79-4.72 (m, 1H), 4.00-3.92 (m, 1H), 3.21-3.14 (m, 1H), 2.97-2.85 (m, 1H), 2.75-2.63 (m, 1H), 2.64-2.40 (m, 4H), 2.12-1.88 (m, 2H), 1.81-1.60 (m, 2H). [ES + MS] m/z 321 (MH$^+$). | a) Purification by silica chromatography column using a linear gradient of petroleum ether/EtOAc as eluents.
b) Purification by silica chromatography column using a linear gradient of petroleum ether/EtOAc as eluents and then by preparative HPLC (Atlantis T3 column, 5μ, 19 × 250 mm) gradient 15 min 10% to 100% ACN/H$_2$O (0.1% formic acid).

Reference Example 28: 4,4,4-trifluoro-1-[4-(pyrimidin-2-yl)piperidin-1-yl]butan-1-one

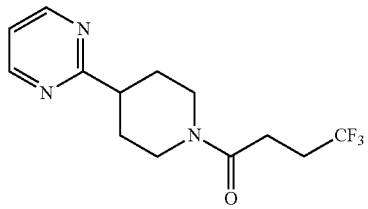 [SMILES: O=C(CCC(F)(F)F)N1CCC(c2ncccn2)CC1]

A solution of EDC.HCl (ALFA-AESAR, 340 mg, 1.77 mmol), TEA (ALFA-AESAR, 0.25 mL, 1.77 mmol), HOBt (ALDRICH, 240 mg, 1.77 mmol), Intermediate 30 (295.3 mg, 1.48 mmol) and 4,4,4-trifluorobutyric acid (ALFA-AESAR, 252 mg, 1.77 mmol) in DMF (15 mL) was stirred at rt overnight. The mixture was then washed with NaHCO$_3$ saturated solution and EtOAc was added, the two phases were separated and the aqueous one was further extracted with EtOAc. The collected organic layer was dried over (anh) Na$_2$SO$_4$, filtered and evaporated. The crude so obtained was purified by flash chromatography (Si SNAP 50, CyHex/EtOAc from 1/1 to 0/10, then DCM/MeOH 8/2) to give title compound (141 mg, 33%) as a white solid. $^1$H NMR (500 MHz, DMSO-d$_6$) δ ppm: 8.75 (d, J=4.9 Hz, 2H), 7.35 (t, J=4.9 Hz, 1H), 4.44 (d, J=13.2 Hz, 1H), 3.94 (d, J=13.7 Hz, 1H), 3.22-3.13 (m, 1H), 3.13-3.05 (m, 1H), 2.82-2.72 (m, 1H), 2.70-2.57 (m, 2H), 2.57-2.45 (m, 2H), 2.02-1.90 (m, 1H), 1.79-1.67 (m, 1H), 1.65-1.51 (m, 1H). [ES+MS] m/z 288 (MH$^+$).

Example 29: 1-(4-(5-chloropyridin-3-yl)-4-fluoropiperidin-1-yl)-4,4,4-trifluorobutan-1-one

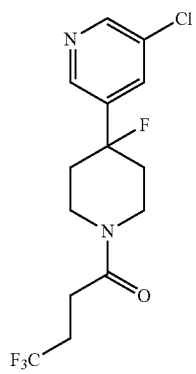 [SMILES: O=C(CCC(F)(F)F)N1CCC(F)(c2cncc(Cl)c2)CC1]

To a solution of Intermediate 68 (650 mg, 2.588 mmol), 4,4,4-trifluorobutanoic acid (MATRIX, 550 mg, 3.882 mmol) in DMF (20 mL) were added DMAP (AVRA, 940 mg, 7.765 mmol) and EDC.HCl (ASHVARSHA, 1.23 g, 6.471 mmol) at 0° C. The resultant reaction mixture was allowed to stir at 26° C. for 16 h. The reaction mixture was quenched with ice cold water (50 mL) and extracted with EtOAc (2×50 mL). Combined organic layers were washed with 1N HCl solution (50 mL) and cold brine (100 mL). The organic layer was dried over (anh) Na$_2$SO$_4$, filtered and concentrated under reduced pressure. The crude was purified by silica chromatography column using a linear gradient of petroleum ether/EtOAc as eluents to yield the title compound (400 mg, 45%) as a colorless liquid. $^1$H NMR (400 MHz, CDCl$_3$) δ ppm: 8.56 (d, J=2.3 Hz, 1H), 8.51-8.45 (m, 1H), 7.71 (t, J=2.2 Hz, 1H), 4.82-4.66 (m, 1H), 3.92-3.82 (m, 1H), 3.65-3.48 (m, 1H), 3.12-2.94 (m, 1H), 2.71-2.47 (m, 4H), 2.18-1.86 (m, 4H). [ES+MS] m/z 339 (MH$^+$).

Example 30: 1-(4-(5-chloropyridin-3-yl)piperidin-1-yl)-4,4,4-trifluorobutan-1-one

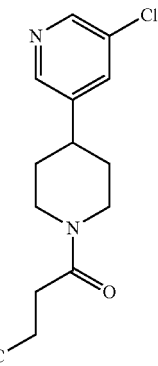

Example 30 was prepared by method analogous to that described for Example 29, but replacing Intermediate 68 with Intermediate 49 (343.34 mmol). The crude was purified by silica gel column chromatography using a linear gradient of petroleum ether/EtOAc as eluents to give title compound (59.47 g, 54%). $^1$H NMR (400 MHz, CDCl$_3$) δ ppm: 8.46 (d, J=2.3 Hz, 1H), 8.42-8.31 (m, 1H), 7.50 (t, J=2.1 Hz, 1H), 4.89-4.73 (m, 1H), 3.99 (d, J=13.5 Hz, 1H), 3.24-3.13 (m, 1H), 2.87-2.76 (m, 1H), 2.74-2.44 (m, 5H), 1.95 (t, J=14.3 Hz, 2H), 1.70-1.61 (m, 2H). [ES+MS] m/z 321 (MH$^+$).

Example 31: 1-(4-(5-chloropyridin-3-yl)piperidin-1-yl)-5,5,5-trifluoropentan-1-one

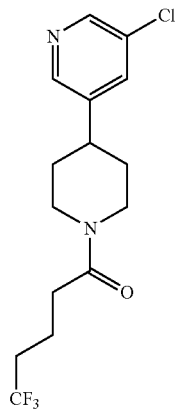 [SMILES: O=C(CCCC(F)(F)F)N1CCC(c2cncc(Cl)c2)CC1]

Example 31 was prepared by method analogous to that described for Example 30, replacing 4,4,4-trifluorobutanoic acid with 5,5,5-trifluoropentanoicacid (OAKWOOD, 10.7082 mmol) The crude was purified by preparative HPLC (Luna C18 column, 5μ,21.2×250 mm) gradient 12.7 min 10% to 100% ACN/Amonium bicarbonate (10 mM aq solution) to yield the title compound (85 mg, 37%) as a brown gum. $^1$H NMR (400 MHz, CDCl$_3$) δ ppm: 8.45 (d, J=2.2 Hz, 1H), 8.36 (d, J=2.0 Hz, 1H), 7.49 (t, J=2.1 Hz, 1H), 4.82 (br d, J=13.6 Hz, 1H), 3.98 (br d, J=13.6 Hz, 1H), 3.25-3.06 (m, 1H), 2.85-2.75 (m, 1H), 2.65 (br s, 1H), 2.45 (t, J=7.2 Hz, 2H), 2.31-2.13 (m, 2H), 2.03-1.83 (m, 4H), 1.68-1.57 (m, 2H). [ES+MS] m/z 335 (MH$^+$).

Example 32: 1-(4-(6-chloropyrazin-2-yl)piperidin-1-yl)-4,4,4-trifluorobutan-1-one

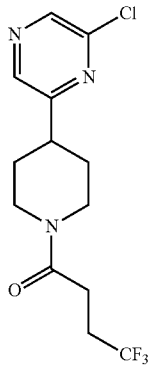 [SMILES: O=C(CCC(F)(F)F)N1CCC(c2cncc(Cl)n2)CC1]

To a solution of Intermediate 50 (400 mg, 1.324 mmol) in ACN (8 mL) was added isopentyl nitrite (RNR, 233 mg, 1.987 mmol) drop wise at 27° C., followed by the addition of copper(II) chloride (ALFA-AESAR, 267 mg, 1.987 mmol). The reaction mixture was heated to 60° C. and stirred for 1.5 h at the same temperature. The reaction mixture was concentrated under reduced pressure, the residue was dissolved in EtOAc (50 mL) and filtered through Celite pad. Water (50 mL) was added to the filtrate and extracted with EtOAc (2×40 mL). The combined organic layer was dried over (anh) Na$_2$SO$_4$, filtered and concentrated under reduced pressure. The crude was purified by preparative HPLC (Kromsil C18 column, 10μ,25×150 mm) gradient 18 min 40% to 100% ACN/Amonium bicarbonate (10 mM aq solution) to yield the title compound (17 mg, 4%) as an off-white solid. $^1$H NMR (400 MHz, DMSO-d$_6$) δ ppm: 8.65 (d, J=6.4 Hz, 2H), 4.52 (br d, J=12.7 Hz, 1H), 3.99 (br d, J=13.6 Hz, 1H), 3.21-3.03 (m, 2H), 2.76-2.60 (m, 3H), 2.59-2.51 (m, 2H), 1.88 (br s, 2H), 1.75-1.63 (m, 1H), 1.59-1.46 (m, 1H). [ES+MS] m/z 322 (MH$^+$).

Example 33: 4,4,4-trifluoro-1-(4-fluoro-4-(pyridin-2-yl)piperidin-1-yl)butan-1-one

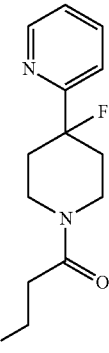

Intermediate 62 (400 mg, 1.323 mmol) in DCM (5 mL) was added a solution of DAST (ALFA-AESAR, 213 mg, 1.587 mmol) in DCM (5 mL) drop wise at −78° C. The reaction mixture was allowed to warm to 27° C. and stirred for 2 h at the same temperature. Reaction mixture was diluted with saturated sodium bicarbonate solution (30 mL) and extracted with DCM (3×100 mL). Combined organic layers were washed with brine solution (30 mL), dried over (anh) Na$_2$SO$_4$, filtered and concentrated under reduced pressure. The crude was purified by silica chromatography column using a linear gradient of petroleum ether/EtOAc as eluents to yield the title compound (160 mg, 31.68%) as a colorless liquid. $^1$H NMR (400 MHz, CDCl$_3$) δ ppm: 8.60-8.51 (m, 1H), 7.80-7.70 (m, 1H), 7.62-7.50 (m, 1H), 7.25-7.20 (m, 1H), 4.79-4.58 (m, 1H), 3.97-3.77 (m, 1H), 3.60-3.47 (m, 1H), 3.10-3.00 (m, 1H), 2.70-2.10 (m, 6H), 2.05-1.84 (m, 2H). [ES+MS] m/z 305 (MH$^+$).

Examples 34-37, 39 and 40 were prepared by methods analogous to that described for Example 33, replacing intermediate 62 with Intermediates indicated in Table 11.

TABLE 11

| Ex. | Structure | Int. | Physical data |
| --- | --- | --- | --- |
| 34 | ![structure] | 63 18.90 mmol | $^1$H NMR (400 MHz, CDCl$_3$) δ ppm: 8.90-8.86 (m, 1H), 8.81 (d, J = 2.2 Hz, 1H), 7.97-7.93 (m, 1H), 4.82-4.67 (m, 1H), 3.99-3.82 (m, 1H), 3.68-3.49 (m, 1H), 3.14-3.01 (m, 1H), 2.77-2.46 (m, 4H), 2.20-2.05 (m, 3H), 2.00-1.91 (m, 1H). [ES + MS] m/z 373 (MH$^+$). |

4,4,4-trifluoro-1-(4-fluoro-4-(5-(trifluoromethyl)pyridin-3-yl)piperidin-1-yl)butan-1-one TABLE 11-continued

| Ex. | Structure | Int. | Physical data |
|---|---|---|---|
| 35 | 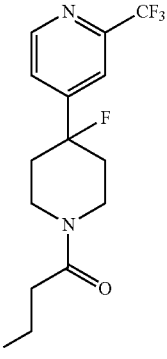  4,4,4-trifluoro-1-(4-fluoro-4-(2-(trifluoromethyl)pyridin-4-yl)piperidin-1-yl)butan-1-one | 64 0.81 mmol | $^1$H NMR (400 MHz, CDCl$_3$) δ ppm: 8.76 (d, J = 5.0 Hz, 1H), 7.67 (s, 1H), 7.48-7.43 (m, 1H), 4.74 (br d, J = 13.6 Hz, 1H), 3.88 (br d, J = 10.7 Hz, 1H), 3.67-3.48 (m, 1H), 3.12-2.97 (m, 1H), 2.72-2.40 (m, 4H), 2.09-1.85 (m, 4H). [ES + MS] m/z 373 (MH$^+$). |
| 36 | 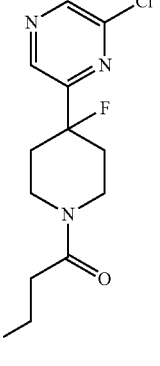  1-(4-(6-chloropyrazin-2-yl)-4-fluoropiperidin-1-yl)-4,4,4-trifluorobutan-1-one | 65 1.184 mmol | $^1$H NMR (400 MHz, CDCl$_3$) δ ppm: 8.80-8.76 (m, 1H), 8.58 (d, J = 0.6 Hz, 1H), 4.78-4.60 (m, 1H), 3.98-3.80 (m, 1H), 3.59-3.47 (m, 1H), 3.11-2.99 (m, 1H), 2.72-2.45 (m, 4H), 2.41-2.11 (m, 2H), 2.00 (q, J = 13.5 Hz, 2H). [ES + MS] m/z 340 (MH$^+$). |
| 37 | 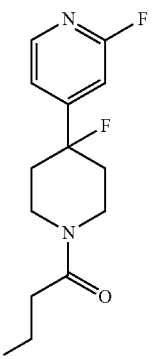  4,4,4-trifluoro-1-(4-fluoro-4-(2-fluoropyridin-4-yl)piperidin-1-yl)butan-1-one | 66 1.875 mmol | $^1$H NMR (400 MHz, CDCl$_3$) δ ppm: 8.27-8.23 (m, 1H), 7.14-7.09 (m, 1H), 6.97-6.90 (m, 1H), 4.72 (d, J = 13.7 Hz, 1H), 3.86 (d, J = 14.1 Hz, 1H), 3.54 (t, J = 12.6 Hz, 1H), 3.10-2.94 (m, 1H), 2.71-2.44 (m, 4H), 2.15-1.81 (m, 4H). [ES + MS] m/z 323 (MH$^+$). |

TABLE 11-continued

| Ex. | Structure | Int. | Physical data |
|---|---|---|---|
| 39 | 4,4,4-trifluoro-1-[4-fluoro-4-[4-(trifluoromethyl)-2-pyridyl]-1-piperidyl]butan-1-one | 66a 0.24 mmol | $^1$H NMR (300 MHz, CDCl$_3$) δ ppm: 8.73 (d, J = 5.0 Hz, 1H), 7.37 (d, J = 1.6 Hz, 1H), 7.81 (s, 1H), 7.47 (d, J = 5.0 Hz, 1H), 4.69 (d, J = 13.5 Hz, 1H), 3.87 (d, J = 13.5 Hz, 1H), 3.59-3.49 (m, 1H), 3.10-3.05 (m, 1H), 2.70-2.47 (m, 4H), 2.47-2.12 (m, 2H), 2.04-1.87 (m, 2H). [ES + MS] m/z 373 (MH$^+$). |
| 40 | 4,4,4-trifluoro-1-(4-fluoro-4-(6-fluoropyridin-3-yl)piperidin-1-yl)butan-1-one | 66b 0.15 mmol | 1H NMR (300 MHz, CD$_2$Cl$_2$) δ ppm: 8.20-8.29 (m, 1H), 7.84-7.78 (m, 1H), 6.99-7.95 (m, 1H), 4.68-4.61 (m, 1H), 3.87-3.80 (m, 1H), 3.56-3.46 (m, 1H), 3.06-2.96 (m, 1H), 2.69-2.44 (m, 4H), 2.12-1.84 (m, 4H). [ES + MS] m/z 323 (MH+). |

Example 38: 1-(3-(5-chloropyridin-3-yl)pyrrolidin-1-yl)-4,4,4-trifluorobutan-1-one

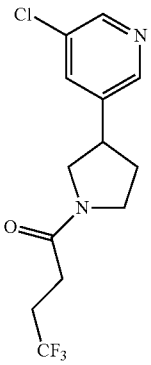 [SMILES: O=C(CCC(F)(F)F)N1CCC(c2cncc(Cl)c2)C1]

To a solution of 4,4,4-trifluorobutanoic acid (OAK-WOOD CHEMICALS, 116 mg, 0.821 mmol) in DCM (2 mL) was added catalytic amount of DMF followed by oxalyl chloride (AVRA, 0.056 mL, 0.657 mmol) in dropwise at 27° C. and stirred for 2 h at the same temperature. The above reaction mixture was added to a solution of Intermediate 74 (120 mg, 0.548 mmol) in mixture of saturated sodium bicarbonate solution (2 mL) and EtOAc (2 mL) at 5° C. The reaction mixture was allowed to 27° C. and stirred for 16 h at the same temperature. The reaction mixture was quenched with saturated sodium bicarbonate solution (5 mL) and extracted with DCM (2×10 mL). The organic layer was dried over (anh) $Na_2SO_4$, filtered and evaporated under reduced pressure. The crude was purified by silica chromatography column using a linear gradient of petroleum ether/EtOAc as eluents to yield the title compound (75 mg) which was again purified by preparative HPLC (XBridge C18 column, 5μ,4.6×250 mm) gradient 18 min 10% to 98% ACN/Ammonium bicarbonate (10 mM aq solution) to yield the title compound (35 mg, 21%) as a colorless liquid. $^1$H NMR (400 MHz, $CDCl_3$) δ ppm: 8.52-8.47 (m, 1H), 8.42-8.39 (m, 1H), 7.57-7.52 (m, 1H), 4.14-3.65 (m, 2H), 3.64-3.32 (m, 3H), 2.65-2.31 (m, 5H), 2.21-1.95 (m, 1H). [ES+MS] m/z 307 (MH$^-$).

Example 41: 144-(2-chloro-4-pyridyl)-4-fluoro-1-piperidyl]-4,4,4-trifluoro-butan-1-one

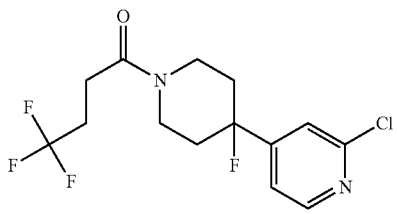 [SMILES: O=C(CCC(F)(F)F)N1CCC(F)(c2ccnc(Cl)c2)CC1]

Example 41 was prepared by method analogous to that described for Example 2, replacing 2-(4-piperidyl)pyrazine dihydrochloride with Intermediate 67b. $^1$H NMR (300 MHz, $CD_2Cl_2$) δ ppm: 8.40 (d, J=5.2 Hz, 1H), 7.37 (d, J=1.6 Hz, 1H), 7.23-7.19 (m, 1H), 4.74-4.62 (m, 1H), 3.92-3.81 (m, 1H), 3.57-3.44 (m, 1H), 3.07-2.95 (m, 1H), 2.70-2.60 (m, 2H), 2.60-2.46 (2H), 2.08-1.99 (2H), 1.99-1.81 (m, 2H). [ES+MS] m/z 339 (MH$^+$).

Biological Activity

Assay 1

Rodent Comparative Data

The following protocol was used to determine oral bioavailability (F %) in rat, the values of which are reported in Table 12 below.

Male SD rats (n=3/compound/route) were used for single intravenous and oral dose PK studies. Compounds were administered intravenously (infusion over 30 minutes) as a solution (Formulation: 5% DMSO: 20% Encapsine in saline; target dose 1 mg/kg) and orally as suspensions (Formulation: 1% Methyl Cellulose; target dose 5 mg/kg). After dosing, blood samples (25 mL) were collected. Sampling times were the following:

0.25, 0.5 (just before end of infusion), 0.58, 0.75, 1, 1.5, 2, 3, 5, 7, and 24 hours; n=3 rats (intravenous infusion administration) 0.25, 0.5, 1, 2, 4, 6, 8, and 24 hours; n=3 rats (oral gavage administration)

All the blood samples were diluted with 25 μL of water and stored at −80° C. until analysis. Rat blood samples were analyzed for each compound using a method upon protein precipitation followed by LC-MS/MS analysis. All pharmacokinetic parameters were obtained by non-compartmental analysis of the different blood concentration-time profiles using WinNonLin Phoenix Version 6.3.

The following protocol was used to determine in vivo safety in mice, the values of which are reported in Table 12 below.

In this study a single dose level of each compound was administered to 6 Swiss (Crl:CD-1(ICR)) male mice of at least 6 weeks of age. They were administered orally, once a day for 7 days, as a suspension in 1% Methylcellulose in a volume of administration of 10 ml/Kg. The dose level in mg/kg for each molecule was selected based on in vitro ADME properties, previous tolerability and efficacy studies and PBPK predictions in order to achieve equivalent blood exposures.

| Compound | mg/Kg |
| --- | --- |
| BDM_44751 of WO 2014/096378 | 100 |
| Example 30 | 50 |
| Example 18 | 100 |

Toxicokinetic (composite) evaluation was performed on blood samples collected from compound-treated dosed animals at 0.5, 1, 3, 7 and 24 h after dosing on Days 1 and 7. A concentration of compounds in whole blood was determined using an H PLC-MS/MS method using a non-compartmental method to obtain estimates of TK parameters: maximum observed compound blood concentration (Cmax), time to Cmax (Tmax), and the area under the compound blood concentration-time curve (AUC). Clinical observations and bodyweights were recording once a day during treatment period and on the day of necropsy, 24 h after last administration. Animals were then sacrificed by $CO_2$ overexposure and exanguination by intracardiac puncture. At necropsy liver was weighed and before preserved in fixative, for optical and electron microscopy analysis, a portion was frozen for gene expression analysis. 3 out of 6 animals were used to complete the study with gene expression analysis. HepatoTaq© consists of 16 subpanels focused on various liver toxicity manifestations or modes, with each subpanel based on the measurement of 4 to 18 different gene mRNA levels using Taqman microfluidic technology.

TABLE 12

|  |  | Example BDM_44751 of WO 2014/096378 | Example 30 | Example 18 |
|---|---|---|---|---|
| In vivo safety (mice) | Mice liver hypertrophy (%) | 65 | 2 | 6 |
|  | In vivo PPAR marker fold increase | >200 | <2 | <6 |
| PK | F % (rat, 5 mg/kg) | 9 | 77 | 75 |

Assay 2

Measurement of Growth Inhibition of *M. tuberculosis* GFP Strains by Combination of Ethionamide (ETH) and Examples 1-41

1. Construction of Mycobacterial Recombinant Strains.

Strain *M. tuberculosis* H37Rv-GFP.

A recombinant strain of *M. tuberculosis* H37Rv expressing the green fluorescent protein (H37Rv-GFP) was obtained by transformation of the integrative plasmid pNIP48 (Abadie et al., 2005; Cremer et al., 2002). In this plasmid derived from the Ms6 mycobacteriophage, the GFP gene was cloned under the strong mycobacterial promoter pBlaF and the GFP was constitutively expressed. This plasmid also contained an hygromycin resistance gene.

Strain *M. tuberculosis* W4-E1-GFP (Mutant).

The *M. tuberculosis* strain E1 was a derivative of the Beijing strain W4 that was selected on ethionamide-containing agar plates (20 μg/ml). This strain carries a Gly343Ala mutation in EthA. The W4-E1 strain was transformed using pNIP48 as described above to give the fluorescent strain W4-E1-GFP.

2. Growth and Preparation of the Fluorescent Mycobacteria

Bacterial stocks kept at −80° C. were used to inoculate 5 ml of Middlebrook 7H9 medium supplemented with oleic acid-albumin-dextrose-catalase (OADC, Difco, Sparks MD, USA) and with 50 μg $ml^{-1}$ hygromycin (Invitrogen, Carlsbad, CA USA) in 25 $cm^2$ tissue-culture flasks. Flasks were incubated at 37° C. without shaking for 7 days. Cultures were then diluted with fresh culture medium to reach an $OD_{600}$ of 0.1. Culture flasks (75 $cm^2$) were filled with 50 ml of this diluted culture, which were cultivated 7 days at 37° C. without shaking.

3. Microplates Preparation

Ethionamide (Sigma, E6005) was diluted in DMSO at 0.1 mg/mL and 0.8 mg/ml; aliquots were stored frozen at −20° C. Test-compounds were resuspended in DMSO at a final concentration of 10 μM. Ethionamide and test-compounds were transferred to a 384-well low-volume polypropylene plate (Corning, no. 3672) and used to prepare assay plates. Ten 3-fold serial dilutions of compounds (typically in the ranges of 30 to 4.5e-3 μM) were performed into black Greiner 384-well clear bottom polystyrene plates (Greiner, no. 781091) using an Echo 550 liquid Handler (Labcyte). DMSO volume were compensated so that the concentration across all wells was equal (0.3%).

Ethionamide was then transferred to the 384-well plates, using Echo. The final concentration of ETH was 0.1 μg/ml for assays involving H37Rv-GFP, and was 0.8 μg/ml for assays involving W4-E1-GFP. The final amount of DMSO in the assay plate remained <1% v/v for each well.

Controls in the assay plate include DMSO at 0.3% (negative control) and INH at 1 μg/ml (positive control). A reference plate included rifampicin, INH and ETH ranging from 30 to 1.8e-3 μg/ml (15 points, 2× dilutions).

Cultures of H37Rv-GFP or of W4-E1-GFP to be added to assay plates were washed two times in PBS (Gibco, 14190), resuspended in fresh culture medium (without Hygromycin), and grown for 5 days at 37° C.

Finally, cultures were diluted to an OD600 nm of 0.02 (using fresh culture medium with no added Hygromycin) and 50 μL were transferred to each assay plate. Assay plates were incubated at 37° C. for 5 days. Fluorescent signal is acquired on a Victor 3 multilabel plate reader (Perkin Elmer), using exc=485 nm/em=535 nm.

All Example compounds were tested essentially according to the procedure described in Assay 2 above and found to have the activity values reported below.

EC50_H37Rv measures the ability of the compounds of the invention to potentiate ethionamide activity against H37Rv strains, whereas EC50_Mutant measures the ability of the compounds of the invention to potentiate ethionamide activity against strains of TB that are resistant to ethionamide.

| Example number | EC50_H37Rv | EC50_Mutant |
|---|---|---|
| 1 (Ref. Ex.) | ++ | + |
| 2 | +++++ | ++ |
| 3 | ++++ | + |
| 4 | ++++ | + |
| 5 | ++ | + |
| 6 | +++++ | ++++ |
| 7 | +++++ | ++++ |
| 8 | ++++ | + |
| 9 | ++++ | +++ |
| 10 | ++++ | ++++ |
| 11 | + | + |
| 12 | ++ | ++ |
| 13 | ++++ | +++ |
| 14 | ++++ | ++++ |
| 15 (Ref. Ex.) | + | + |
| 16 (Ref. Ex.) | + | + |
| 17 | +++++ | + |
| 18 | +++++ | +++++ |
| 19 (Ref. Ex.) | + | † |
| 20 | +++++ | ++++ |
| 21 (Ref. Ex.) | ++ | + |
| 22 | +++++ | ++++ |
| 23 | +++++ | ++++ |
| 24 | ++++ | ++ |
| 25 | +++++ | ++++ |
| 26 | ++++ | ++ |
| 27 | ++++ | ++++ |
| 28 (Ref. Ex.) | + | + |
| 29 | +++++ | +++++ |
| 30 | +++++ | ++++ |
| 31 | ++++ | +++ |
| 32 | +++++ | ++++ |
| 33 | ++++ | ++++ |
| 34 | +++++ | +++++ |
| 35 | +++++ | +++++ |
| 36 | ++++ | +++ |
| 37 | +++++ | +++++ |
| 38 | +++++ | +++++ |
| 39 | ++++ | ++++ |
| 40 | ++++ | ++++ |
| 41 | +++++ | +++++ |

<50 nM = +++++
≥50 nM to <250 nM = ++++
≥250 nM to <500 nM = +++
≥500 nM to <1.0 μM (≥500 nM to <1000 nM) = ++
≥1.0 μM to ≤10 μM (≥1000 nM to ≤10,000 nM) = +
>10 = †

In particular, each of Examples 2, 3, 4, 6 to 10, 13, 14, 17, 18, 20, 22, 23, 24, 25 to 27, 29 to 35, 37, 38, 39, 40 and 41 were found to have an average EC50_H37Rv of <150 nM and an average EC50_Mutant of <1.3 μM.

Specific exemplary compounds are detailed below.

Example 18 was found to have an average EC50_H37Rv of 11 nM and an average EC50_Mutant of 37 nM.

Example 20 was found to have an average EC50_H37Rv of 18 nM and an average EC50_Mutant of 119 nM.

Example 29 was found to have an average EC50_H37Rv of 8 nM and an average EC50_Mutant of 17 nM.

Example 30 was found to have an average EC50_H37Rv of 30 nM and an average EC50_Mutant of 93 nM.

Example 32 was found to have an average EC50_H37Rv of 33 nM and an average EC50_Mutant of 211 nM.

Example 35 was found to have an average EC50_H37Rv of 6 nM and an average EC50_Mutant of 24 nM.

Example 37 was found to have an average EC50_H37Rv of 7 nM and an average EC50_Mutant of 29 nM.

Example 38 was found to have an average EC50_H37Rv of 15 nM and an average EC50_Mutant of 20 nM.

For comparison, Example BDM_70542 of WO 2014/096378 was tested in the same assay as described above and found to have an EC50_Mutant of 1.6 μM, i.e. 1600 nM.

Assay 3

*Mycobacterium tuberculosis* In Vitro H37Rv in Human Macrophages THP-1 Inhibition Assay (Intracellular Assay)

Intracellular screening is a valuable tool for identifying new anti-tuberculosis compounds that are active in human macrophages. This ex-vivo assay may represent physiological conditions that mimic disease and take into consideration the favorable contribution of host cells. (Sorrentino, F. et al. (2016) Antimicrob. Agents Chemother. 60 (1), 640-645.)

Procedure was carried out as described in Sorrentino, F. et al. (2016) Antimicrob. Agents Chemother. 60 (1), 640-645 (supplemental material), except that before THP-1 infected cells were seeded in 384 well plates, infected macrophages were filtered in the last step of wash steps with a 40 um cell strainer to remove cell clumps and obtain single cell suspension.

Compounds of the examples were tested essentially in accordance with the above-mentioned assay (without the presence of ethionamide). The data are provided in the Table below.

| Example Number | IC50 (μM) |
|---|---|
| 2 | +++++ |
| 3 | ++++ |
| 4 | ++++ |
| 5 | + |
| 6 | ++++ |
| 8 | ++++ |
| 9 | ++++ |
| 10 | ++++ |
| 11 | + |
| 12 | ++++ |
| 13 | ++++ |
| 17 | ++++ |
| 18 | +++++ |
| 20 | +++++ |
| 23 | +++++ |
| 24 | ++++ |
| 26 | ++++ |
| 27 | ++++ |
| 29 | +++++ |
| 30 | +++++ |
| 31 | ++++ |
| 32 | +++++ |
| 33 | +++++ |
| 34 | +++++ |
| 35 | +++++ |
| 37 | +++++ |
| 38 | + |

≤50 nM = +++++
≥50 nM to <250 nM = ++++
≥250 nM to <500 nM = +++
≥500 nM to <1.0 μM (≥500 nM to <1000 nM) = ++
≥1.0 μM to ≤10 μM (≥1000 nM to ≤10,000 nM) = +

Specific exemplary compounds are detailed below.
Example 18 was found to have an IC50 of 20 nM.
Example 20 was found to have an IC50 of 30 nM.
Example 29 was found to have an IC50 of 2 nM.
Example 30 was found to have an IC50 of 13 nM.
Example 32 was found to have an IC50 of 40 nM.
Example 35 was found to have an IC50 of 4 nM.
Example 37 was found to have an IC50 of 5 nM.
Example 38 was found to have an IC50 of 1.26 μM.

The invention claimed is:

1. A combination comprising:
   a compound, wherein the compound is 4,4,4-trifluoro-1-(4-(2-(trifluoromethyl)pyridin-4-yl)piperidin-1-yl)butan-1-one having the following structure:

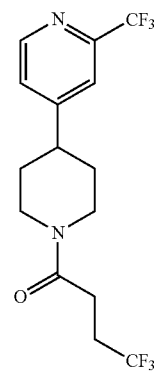 [SMILES: O=C(CCC(F)(F)F)N1CCC(c2ccnc(C(F)(F)F)c2)CC1]

or a pharmaceutically acceptable salt thereof;
   at least one anti-tuberculosis agent selected from isoniazid, rifampin, pyrazinamide, ethambutol, moxifloxacin, rifapentine, clofazimine, ethionamide, prothionamide, isoxyl, thiacetazone, rifabutin, a diarylquinoline, nitroimidazo-oxazine PA-824, delamanid (OPC-67683), an oxazolidinone, EMB analogue SQ109, OPC-167832, GSK3036656 (also known as GSK070), GSK2556286, GSK3211830, a benzothiazinone, an azaindole, a dinitrobenzamide, and a beta-lactam; and
   at least one anti-viral agent selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068, BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

2. The combination of claim 1, wherein the composition is suitable for intravenous delivery.

3. The combination of claim 1, wherein the composition is an inhalable formulation.

4. The combination of claim 1, wherein the diarylquinoline comprises bedaquiline (TMC207) or TBAJ-587, the oxazolidinone comprises linezolid, tedizolid, radezolid, sutezolid (PNU-100480), posizolid (AZD-5847) or TBI-223, the benzothiazinone comprises BTZ043 or PBTZ169, the azaindole comprises TBA-7371, and the beta-lactam comprises meropenem, faropenem, ertapenem, tebipenem, or a beta-lactam combination.

* * * * *